United States Patent
Kadokura et al.

(10) Patent No.: US 8,439,839 B2
(45) Date of Patent: May 14, 2013

(54) ULTRASONIC DIAGNOSIS DEVICE AND ULTRASONIC PROBE FOR USE IN ULTRASONIC DIAGNOSIS DEVICE

(75) Inventors: Masahiko Kadokura, Kanagawa (JP); Makoto Kato, Kanagawa (JP)

(73) Assignee: Panasonic Corporation, Osaka (JP)

( * ) Notice: Subject to any disclaimer, the term of this patent is extended or adjusted under 35 U.S.C. 154(b) by 637 days.

(21) Appl. No.: 12/602,839

(22) PCT Filed: Jun. 2, 2008

(86) PCT No.: PCT/JP2008/001391
§ 371 (c)(1),
(2), (4) Date: Dec. 3, 2009

(87) PCT Pub. No.: WO2008/149540
PCT Pub. Date: Dec. 11, 2008

(65) Prior Publication Data
US 2010/0217125 A1    Aug. 26, 2010

(30) Foreign Application Priority Data

Jun. 4, 2007  (JP) ................. 2007-148463
Aug. 8, 2007  (JP) ................. 2007-206519
Aug. 10, 2007 (JP) ................. 2007-209248
Dec. 10, 2007 (JP) ................. 2007-318465

(51) Int. Cl.
*A61B 8/00*    (2006.01)
(52) U.S. Cl.
USPC ............. 600/438; 600/407; 600/437; 600/443
(58) Field of Classification Search .................. 600/437, 600/438, 440, 443, 447
See application file for complete search history.

(56) References Cited

U.S. PATENT DOCUMENTS 5,152,294 A   10/1992  Mochizuki et al.
5,840,028 A   11/1998  Chubachi et al.
(Continued)

FOREIGN PATENT DOCUMENTS

JP   02-026549   1/1990
JP   4-122358    4/1992
(Continued)

OTHER PUBLICATIONS

International Search Report for corresponding application No. PCT/JP2008/001391 dated Jun. 24, 2008.
(Continued)

*Primary Examiner* — Unsu Jung
*Assistant Examiner* — Amanda Lauritzen
(74) *Attorney, Agent, or Firm* — Renner, Otto, Boisselle & Sklar, LLP

(57) ABSTRACT

An ultrasonic diagnostic apparatus includes a structure for adjusting the positional relationship between an ultrasonic transducer and a blood vessel for measuring an elasticity characteristic. The apparatus includes an ultrasonic probe including a transducer for transmitting an ultrasonic wave and receiving the ultrasonic wave reflected by a tissue of a biological body; and a driving device for physically moving the transducer. For measuring the elasticity characteristic of the blood vessel, the driving device moves the transducer based on a control signal to change at least one of a direction and a position at which the ultrasonic wave is to be transmitted. A determination section specifies a position of the transducer at which the reflection intensity is maximum based on intensity information representing an intensity of the reflected wave. A calculation section calculates the elasticity characteristic of the blood vessel at the specified position.

13 Claims, 33 Drawing Sheets

U.S. PATENT DOCUMENTS

| | | | |
|---|---|---|---|
| 6,623,431 B1 | 9/2003 | Sakuma et al. | |
| 7,338,452 B2 * | 3/2008 | Shiina et al. | 600/467 |
| 8,100,833 B2 * | 1/2012 | Hirota | 600/462 |
| 8,187,196 B2 * | 5/2012 | Amitzur et al. | 600/486 |
| 2004/0034304 A1 | 2/2004 | Sumi | |
| 2010/0185090 A1 * | 7/2010 | Suzuki et al. | 600/443 |
| 2012/0116227 A1 * | 5/2012 | Suzuki et al. | 600/443 |

FOREIGN PATENT DOCUMENTS

| | | |
|---|---|---|
| JP | 10-005226 | 1/1998 |
| JP | 2001-292995 | 10/2001 |
| JP | 2002-263973 | 9/2002 |
| JP | 2003-180686 | 7/2003 |
| JP | 2003-245280 | 9/2003 |
| JP | 2004-229823 | 8/2004 |
| JP | 2005-074146 | 3/2005 |
| JP | 2006-115937 | 5/2006 |
| JP | 2008/001391 | 6/2008 |
| WO | 2006/011504 | 2/2006 |
| WO | 2006/043528 | 4/2006 |

OTHER PUBLICATIONS

Chris L. de Korte et al., "Influence of Catheter Position on Estimated Strain in Intravascular Elastography", IEEE Transactions on Ultrasonics, Ferroelectrics, and Frequency Control, May 1999, vol. 46, No. 3, pp. 616-625.

Roch L. Maurice et al., "Noninvasive Vascular Elastography: Theoretical Framework", IEEE Transactions on Medical Imaging, Feb. 2004, vol. 23, No. 2, pp. 164-180.

Form PCT/ISA/237 and partial English translation dated Jun. 24, 2008.

* cited by examiner

*FIG.11*
(a)
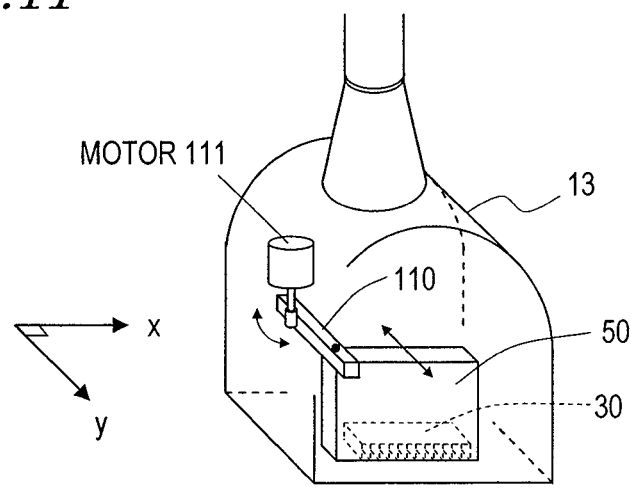
(b)
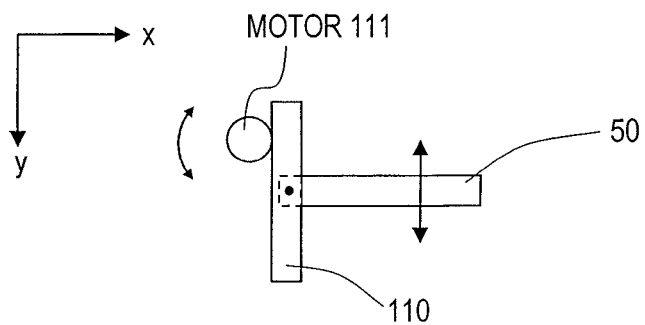

(a)　　　　　　　　　　　(b)

FIG.19
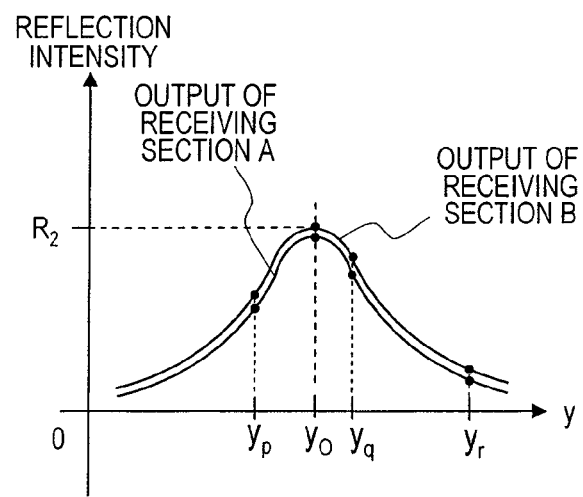
FIG.20
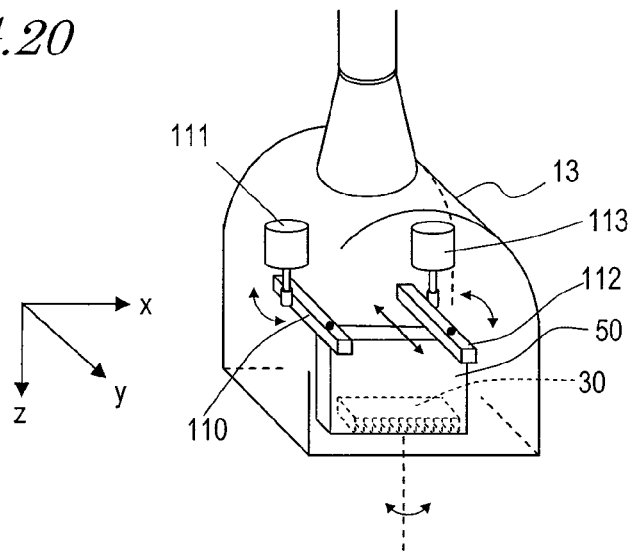
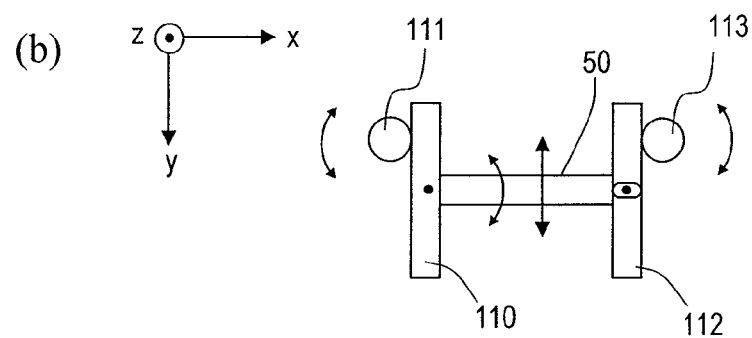

FIG.30
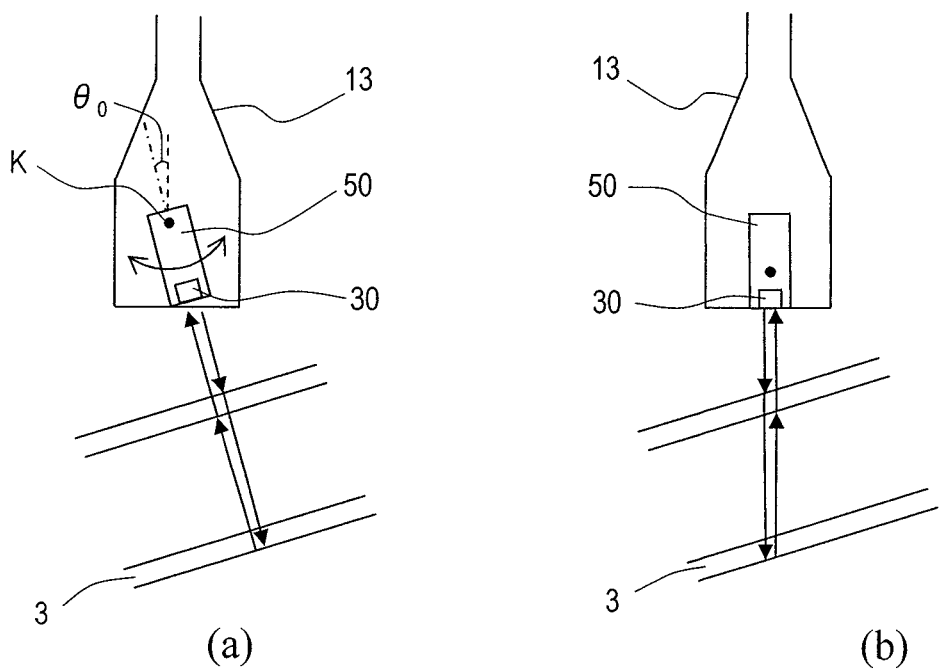
(a)  (b)
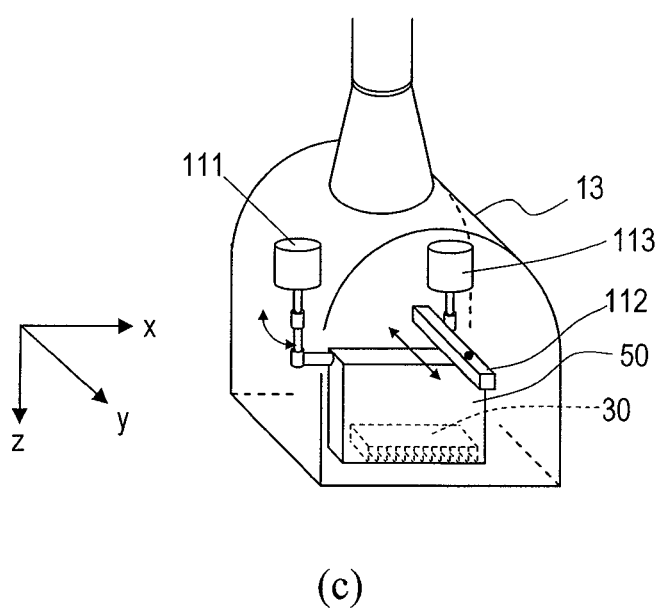
(c)

FIG.47
(a1)
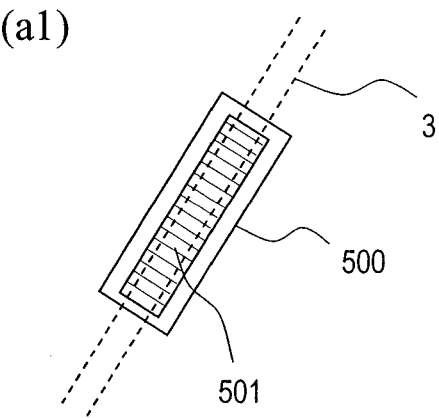
(b1)
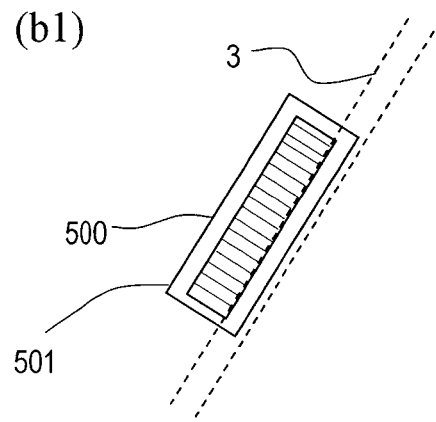
(a2)
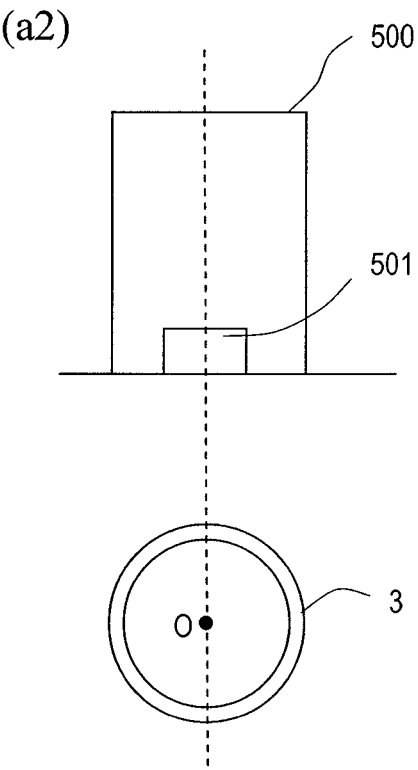
(b2)
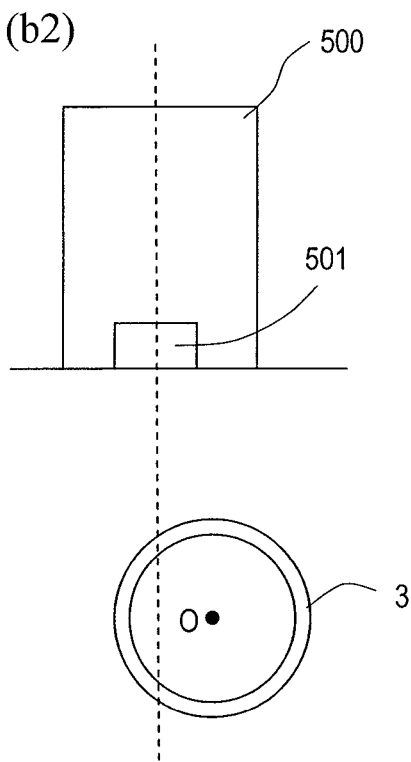

(a)

(b)

(a)

(b)

FIG.50
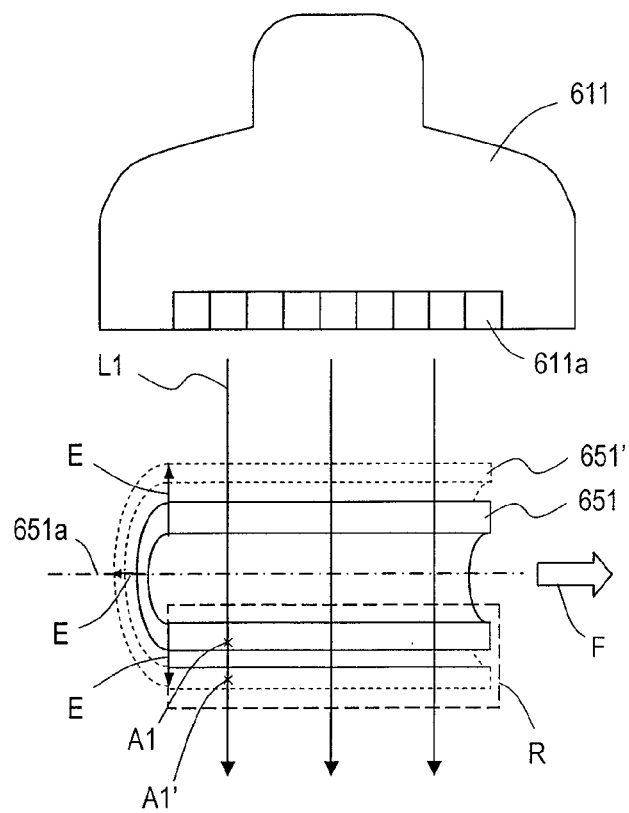
(a)
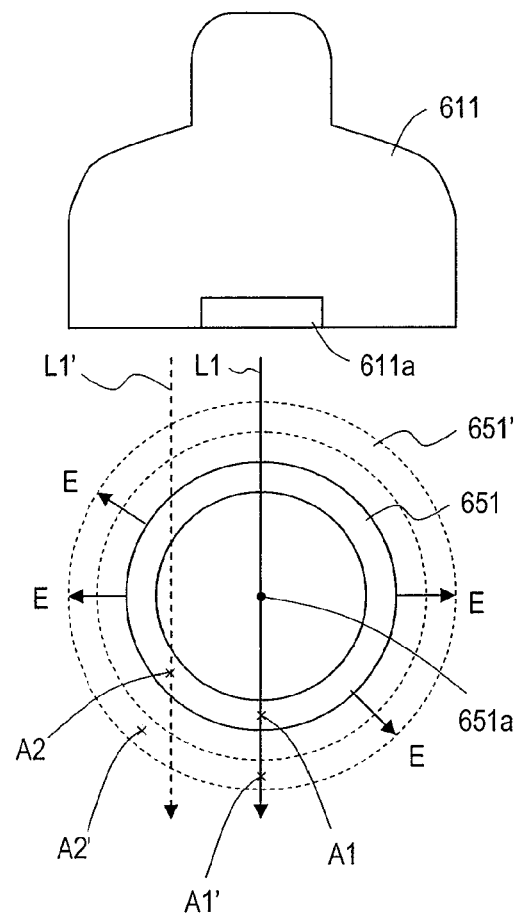
(b)

ULTRASONIC DIAGNOSIS DEVICE AND ULTRASONIC PROBE FOR USE IN ULTRASONIC DIAGNOSIS DEVICE

CROSS-REFERENCE TO RELATED APPLICATIONS

This application is a national stage entry under 35 U.S.C. §371 of PCT Application No. PCT/JP2008/001391 filed Jun. 2, 2008 which claims priority to JP 2007-148463 filed Jun. 4, 2007, JP 2007-206519 filed Aug. 8, 2007, JP 2007-209248 filed Aug. 10, 2007, JP 2007-318465 filed Dec. 10, 2007, all of which are incorporated herein by reference.

TECHNICAL FIELD

The present invention relates to an ultrasonic diagnostic apparatus and an ultrasonic probe for medical uses, and specifically to an ultrasonic diagnostic apparatus for measuring properties of a tissues of a biological body and a method for controlling the same, a structure and a method for controlling an ultrasonic probe usable for the ultrasonic diagnostic apparatus, and an ultrasonic diagnostic apparatus for measuring a blood vessel wall.

BACKGROUND ART

Recently, the number of the people suffering from circulatory diseases such as myocardial infarction and cerebral infarction has been increasing. How to prevent and treat such diseases is an important issue. To the onset of myocardial infarction and cerebral infarction, arteriosclerosis is deeply involved. Specifically, where atheroma is formed on a blood vessel wall or new cells of an artery stop being generated due to any of various factors such as high blood pressure and the like, the artery loses resilience thereof and becomes hard and brittle. As a result, the blood vessel is occluded at the site where the atheroma is formed, the blood vessel tissue covering the atheroma is ruptured and the atheroma flows into the blood vessel and occludes the artery at another site, or the hardened site of the artery is ruptured. These cause the above-described diseases. Therefore, it is important to provide an early diagnosis of arteriosclerosis in order to prevent or treat these diseases. A method or apparatus for providing a diagnosis of the progress level of arteriosclerosis on an early stage is desired.

Conventionally, a diagnosis of an arteriosclerosis lesion is provided by directly observing the inside of a blood vessel using a vascular catheter. However, this method of diagnosis requires the vascular catheter to be inserted into the blood vessel and has a problem of imposing a heavy bodily burden on a test subject. Therefore, the observation with a vascular catheter is used on a test subject who certainly has an arteriosclerosis lesion for the purpose of specifying the site thereof, but is never used for a medical checkup.

Measuring a level of cholesterol, which is a cause of arteriosclerosis, or measuring a blood pressure level does not impose a heavy burden on a test subject and is easy to conduct. However, these levels do not directly indicate the progress level of arteriosclerosis.

Providing a diagnosis of arteriosclerosis on an early stage and administering a therapeutic drug of arteriosclerosis to the test subject is effective to treat the arteriosclerosis. However, once the arteriosclerosis progresses, it is considered to be difficult to completely cure the hardened artery by a therapeutic drug although a further progress could be suppressed by the drug.

For these reasons, a method or apparatus for providing the progress level of arteriosclerosis on an early stage with little burden on the test subject is desired.

As a noninvasive medical diagnostic apparatus which does not impose a heavy burden on a test subject, an ultrasonic diagnostic apparatus or an x-ray diagnostic apparatus is conventionally used. By irradiating the body of a test subject with an ultrasonic wave or an x-ray from outside the body, information on the shape inside the body or information on the time-wise change of the shape can be provided without causing a pain to the test subject. Once the information on the time-wise change of the shape of the measurement target inside the body (motion information) is obtained, the information on the properties of the measurement target can obtained. For example, the elasticity of the blood vessel is found based on a tiny change of the thickness of the blood vessel, which is superimposed on a motion with a large amplitude resulting from the heartbeat, namely, a distortion amount of the blood vessel, and also based on the blood pressure difference. Accordingly, by obtaining the motion information, the elasticity characteristic of the blood vessel in a biological body is found and so the level of arteriosclerosis can be directly found.

Especially, ultrasonic diagnosis realizes the measurement merely by applying an ultrasonic probe to the test subject, and so is superior to the x-ray diagnosis in that administration of a contrast medium to the test subject is not needed and there is no risk of exposure to the x-ray radiation. A conventional ultrasonic diagnostic apparatus provides a tomogram showing the structure of a test subject by converting the intensity of an echo signal into the luminance of the corresponding pixel. The tomogram is provided on a real-time basis and is used to diagnose the structure of the inside of the test subject.

The recent development of electronic technologies is rapidly improving the measurement precision of ultrasonic diagnostic apparatuses. In accordance with this, ultrasonic diagnostic apparatuses for measuring the tiny motions of tissues of the biological body are now under progressive development. Measurement of the tiny motions of the tissues of the biological body at a high precision can provide a detailed two-dimensional distribution of the elasticity characteristic of the arterial wall.

For example, Patent Document No. 1 discloses a technology of tracking the measurement target at a high precision by analyzing the amplitude and phase of an ultrasonic echo signal using the constrained least squares method. This technology is called the "phase-difference tracking method". This technology can measure, at a high precision, a vibration component which is caused by the blood vessel motion and has an amplitude of several microns and a frequency of up to as high as several hundred hertz. It is reported that this technology makes it possible to measure the thickness change or distortion of the blood vessel wall at a high precision on the order of several microns.

Patent Document No. 2 discloses a technology for scanning a plurality of scanning zones defined for a test subject with an ultrasonic wave and measuring the elasticity characteristic of the blood vessel in each scanning zone.

Patent Document No. 3 discloses an ultrasonic diagnostic apparatus which measures a characteristic of the blood vessel which is different from the elasticity characteristic, specifically a value representing the thickness of the carotid artery, as an index used for determining whether or not the test subject has arteriosclerosis. The carotid artery is known to include three layers of an intima, a media and an adventitia from the inside. The ultrasonic diagnostic apparatus described in Patent Document No. 3 measures the total thickness of the intima and the media (intima-media thickness; hereinafter, referred to as "IMT").

The ultrasonic diagnostic apparatus described in Patent Document No. 3 does not include means for measuring the displacement (distortion) of the blood vessel and so cannot measure the elasticity characteristic thereof. This ultrasonic diagnostic apparatus absolutely needs to have a function of providing a three-dimensional display of the blood vessel before the IMT value is measured. The processing of providing such a display is time-consuming and cannot avoid increasing the cost.

Patent Documents Nos. 4 and 5 each disclose a technology for finding a value representing the shape of the blood vessel wall using the technology of Patent Document No. 1 and calculating the elasticity characteristic. Patent Document No. 6 discloses a technology for providing a three-dimensional image of the shape of the blood vessel and finding the thickness of the blood vessel wall at an arbitrary cross-section thereof from the obtained three-dimensional image.

Patent Document No. 1: Japanese Laid-Open Patent Publication No. 10-5226
Patent Document No. 2: Japanese Laid-Open Patent Publication No. 2001-292995
Patent Document No. 3: Japanese Laid-Open Patent Publication No. 2006-000456
Patent Document No. 4: International Publication No. 2006/011504 pamphlet
Patent Document No. 5: International Publication No. 2006/043528 pamphlet
Patent Document No. 6: Japanese Laid-Open Patent Publication No. 2006-456

DISCLOSURE OF THE INVENTION

Problems to be Solved by the Invention

In order to accurately measure the elasticity characteristic of a blood vessel, accurate information on a time-wise change of the shape of the blood vessel (motion information) is necessary. For obtaining such information, the displacement of the blood vessel needs to be measured in the state where an acoustic line of an ultrasonic wave passes the center of the cross-section of the blood vessel.

For example, portion (a1) of FIG. 47 is a plan view of a probe 500 ideally located with respect to a blood vessel 3, and portion (a2) of FIG. 47 is a cross-sectional view thereof. The acoustic line of an ultrasonic wave which is output from a transducer 501 provided in the probe 500 passes the center o of the cross-section of the blood vessel 3. In this state, a direction in which the thickness of the blood vessel 3 is changed by the heartbeat matches the direction of the acoustic line. Therefore, the distortion amount of the blood vessel 3 can be accurately measured. Hence, the elasticity characteristic can be accurately measured.

However, in a conventional ultrasonic diagnostic apparatus, attention is not especially paid to whether or not the acoustic line of the ultrasonic wave passes the center of the cross-section of the blood vessel. A conceivable reason for this is that there is a premise that a user of the ultrasonic diagnostic apparatus is skillful in operating the apparatus. However, it is naturally expected that the apparatus is operated by an unaccustomed user, and so it is not appropriate to provide such a premise.

It is difficult for an unaccustomed user to locate the probe such that the acoustic line of the ultrasonic wave passes the center of the cross-section of the blood vessel. For example, portion (b1) of FIG. 47 is a plan view of the probe 500 located at a position deviated from the center of the blood vessel 3, and portion (b2) of FIG. 47 is a cross-sectional view thereof. In this state, the direction in which the thickness of the blood vessel 3 is changed does not match the direction of the acoustic line. Therefore, the distortion amount of the blood vessel 3 cannot be measured accurately.

Portions (a) and (b) of FIG. 48 are each a plan view of the probe 500 located unparallel to the blood vessel 3. The acoustic line from the transducer 501 does not always pass the center of the cross-section of the blood vessel 3, and so the distortion amount of the blood vessel 3 cannot be measured accurately.

In any of the cases of portions (b1) and (b2) of FIG. 47 and portions (a) and (b) of FIG. 48, it is difficult for, especially, a user not accustomed to operating the apparatus to find the center of the blood vessel manually while watching the image. Thus, the measured elasticity characteristic is inaccurate.

FIG. 47 shows an example in which the probe 500 is located parallel to the blood vessel 3. However, since the direction of the blood vessel 3 cannot be visually recognized from outside, the probe 500 may occasionally be located almost perpendicular to the blood vessel 3. Portion (a) and (b) of FIG. 49 are each a plan view of the probe 500 located unparallel to the blood vessel 3. The acoustic line from the transducer 501 does not always pass the center of the cross-section of the blood vessel 3, and so the distortion amount of the blood vessel 3 cannot be measured accurately.

In addition, the blood vessel does not necessarily extend parallel to the epidermis. In the case where the blood vessel 3 extends in the depth direction of the body from the epidermis, in whichever manner the probe 500 may be located on a plane parallel to the epidermis, the acoustic line from the transducer 501 does not always pass the center of the cross-section of the blood vessel. As a result, the distortion amount of the blood vessel cannot be measured accurately.

In any of the above-mentioned cases, it is difficult for, especially, a user not accustomed to operating the apparatus to find the center of the blood vessel manually while watching the image. Thus, the measured elasticity characteristic is inaccurate.

There are also other problems. Hereinafter, these problems will be described with background technologies thereof.

Portion (a) and (b) of FIG. 50 schematically show the locations of a probe and a blood vessel 651 for analyzing the motion of the wall of an artery blood vessel (hereinafter, referred to simply as the "blood vessel") using an ultrasonic diagnostic apparatus. Portion (a) of FIG. 50 shows a cross-section of the blood vessel wall which is parallel to an axis of the blood vessel and includes the axis, and portion (b) of FIG. 50 shows a cross-section which is perpendicular to the axis. As shown in these figures, the blood vessel 651 expands or contracts in a diametric direction E in accordance with the blood flow moving in the blood vessel and a change of the blood pressure. Namely, as the blood vessel expands or contracts, the blood vessel wall moves radially with the axis 651a as the center. Therefore, tissues of the wall of the blood vessel 651 are each parallel to the axis 651a and move on a plane including the axis 651a and the tissues thereof.

The expansion and contraction of the blood vessel is caused by a motion only in a direction perpendicular to the axis 651a of the blood vessel wall. Accordingly, when, as shown in portion (a) of FIG. 50, ultrasonic wave beams L1 are output for performing a scan from a plurality of transducers 611a of an ultrasonic probe 611 in a direction perpendicular to the axis 651a along a plane including the axis 651a, the tissues each move only on the acoustic line of the corresponding ultrasonic beam. Accordingly, the motion of the blood vessel wall can be analyzed by an echo signal obtained from the corresponding ultrasonic beam. In other words, the motion of a tissue of the blood vessel wall on an ultrasonic beam can be found without using an echo signal obtained from an adjacent ultrasonic beam. For example, as shown in portion (a) of FIG. 50, a tissue at a position A1 moves to a position A1' by the expansion of the blood vessel 651, but this tissue is located on the same acoustic line before and after being moved. Therefore, the motion of the tissue at the position A1 can be analyzed using only the echo signal obtained from the ultrasonic beam having the acoustic line passing the position A1. Accordingly, by causing an ultrasonic beam to be incident on the artery along a cross-section passing an axis of the artery in a direction perpendicular to the axis and receiving an ultrasonic echo, a two-dimensional distribution of a thickness change amount of a tissue of the blood vessel wall can be measured, and the elasticity characteristic can be found, with a relatively small calculation amount.

In the case where, as shown in portion (b) of FIG. 50, an ultrasonic beam L1' is transmitted to a tissue at a position A2 of the blood vessel 651 along a plane which does not pass the axis 651a of the blood vessel, the tissue at the position A2 moves to a position A2' by the expansion of the blood vessel 651. However, the acoustic line of the ultrasonic beam L1' is not at the position A2'. Therefore, the motion of the tissue at the position A2 cannot be analyzed using the ultrasonic beam L1' which does not pass the axis 651a. As understood from this, for analyzing the motion of each tissue of the blood vessel wall using an ultrasonic wave, it is important that the ultrasonic beam should be output for performing a scan along a cross-section which is parallel to the axis of the blood vessel wall and includes the axis.

In the case where the motion of the blood vessel wall is analyzed by the above-described method to find the elasticity characteristic of the tissue, there is a premise that the position of the blood vessel does not change although the blood vessel expands or contracts. Generally, the premise that the position of the blood vessel does not change holds true because there are extravascular tissues around the blood vessel for keeping the position of the blood vessel. However, depending on the position of the blood vessel or the test subject, the blood vessel may possibly be deviated sideways to a position parallel to the axis of the blood vessel. For example, as shown in FIG. 51, the blood vessel 651 located in an extravascular tissue 652 may be translated as represented with arrow D with respect to the axis 651a to a position represented by dashed line 651'. The movement of the position of the axis 651 by the expansion or contraction of the blood vessel 651 is considered to occur in the case where the extravascular tissue 652 surrounding the blood vessel 651 has a non-uniform composition; for example, a part of the blood vessel 651 is surrounded by fat and the remaining part thereof is surrounded by muscle. Such a movement is related to the expansion or contraction of the blood vessel 651 and so occurs at a cycle matching one cardiac cycle.

When the blood vessel 651 is deviated sideways, the ultrasonic beam L1 output for scanning the plane passing the axis 651a is deviated from the axis 651a as the blood vessel moves. As a result, the tissue at the position A1 which is set on the plane passing the axis 651a is deviated from the acoustic line of the ultrasonic beam L1, and the motion cannot be analyzed accurately.

In order to solve such a problem, it is conceivable to analyze the blood vessel three-dimensionally (for example, Patent Document No. 6). However, the technology described in Patent Document No. 6 merely finds a three-dimensional shape of the blood vessel at a certain time, and does not analyze the motion of the blood vessel wall three-dimensionally.

It is theoretically possible to analyze the motion of the blood vessel three-dimensionally. However, in order to analyze the motion of the blood vessel three-dimensionally, a large scale circuit is necessary and also the calculation amount for tracing the measurement target point is tremendous. Especially, the calculation amount for finding the thickness change amount of, or the elasticity characteristic of, the tissue of the biological body is significantly larger than the calculation amount for finding the motion velocity of the measurement target point. Therefore, it is very difficult to perform such a large amount of calculation with a calculation circuit used for a conventional ultrasonic diagnostic apparatus. If a computer having a very high calculation ability is used for the ultrasonic diagnostic apparatus, the ultrasonic diagnostic apparatus becomes very expensive.

An object of the present invention is to provide a structure for adjusting the positional relationship between an ultrasonic transducer and a blood vessel such that an acoustic line from the ultrasonic transducer passes the center of a cross-section of the blood vessel for measuring an elasticity characteristic. Another object of the present invention is to provide an ultrasonic diagnostic apparatus capable of accurately measuring a thickness change amount of, or the elasticity characteristic of, a tissue of a biological body using a simple calculation circuit in consideration of a sideway deviation of the blood vessel wall.

Means for Solving the Problems

An ultrasonic probe according to the present invention is connectable to an ultrasonic diagnostic apparatus and comprises a transducer for transmitting an ultrasonic wave and receiving the ultrasonic wave reflected by a tissue of a biological body; and a driving device for changing a position of the transducer. While the ultrasonic diagnostic apparatus measures a property of a blood vessel, the driving device changes the position of the transducer based on a control signal from the ultrasonic diagnostic apparatus to change at least one of a direction and a position at which the ultrasonic wave is to be transmitted.

A movable range may be defined for the transducer; and while the transducer is transmitting or receiving the ultrasonic wave, the driving device may change the position of the transducer within the movable range.

The driving device may move the transducer in a direction parallel to a surface of the biological body in contact with the ultrasonic probe to change the position from which the ultrasonic wave is to be transmitted.

The transducer may include at least one line of ultrasonic transducer elements arranged in a first direction; and the driving device may move the transducer in a second direction which is on a plane parallel to the surface of the biological body in contact with the ultrasonic probe and is perpendicular to the first direction.

The transducer may include at least one line of ultrasonic transducer elements arranged in a first direction; and the driving device may rotate the transducer on a plane parallel to the surface of the biological body in contact with the ultrasonic probe.

The driving device may be a motor for conveying a driving power to a rack or a wire integrally movable with the transducer.

The driving device may swing the transducer around a center of swing which is a fulcrum shaft extending in a direction parallel to a surface of the biological body in contact with the ultrasonic probe to change an angle at which the ultrasonic wave is to be transmitted.

The driving device may be a motor having a rotation shaft connected to the fulcrum shaft.

The driving device may change the position of the transducer in a plurality of directions among a first direction parallel to the surface of the biological body, a second direction which is parallel to the surface of the biological body and is perpendicular to the first direction, a third direction which is perpendicular to both of the first direction and the second direction, a first rotation direction having an axis extending along the first direction as the center of rotation, a second rotation direction having an axis extending along the second direction as the center of rotation, and a third rotation direction having an axis extending along the third direction as the center of rotation.

The driving device may include a plurality of actuators each for generating a driving power for moving the transducer and a plurality of links; and the driving power generated by the plurality of actuators may be conveyed to the transducer via the plurality of links.

The driving device may include a parallel link mechanism.

The transducer may be set in a bag portion filled with an acoustic coupling liquid.

An ultrasonic diagnostic apparatus according to the present invention comprises an ultrasonic probe including a transducer for transmitting an ultrasonic wave and receiving the ultrasonic wave reflected by a tissue of a biological body, and a driving device for changing a position of the transducer; a probe control section for controlling the driving device to change at least one of a direction and a position at which the transducer is to transmit the ultrasonic wave; a transmission section for causing the transducer to transmit the ultrasonic wave a plurality of times in accordance with the position of the transducer; a receiving section for receiving the ultrasonic wave reflected by a blood vessel repeatedly using the transducer to generate a plurality of receiving signals; an intensity information generation section for generating intensity information on a distribution of an intensity of the reflected ultrasonic wave based on the plurality of receiving signals; and a determination section for specifying a position of the transducer at which the intensity of the reflected ultrasonic wave is maximum, based on the intensity information. The ultrasonic diagnostic apparatus transmits the ultrasonic wave at the specified position and calculates a property value of the blood vessel.

The intensity information generation section may generate intensity information which represents a distribution of an intensity of the reflected ultrasonic wave received by each of receiving sections A and B discrete from each other on the transducer; the determination section may determine whether or not the intensity information provided by the receiving section A and the intensity information provided by the receiving section B represent a maximum value at the same time; and when the intensity information provided by the receiving section A and the intensity information provided by the receiving section B do not represent the maximum value at the same time, the probe control section may rotate the transducer at a prescribed angle on a plane parallel to the surface of the biological body.

When the intensity information provided by the receiving section A and the intensity information provided by the receiving section B do not represent the maximum value at the same time, the probe control section may rotate the transducer such that the transducer is parallel to the blood vessel based on the position of the transducer at which the intensity information provided by the receiving section A represents the maximum value, the position of the transducer at which the intensity information provided by the receiving section B represents the maximum value, and a distance between the receiving sections A and B.

Until the determination section determines that the intensity information provided by the receiving section A and the intensity information provided by the receiving section B represent the maximum value at the same time, the probe control section may rotate the transducer by the prescribed angle repeatedly.

After the determination section determines that the intensity information provided by the receiving section A and the intensity information provided by the receiving section B represent the maximum value at the same time, the determination section may specify the position of the transducer at which the intensity of the reflected ultrasonic wave is maximum.

The ultrasonic diagnostic apparatus may further comprise a control section for instructing the transmission section and the receiving section to respectively transmit and receive the ultrasonic wave; and a calculation section for calculating the property value of the blood vessel based on the ultrasonic wave received by the receiving section. When the transducer is located at the position specified by the determination section, the control section may instruct the transmission section and the receiving section to respectively transmit and receive the ultrasonic wave.

The ultrasonic diagnostic apparatus may further comprise an operation section for outputting a control signal for changing the position of the transducer. The probe control section may change the position of the transducer based on the control signal.

The probe control section may receive the control signal from the operation section via a network.

Another ultrasonic diagnostic apparatus according to the present invention comprises an ultrasonic probe for transmitting an ultrasonic wave using a transducer including a plurality of transducer elements arranged in a length direction thereof and receiving the ultrasonic wave reflected by a tissue of a biological body; a transmission section for causing the transducer to transmit an ultrasonic wave in succession from different positions along the length direction; a receiving section for receiving the ultrasonic wave reflected by a blood vessel repeatedly using the transducer to generate a plurality of receiving signals; an intensity information generation section for generating intensity information on a distribution of an intensity of the reflected ultrasonic wave based on the plurality of receiving signals; and a determination section for specifying a position along the length direction at which the intensity of the reflected ultrasonic wave is maximum, based on the intensity information. The ultrasonic diagnostic apparatus transmits the ultrasonic wave at the specified position and calculates a property value of the blood vessel.

The ultrasonic probe may include a driving device for changing a position of the transducer within the ultrasonic probe; the ultrasonic diagnostic apparatus may further includes a probe control section for controlling the driving device to change a position from which the transducer transmits the ultrasonic wave; and a calculation section for calculating the property value of the blood vessel; and after the calculation section measures the property value of the blood vessel at the specified position, the probe control section may control the driving device to move the transducer in a direction which is perpendicular to a direction in which the ultrasonic wave is transmitted and is also perpendicular to the length direction.

The transmission section may cause the post-movement transducer to transmit an ultrasonic wave in succession from different positions along the length direction.

A still another ultrasonic diagnostic apparatus according to the present invention is for performing a measurement on a test subject by contacting an ultrasonic probe to the test subject including a blood vessel wall of an artery, in which the ultrasonic probe includes a transducer having a plurality of transducer elements arranged one-dimensionally and the transducer is movable within the ultrasonic probe in a direction perpendicular to the direction in which the transducer elements are arranged, and comprises a transmission section for driving the transducer of the ultrasonic probe to transmit first and second transmission waves to a measurement area of the test subject, the measurement area including the blood vessel wall of the artery; a probe control section for controlling a position of the transducer in the direction perpendicular to the direction in which the transducer elements are arranged; a receiving section for receiving, using the ultrasonic probe, reflected waves respectively obtained by the first and second transmission waves being reflected by the test subject to generate first and second receiving signals; a measurement position determination section for controlling the probe control section to measure an intensity of the first receiving signal while changing the position of the transducer at each cardiac cycle, estimating a position change of an axis of the artery during one cardiac cycle based on the intensity, and controlling the probe control section such that the position of the transducer changes so as to match the estimated position change; and a calculation section for calculating a shape value of the test subject based on the second receiving signal which is obtained by changing the position of the transducer so as to match the estimated position change.

The transmission section may sequentially drive the plurality of transducer elements to transmit one frame of the second receiving signal repeatedly for a plurality of frames in each cardiac cycle each time the measurement area is scanned by the second transmission wave, and transmit the first transmission wave in each frame.

The measurement position determination section may determine a position of the transducer at which the first receiving signal has a maximum value in each frame, and control the probe control section such that the position of the transducer changes to match the determined position.

The ultrasonic diagnostic apparatus may further comprise a tomogram generation section for generating a signal for B mode image based on amplitude information on the first receiving signal.

Effects of the Invention

According to the present invention, while a property of a blood vessel is measured, the driving device of the ultrasonic diagnostic apparatus moves the transducer based on a control signal from the ultrasonic diagnostic apparatus to change at least one of a direction and a position at which the ultrasonic wave is to be transmitted. The determination section of the ultrasonic diagnostic apparatus specifies a position of the transducer at which the reflection intensity is maximum based on the intensity information representing the intensity of the reflected wave. Owing to this, the positional relationship between the ultrasonic diagnostic apparatus and the blood vessel can be adjusted such that the acoustic line from the ultrasonic transducer passes the center of the cross-section of the blood vessel for measuring the elasticity characteristic.

By calculating the elasticity characteristic of the blood vessel at that position, the elasticity characteristic of the blood vessel can be obtained accurately.

Also according to the present invention, the measurement position determination section controls the probe control section to measure the intensity of the first receiving signal while changing the position of the transducer at each cardiac cycle. Based on the measured intensity, the measurement position determination section also estimates the position change of the axis of the blood vessel during one cardiac cycle and controls the probe control section such that the position of the transducer changes so as to match the estimated position change. Therefore, even where the blood vessel is translated in parallel to the axis thereof, generation of a measurement error caused by the movement of the blood vessel can be suppressed with a relatively simple circuit configuration with no need to analyze the movement of the blood vessel three-dimensionally, and an accurate elasticity characteristic can be found.

BRIEF DESCRIPTION OF THE DRAWINGS

FIGS. 11 (a) and (b) are respectively an isometric view and a plan view showing a physical structure of the ultrasonic probe 13 in Embodiment 1.

FIG. 19 A diagram showing waveforms of reflection intensities detected by the receiving sections A and B, both of which have a maximum value at yo.

FIGS. 20 (a) and (b) show a physical structure of the ultrasonic probe 13 in Embodiment 2.

FIGS. 30 (a) and (b) respectively show an example of a structure of the ultrasonic probe 13 for swinging the case 50 like a pendulum with a relatively upper point K in the case 50 used as a fulcrum, and (c) shows a specific structure of the ultrasonic probe 13.

FIG. 47 (a1) and (a2) are respectively a plan view and a cross-sectional view of a probe 500 ideally located with respect to the blood vessel 3, and (b1) and (b2) are respectively a plan view and a cross-sectional view of a probe 100 located at a position deviated from the center of the blood vessel 3.

FIGS. 50 (a) and (b) illustrate the positional relationship between the blood vessel and a probe for performing a measurement on the blood vessel.

DESCRIPTION OF THE REFERENCE NUMERALS

Figure 1:
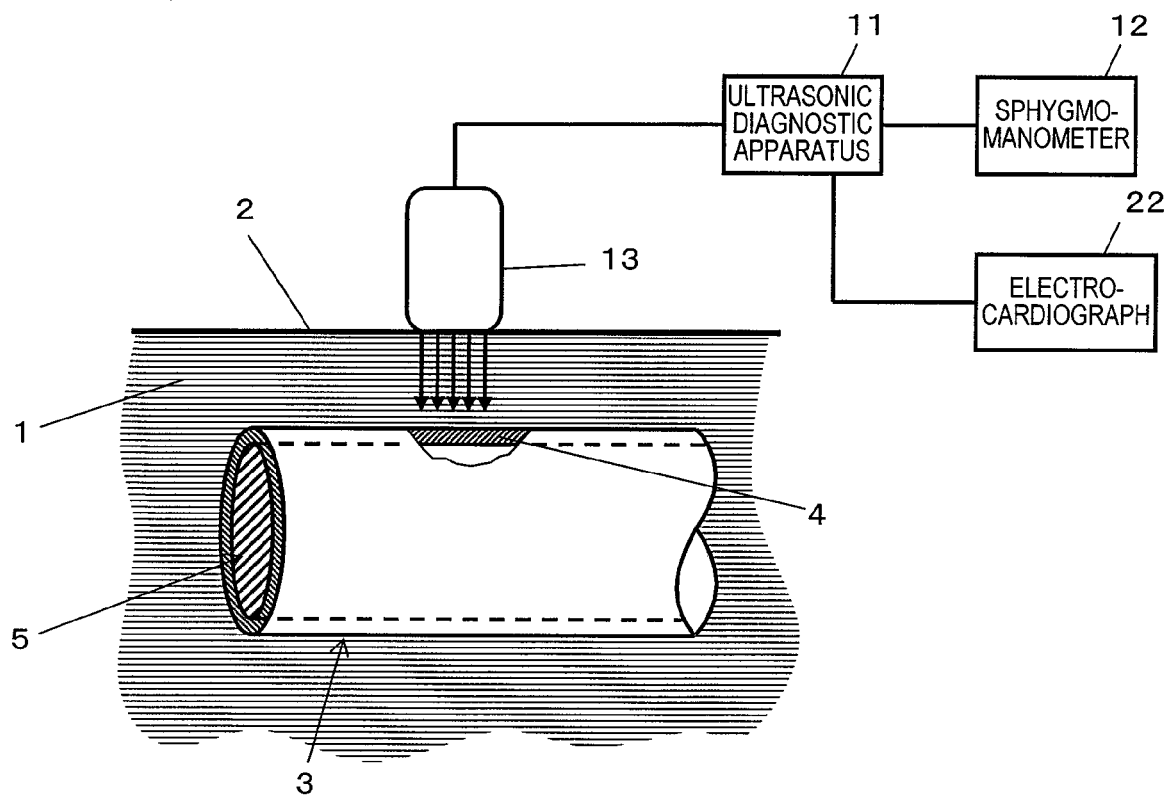
FIG. 1 A block diagram showing a structure for measuring an elasticity characteristic of a blood vessel 3 using an ultrasonic diagnostic apparatus 11.

1 Extravascular tissue
2 Body surface
3 Blood vessel
4 Blood vessel front wall
5 Blood
11 Ultrasonic diagnostic apparatus
12 Sphygmomanometer
13 Ultrasonic probe
14 Transmission section
15 Receiving section
16 Delay time control section
17 Phase detection section
18 Filtering section
19 Calculation section
20 Calculation data storage section
21 Display section
22 Electrocardiograph
23 Intensity information generation section
24 Central position determination section
25 Probe control section
26 Control section
30, 35 Transducer 31 Shape measurement value calculation section
32 Property value calculation section
40 Blood vessel wall
41 ROI
50 Case
110, 112 Rack
111, 113 Motor
121 Link
122 Joint
123 Actuator
124 Movable base
125 Base section
130 Bag portion
131 Acoustic coupling liquid
132 Window section
133 Operation point section

BEST MODE FOR CARRYING OUT THE
INVENTION

Hereinafter, embodiments of an ultrasonic diagnostic apparatus according to the present invention will be described with reference to the attached drawings.

FIG. 1 is a block diagram showing a structure for measuring the elasticity characteristic of the blood vessel 3 using an ultrasonic diagnostic apparatus 11. This structure is common among the embodiments.

An ultrasonic probe 13 is supported so as to be in close contact with a body surface 2 of a test subject and transmits an ultrasonic wave (acoustic line) to the inside of a tissue of a biological body, which encompasses an extravascular tissue 1 and a blood vessel 3, using one or a plurality of ultrasonic transducers. The extravascular tissue 1 is formed of fat, muscle or the like. The transmitted ultrasonic wave is reflected or scattered by the blood vessel 3 or blood 5, and a part thereof returns to the ultrasonic probe 13 and is received as an echo.

The ultrasonic probe 13 has a plurality ultrasonic transducer elements (ultrasonic transducer element group) arranged in an array built therein. Distinctive structures and operations of the ultrasonic probe 13 according to the present invention will be described in the following embodiments. In this section, a basic operation principle of the ultrasonic probe 13 will be described.

Figure 2:
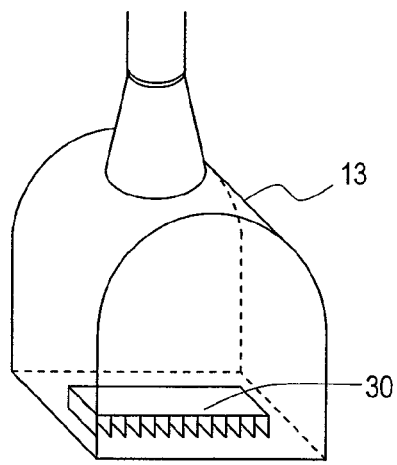
FIG. 2 A diagram showing an ultrasonic transducer element group 30 built in an ultrasonic probe 13.

FIG. 2 shows an ultrasonic transducer element group 30 built in the ultrasonic probe 13. The ultrasonic transducer elements of the ultrasonic transducer element group 30 are, for example, arranged in one direction and form a so-called 1D array transducer. Hereinafter, a unit having the ultrasonic transducer group 30 will be referred to as the "transducer 30".

The transducer 30 is formed of, for example, a piezoelectric element. An ultrasonic wave is transmitted by driving the piezoelectric element, and the piezoelectric element which has received an ultrasonic wave converts the ultrasonic wave into an electric signal. The transducer 30 can sequentially swing the ultrasonic transducer elements to transmit and receive an ultrasonic wave and thus scan a prescribed range. The transducer 30 can also cause phases of the ultrasonic waves from the plurality of ultrasonic transducer elements to overlap one another at a prescribed position (position of a focal point) and receive a signal reflected at the position of the focal point. An example of the latter function is shown in FIG. 3.

Figure 3:
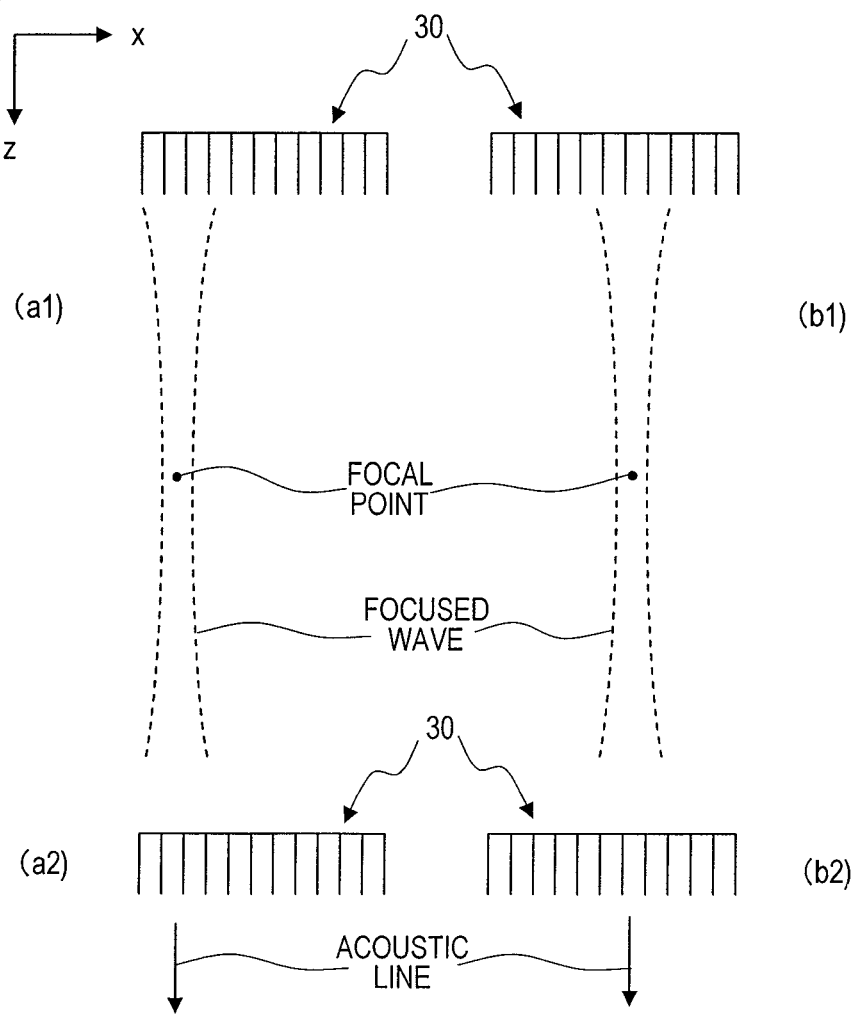
FIG. 3 (a1) and (b1) schematically show a focused ultrasonic wave when a focal point is formed using a plurality of ultrasonic transducer elements arranged in an x direction, and (a2) and (b2) are simplified views of the focused ultrasonic wave.

Portions (a1) and (b1) of FIG. 3 each schematically show a focused ultrasonic wave when a focal point is formed using a plurality of ultrasonic transducer elements arranged in an x direction. The focused ultrasonic wave has a prescribed width as shown here and has a focal point at a prescribed depth in a z-axis direction.

In this specification, the figures may be occasionally simplified. For example, the focused ultrasonic wave shown in portion (a1) of FIG. 3 may be represented by only a central axis of an ultrasonic beam, which is represented as an "acoustic line" in portion (a2) of FIG. 3. The focused ultrasonic wave shown in portion (b1) of FIG. 3 may be represented by only a central axis of an ultrasonic beam, which is represented as an "acoustic line" in portion (b2) of FIG. 3.

Figure 4:
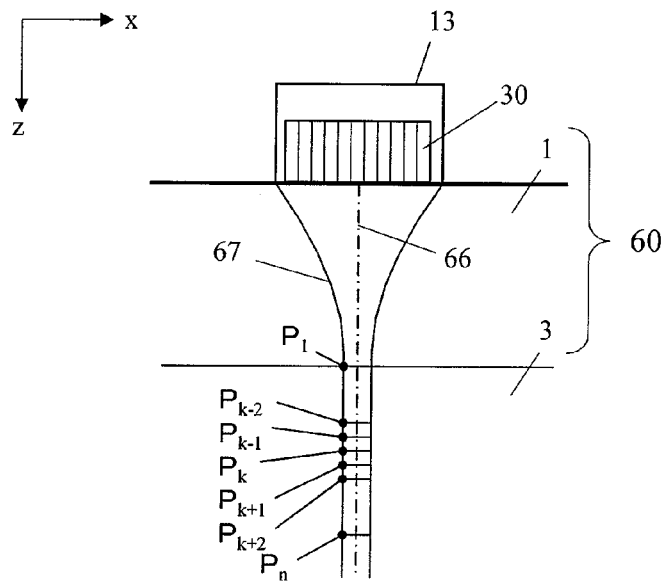
FIG. 4 A diagram schematically showing an ultrasonic beam propagating in a tissue of a biological body.

FIG. 4 schematically shows an ultrasonic beam propagating in a tissue of a biological body. An ultrasonic wave which is output from the ultrasonic probe 13 progresses in the z-axis direction as an ultrasonic beam 67 having a certain finite width and propagates in the extravascular tissue 1 and the blood vessel 3, which are tissues of the biological body. During the propagation, the ultrasonic wave is reflected or scattered by the extravascular tissue 1 and the blood vessel 3. A part thereof returns to the ultrasonic probe 13 and is received as a reflected ultrasonic wave. The reflected ultrasonic wave is detected as a time-series signal. A time-series signal obtained as a result of the reflection by a tissue closer to the ultrasonic probe 13 is located closer to the origin of a time axis. The width of the ultrasonic beam 67 (beam diameter) can be controlled by changing the delay time.

As described above, the reflected ultrasonic wave is generated by the estravascular tissue 1, the blood vessel 3 and the blood 5. A plurality of measurement target positions $P_n$ ($P_1$, $P_2$, $P_3$, $P_k$, ... $P_n$; n is a natural number of 3 or greater) on a blood vessel front wall, which are located on an acoustic line 66, are arranged at a certain interval and sequentially numbered as $P_1$, $P_2$, $P_3$, $P_k$, ... $P_n$ from the one closest to the ultrasonic probe 13. It is assumed that a coordinate axis in which a top portion of FIG. 4 has positive values and a bottom portion of FIG. 4 has negative values is provided in a depth direction, and the measurement target positions $P_1$, $P_2$, $P_3$, $P_k$, ... $P_n$ respectively have coordinates $Z_1$, $Z_2$. $Z_3$, $Z_k$ ... $Z_n$. With this assumption, an ultrasonic wave reflected at the measurement target position $P_k$ is located at $t_k=2Z_k/c$ on the time axis. Herein, c represents the sonic velocity of the ultrasonic wave in the tissue of the biological body. The reflected wave signal (time-series signal) is used as information representing the state at the measurement target position.

The ultrasonic diagnostic apparatus 11 transmits an ultrasonic wave to the blood vessel 3 and obtains a reflected wave signal before measuring the properties of the blood vessel 3 such as the elasticity characteristic or distortion of the blood vessel. Then, the ultrasonic diagnostic apparatus 11 adjusts the positional relationship between the ultrasonic probe 13 or the transducer 30 and the blood vessel 3 by a method described later in Embodiment 1 or 2, such that an ultrasonic wave (acoustic line) transmitted from the transducer 30 of the ultrasonic probe 13 passes the center of a cross-section of the blood vessel 3.

When the adjustment of the positional relationship is completed, the ultrasonic diagnostic apparatus 11 transmits an ultrasonic wave again to the inside of the tissue of the biological body to perform analyses and calculations on a receiving signal by the received echo. The ultrasonic diagnostic apparatus 11 uses, for example, the method disclosed in Patent Document No. 1 to determine a position of the target at an instant by the constrained least squares method using both the amplitude and the phase of the detection signal, and performs highly precise (the measuring error of the position change amount is about ±0.2 microns) phase tracking. Owing to this, the ultrasonic diagnostic apparatus 11 can obtain the motion information on the extravascular tissue 1 or the blood vessel 3 by measuring, for example, the time-wise change of the position and thickness of a tiny site of a wall of the blood vessel 3 at a sufficient precision.

The ultrasonic diagnostic apparatus 11 is connected to a sphygmomanometer 12. Information on a blood pressure of the test subject obtained by the sphygmomanometer 12 is input to the ultrasonic diagnostic apparatus 11. Using the information on the blood pressure obtained by the sphygmomanometer 12, the elasticity characteristic of the tiny site of the wall of the blood vessel 3 can be found.

The ultrasonic diagnostic apparatus 11 is also connected to an electrocardiograph 22. The ultrasonic diagnostic apparatus 11 receives an electrocardiographic waveform from the electrocardiograph 22 and uses the electrocardiographic waveform as a trigger signal for obtaining measurement data or determining the timing to reset data.

In the following embodiments, examples of finding the elasticity characteristic of the blood vessel using the ultrasonic diagnostic apparatus will be described, but the ultrasonic diagnostic apparatus can measure properties other than the elasticity characteristic of the blood vessel, for example, the distortion of the blood vessel and the like.

Embodiment 1

Hereinafter, an ultrasonic diagnostic apparatus in Embodiment 1 according to the present invention will be described.

Figure 5:
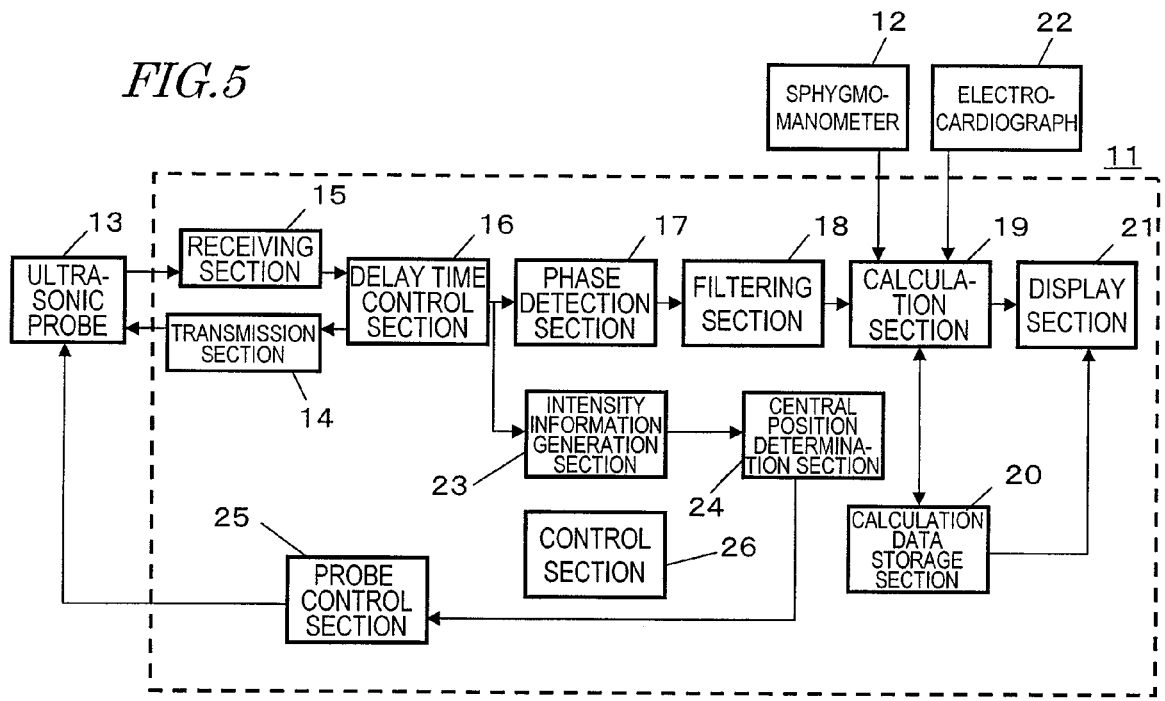
FIG. 5 A block diagram showing an internal structure of the ultrasonic diagnostic apparatus 11.

FIG. 5 is a block diagram showing an internal structure of the ultrasonic diagnostic apparatus 11 in this embodiment.

The ultrasonic diagnostic apparatus 11 includes a transmission section 14, a receiving section 15, a delay time control section 16, a phase detection section 17, a filtering section 18, a calculation section 19, a calculation data storage section 20, a display section 21, an intensity information generation section 23, a central position determination section 24, and a probe control section 25. The ultrasonic diagnostic apparatus 11 also includes a control section 26 formed of a microcomputer or the like in order to control these elements.

Among the elements of the ultrasonic diagnostic apparatus 11, the intensity information generation section 23, the central position determination section 24, and the probe control section 25 are provided mainly in order to adjust the positional relationship between the transducer 30 and the blood vessel such that an ultrasonic wave passes the center of the cross-section of the blood vessel. By contrast, the phase detection section 17, the filtering section 18, the calculation section 19, the calculation data storage section 20, and the display section 21 are provided mainly in order to measure the elasticity characteristic of the blood vessel 3 and display the measurement results. The transmission section 14, the receiving section 15, the delay time control section 16, and the control section 26 are operated both for adjusting the positional relationship between the transducer 30 and the blood vessel and for measuring the elasticity characteristic of the blood vessel.

The ultrasonic diagnostic apparatus 11 shown in FIG. 5 does not include the ultrasonic probe 13. However, the ultrasonic probe 13 may be regarded as an element of the ultrasonic diagnostic apparatus 11 because the ultrasonic probe 13 is indispensable for the operation of the ultrasonic diagnostic apparatus 11.

Hereinafter, a function of each element of the ultrasonic diagnostic apparatus 11 will be described.

The transmission section 14 generates a prescribed driving pulse signal and outputs the driving pulse signal to the ultrasonic probe 13. A transmission ultrasonic wave transmitted from the ultrasonic probe 13 by the driving pulse signal is reflected or scattered by a tissue of the biological body such as the blood vessel 3 or the like, and the generated reflected ultrasonic wave is detected by the ultrasonic probe 13. A frequency of the driving pulse for generating the ultrasonic wave is determined in consideration of the depth of the measurement target and the sonic velocity of the ultrasonic wave, such that the ultrasonic pulses adjacent to each other on the time axis do not overlap.

The receiving section 15 detects the reflected ultrasonic wave using the ultrasonic probe 13, and amplifies the signal obtained by the detection to generate a receiving signal. The receiving section 15 includes an A/D conversion section and thus converts the receiving signal into a digital signal. The transmission section 14 and the receiving section 15 are both structured using an electronic component or the like.

The delay time control section 16 is connected to the transmission section 14 and the receiving section 15, and controls a delay time of the driving pulse signal, which is to be transmitted from the transmission section 14 to the ultrasonic vibration element group of the ultrasonic probe 13. Owing to this, the direction of the acoustic line and the depth of the focal point of the ultrasonic beam of the transmission ultrasonic wave transmitted from the ultrasonic probe 13 are changed. The delay time control section 16 also controls a delay time of the receiving signal received by the ultrasonic probe 13 and generated by the receiving section 15 and thus can change the aperture diameter or the position of the focal point. The output from the delay time control section 16 is input to the phase detection section 17.

The phase detection section 17 detects a phase of the receiving signal delay-time-controlled by the delay time control section 16, and separates the receiving signal into a real part signal and an imaginary part signal. The separated real part signal and imaginary part signal are input to the filtering section 18. The filtering section 18 removes a high frequency component, a reflection component from a site other than the measurement target, a noise component and the like. The phase detection section 17 and the filtering section 18 may be structured either by software or hardware. As a result of the above, a phase detection signal corresponding to each of the plurality of measurement target positions set inside the tissue of the blood vessel 3 and including a real part signal and an imaginary part signal is generated.

Figure 6:
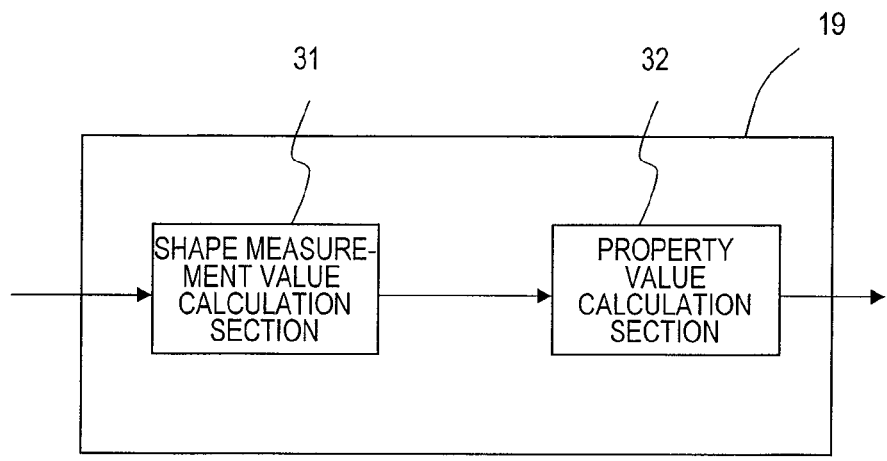
FIG. 6 A block diagram showing an internal structure of a calculation section 19.

The calculation section 19 performs various calculations. FIG. 6 shows a functional block for realizing calculation processing of the calculation section 19. The calculation section 19 includes a shape measurement value calculation section 31 and a property value calculation section 32. An electrocardiographic waveform obtained from the electrocardiograph 22 is input to the calculation section 19 and used as a trigger signal for obtaining measurement data or determining the timing to reset data. In the case where the electrocardiograph 22 is used only for this purpose, the electrocardiograph 22 may be replaced with another biological signal detection means, i.e., a phonocardiograph or a sphygmograph, and a phonocardiographic waveform or a sphygmographic waveform may be used as a trigger signal instead of the electrocardiographic waveform.

The shape measurement value calculation section 31 finds a position change amount (time-wise change amount of the position) of each of the plurality of measurement target positions set inside the tissue of the blood vessel 3, using the real part signal and the imaginary part signal of the phase detection signal. The position change amount may also be found by finding the motion velocity of each measurement target position (tracking position) and integrating the motion velocity.

By finding a difference between the position change amounts of any two positions selected from the plurality of position change amounts, a change amount of the thickness between the two points can be found. In the case where initial values of the two positions or an initial value of the difference between the position change amounts of the two points is given, the thickness between the two points can be found.

The two points which define the thickness or the thickness change amount do not need to match the measurement target positions set inside the tissue of the blood vessel 3. For example, a central position of the plurality of measurement target positions may be used. In this case, it is preferable to use an average of the position change amounts of the plurality of measurement target positions, the central position thereof has been found. In the case where a plurality of measurement target positions are used, the position representative of the plurality of measurement target positions and the position change amount thereof may be found by simply finding an average thereof or by performing weighting. It is acceptable to find two positions and the position change amounts thereof based on the plurality of measurement target positions.

The property value calculation section 32 calculates a maximum thickness change amount from a difference between a maximum value and a minimum value of the found thickness change amount, and finds the elasticity characteristic of the tissue located between the two points from the maximum thickness change amount and the blood pressure data obtained by the sphygmomanometer 12.

Specifically, the property value calculation section 32 uses a thickness Hk of a target tissue Tk (the value at the minimum blood pressure), a difference Δhk between the maximum value and the minimum value of a thickness change amount Dk(t) of the target tissue, and a pulse pressure Δp as a difference between a minimum blood pressure and a maximum blood pressure to represent an elasticity characteristic Ek, which shows the stiffness of the blood vessel in the target tissue Tk, by the following expression. Ek is occasionally referred to as the "elasticity" or the "elasticity coefficient".

$$Ek = \Delta p / (\Delta hK / Hk)$$

The elasticity characteristic of one point interposed between any two points may be found. It should be noted that because the ultrasonic probe 13 used in this embodiment includes a plurality of ultrasonic transducer elements arranged in an array, it is possible to find the elasticity characteristic of all the sites in an arbitrary area of the cross-section.

The property value calculation section 32 is not provided only for finding the elasticity characteristic, and may find, for example, a distortion as one of the properties of the blood vessel by calculating Δhk/H.

Referring to FIG. 5 again, the display section 21 maps the found maximum thickness change amount, distortion or elasticity characteristic of the tissue of the biological body and displays a spatial distribution image of each cardiac cycle, which represents a spatial distribution of the shape measurement value or the property measurement value. The spatial distribution image may be one-dimensional, two-dimensional or three-dimensional. In the case where the spatial distribution image is displayed with a color or a gradation level corresponding to the shape measurement value or the property measurement value, the measurement results are easy to understand.

In this case, an operator can determine an area for which the shape measurement value or the property measurement value is to be found, by specifying such an area on the display section 21. This area is referred to as an "ROI" (abbreviation of Region Of Interest). An ROI is displayed for allowing the operator to specify an area for which the measurement value is to be found. The operator can freely set such an area via an interface section (not shown) of the ultrasonic diagnostic apparatus 11 while checking the size or position of such an area on the display section 21.

Figure 7:
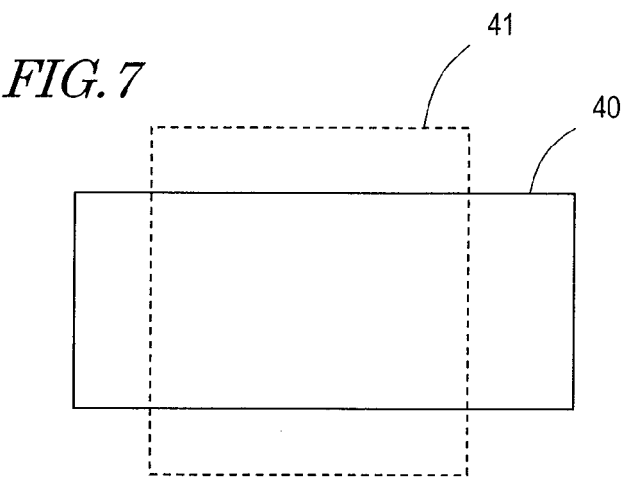
FIG. 7 A schematic view of a blood vessel wall 40 and an ROI 41 displayed on a display section 21.
Figure 8:
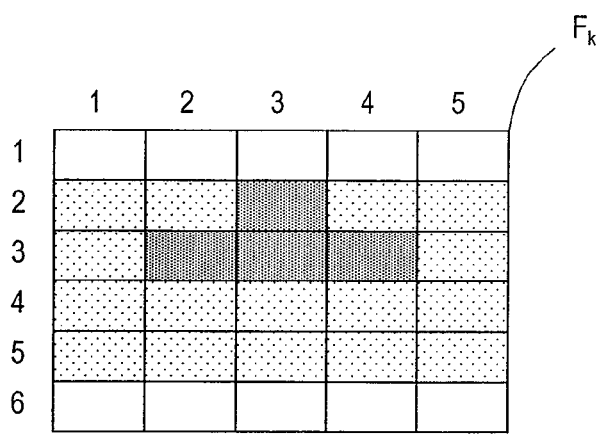
FIG. 8 A diagram showing an elasticity characteristic of an area of the blood vessel wall 40 defined by the ROI 41.

FIG. 7 schematically shows a blood vessel wall 40 and an ROI 41 shown on the display section 21. An area defined by the ROI 41 includes tissues other than the blood vessel wall 40. An image of the blood vessel wall 40 is obtained by, for example, modulating the receiving signal at a luminance corresponding to the amplitude intensity, aside from the above-described calculation. FIG. 8 shows the elasticity characteristic of the area in the blood vessel 41 defined by the ROI 41. In the area defined by the ROI 41, for example, image data $f(k)_{11}$ to $f(k)_{65}$ mapped in 6 rows×5 columns is arranged. Image data $f(k)_{11}$ to $f(k)_{65}$ form a spatial distribution image Fk. As described above, the image data $f(k)_{11}$ to $f(k)_{65}$ is a shape measurement value representing the maximum thickness change amount or the like of the tissue of the biological body or a property value representing the distortion, the elasticity characteristic or the like.

The data on the position change amount, the thickness change amount, the elasticity characteristic or the like calculated by the calculation section 19 is stored in the calculation data storage section 20 shown in FIG. 5 and can be read at any time. The data on the position change amount, the thickness change amount, the elasticity characteristic or the like calculated by the calculation section 19 is input to the display section 21 and can be visualized as a two-dimensional image. In addition, by connecting the display section 21 and the calculation data storage section 20 to each other, any of various stored data can be displayed by the display section 21 at any time. It is preferable that the various data calculated by the calculation section 19 is output to the display section 21 and also to the storage section 20, so that the data is stored for later use while being displayed in real time. Alternatively, the data calculated by the calculation section 19 may be output to either one of the display section 21 and the storage section 20.

The intensity information generation section 23 measures an intensity (reflection intensity) of the reflected wave based on the amplitude of the receiving signal delay-time-controlled by the delay time control section 16, and generates intensity information representing a distribution of the reflection intensity. As described later, in this embodiment, an x axis of the transducer 30 (for example, FIG. 4) and an axis of the blood vessel 3 along a direction in which the blood vessel 3 extends (hereinafter, such an axis of the blood vessel 3 will be referred to as the "longer axis") are located substantially parallel to each other. In this state, the transducer 30 moves within the ultrasonic probe 13 while generating an ultrasonic wave. The direction in which the transducer 30 moves is perpendicular to the x axis on a plane parallel to the body surface 2. The intensity information generation section 23 measures the reflection intensity obtained as the transducer 30 moves and generates the intensity information.

The central position determination section 24 specifies a position of the transducer 30 in the ultrasonic probe 13 at which the maximum reflection intensity is obtained, based on the intensity information.

The probe control section 25 outputs a control signal for controlling the movement of the transducer 30 within the ultrasonic probe 13. For example, the probe control section 25 controls the start and finish of the movement, the moving direction and the moving velocity of the transducer 30 based on an instruction from the control section 26. The probe control section 25 also moves the transducer 30 to a position specified by the central position determination section 24.

Hereinafter, with reference to FIG. 9 and FIG. 10, a principle of processing of adjusting the positional relationship between the transducer 30 and the blood vessel 3 will be described. This processing causes an ultrasonic wave (acoustic line) transmitted from the transducer 30 to pass the center of the cross-section of the blood vessel, and so allows the elasticity characteristic of the blood vessel 3 to be accurately measured.

In this embodiment, the x axis of the transducer 30 (for example, FIG. 4) and the longer axis of the blood vessel 3 are located substantially parallel to each other.

Figure 9:
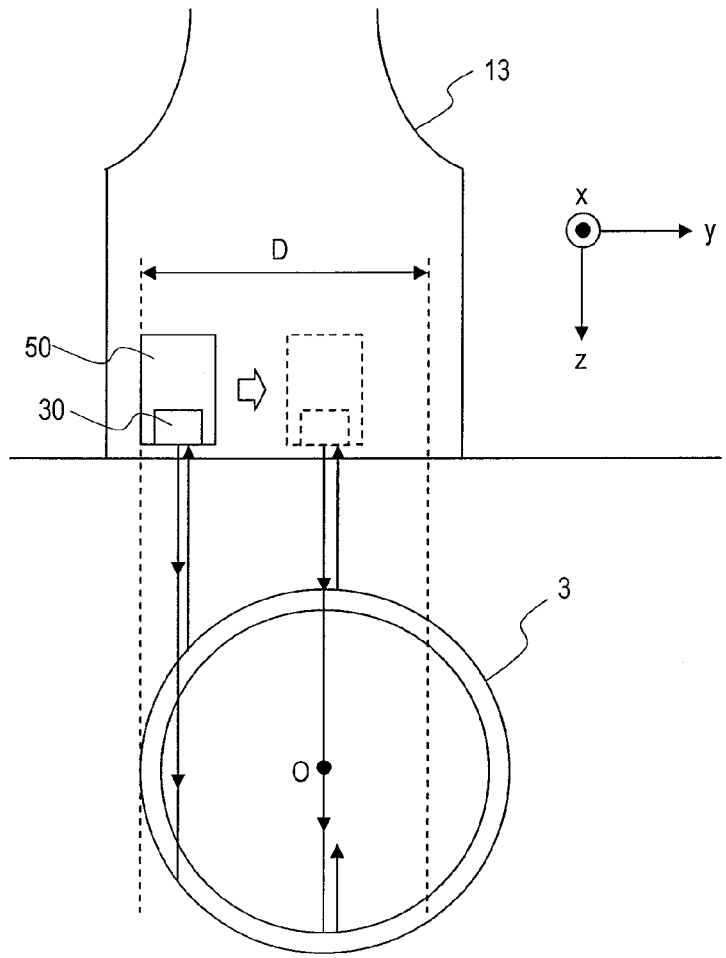
FIG. 9 A diagram showing the transducer 30 moving within the ultrasonic probe 13 while generating an ultrasonic wave.

FIG. 9 shows the transducer 30 moving within the ultrasonic probe 13 while generating an ultrasonic wave. The transducer 30 is accommodated in a case 50, and the transducer 30 and the case 50 move in a y-axis direction shown here. A movable range of the transducer 30 and the case 50 is represented with "D". While the transducer 30 and the case 50 are moving, the position of the ultrasonic probe 13 is fixed.

Based on a control signal from the probe control section 25, the transducer 30 starts transmitting an ultrasonic wave in the z-axis direction at the position of the left end of the movable range D and moves in the y-axis direction while transmitting the ultrasonic wave. When reaching the right end of the movable range D, the transducer 30 stops transmitting the ultrasonic wave. It is not necessary that the transmission of the ultrasonic wave and the movement in the y-axis direction are performed at the same time. It is acceptable that the transducer 30 moves in the y-axis direction, stops and transmits the ultrasonic wave at that position, and then moves again in the y-axis direction.

Figure 10:
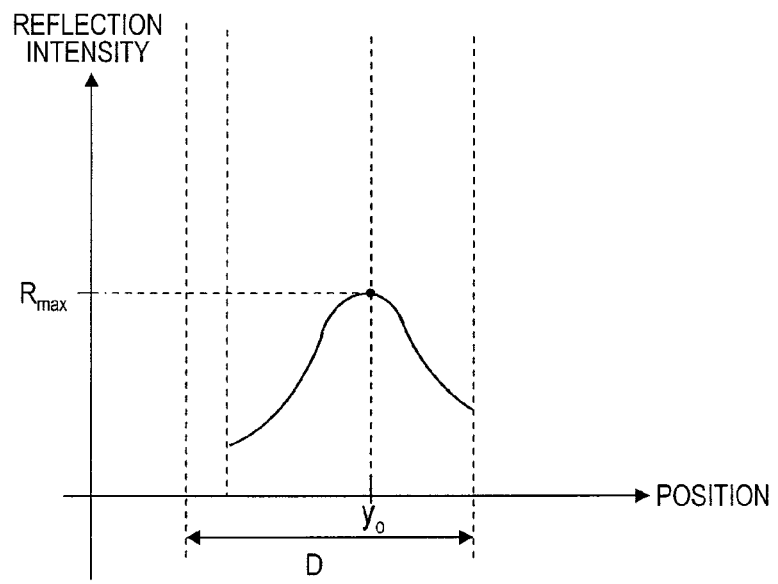
FIG. 10 A diagram showing a reflection intensity of a reflected ultrasonic wave provided by an intensity information generation section 23 while the transducer 30 moves.

FIG. 10 shows a distribution of the reflection intensity of the reflected ultrasonic wave generated by the intensity information generation section 23 as the transducer 30 moves. The horizontal axis represents the position of the transducer 30, and the vertical axis represents the reflection intensity. When a reflection intensity in the movable range D is obtained, the central position determination section 24 specifies a position yo of the transducer 30 at which the maximum reflection intensity Rmax is obtained.

The position yo specified by the central position determination section 24 corresponds to the position at which the transmission ultrasonic wave passes the center of the cross-section of the blood vessel 3. The reason for this is as follows. As the position passed by the transmission wave is farther from the center of the cross-section, the angle at which the transmission wave is reflected by an outer wall and an inner wall of the blood vessel 3 is closer to 90 degrees with respect to the direction of incidence and therefore the detected intensity of the reflected wave from the blood vessel 3 is lower. By contrast, as the position passed by the transmission ultrasonic wave is closer to the center o of the cross-section, the angle at which the ultrasonic wave is reflected by the outer wall and the inner wall of the blood vessel 3 is closer to the direction of incidence and therefore the detected intensity of the reflected wave from the blood vessel 3 is higher. When the transmission ultrasonic wave passes the center o of the cross-section, the direction of incidence and the direction of reflection of the ultrasonic wave match each other at the outer wall and the inner wall of the blood vessel 3 and therefore the detected intensity of the reflected wave is maximum. For this reason, it is considered that the position of the transducer 30 at which the reflection intensity is maximum is the position at which the transmission ultrasonic wave passes the center o of the cross-section.

After the position yo is specified, the probe control section 25 can the transducer 30 to the position yo and fixes the transducer 30 at the position yo, and then measure the elasticity characteristic of the blood vessel 3.

Portions (a) and (b) FIG. 11 show a physical structure of the ultrasonic probe 13 in this embodiment. Portion (a) of FIG. 11 is an isometric view, and portion (b) of FIG. 11 is a plan view. The ultrasonic probe 13 includes a rack 110 and a motor 111. The rack 110 is a flat plate-like rod including teeth, and is physically coupled with the case 50. A rotation shaft of the motor 111 is provided with a pinion, which is engaged with the teeth of the rack 110. By the rotation of the motor 111, the case 50 moves in the y-axis direction together with the rack 110. This realizes the movement of the transducer 30 shown in FIG. 9. The supply of an electric power for rotating the motor 111 and the rotation rate and the rotation time period of the motor 111 corresponding to the moving distance in the y-axis direction are controlled by the probe control section 25.

Figure 12:
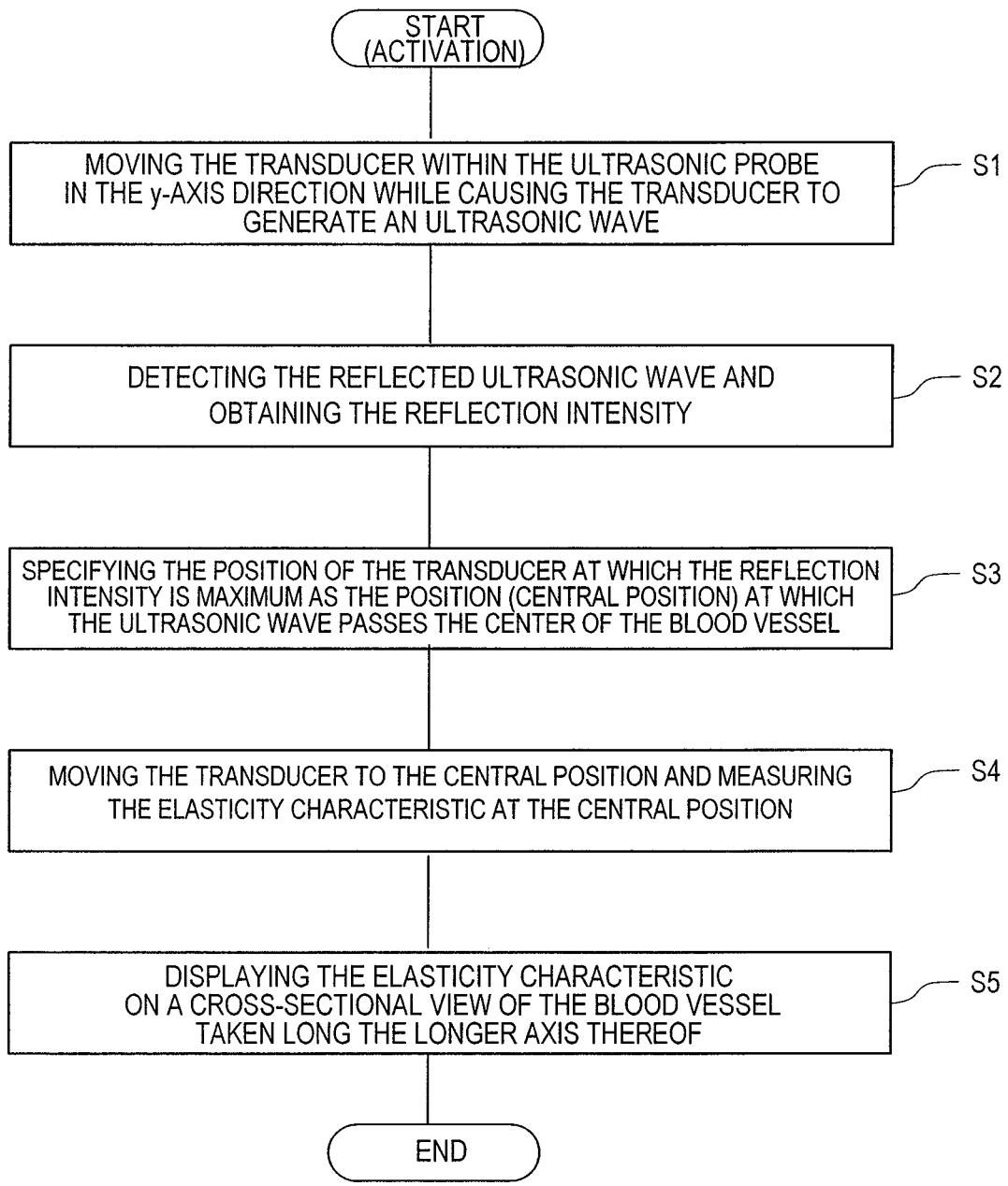
FIG. 12 A flowchart showing a processing procedure of measuring the elasticity characteristic of the blood vessel 3 executed by the ultrasonic diagnostic apparatus 11 in Embodiment 1.

FIG. 12 is a flowchart showing a processing procedure of measuring the elasticity characteristic of the blood vessel 3 executed by the ultrasonic diagnostic apparatus 11 in this embodiment.

In step S1, when the probe control section 25 sends a control signal to the ultrasonic probe 13, the transducer 30 moves in the y-axis direction within the ultrasonic probe 13 while generating an ultrasonic wave. In step S2, the intensity information generation section 23 repeatedly detects the reflected ultrasonic wave as the transducer 30 moves, and obtains the reflection intensity. By, for example, one reciprocating movement of the transducer 30 in the movable range provides a reflection intensity distribution.

In step S3, the central position determination section 24 specifies the position of the transducer 30 at which the reflection intensity is maximum as the position (central position) at which the ultrasonic wave passes the center o of the blood vessel.

In step S4, when the probe control section 25 moves the transducer 30 to the central position, the control section 26 instructs the elasticity characteristic of the blood vessel 3 to be measured at the central position. Based on this instruction, the phase detection section 17, the filtering section 18, the calculation section 19 and the calculation data storage section 20 operate to measure the elasticity characteristic of the blood vessel 3.

In step S5, the display section 21 displays the cross-section along the longer axis of the blood vessel and also displays the elasticity characteristic measured by the calculation section 19 as being superimposed on the cross-sectional view thereof.

By the processing of steps S1 through S3, the position of the transducer 30 at which the reflection intensity is maximum is specified as the central position, and the elasticity characteristic of the blood vessel 3 is measured at the central position. Therefore, the distortion of the blood vessel can be accurately measured, and the elasticity characteristic can be accurately measured.

In this embodiment, the transducer 30 is moved within the ultrasonic probe 13 in a prescribed axial direction, and thus the center of the cross-section of the blood vessel 3 is specified. Alternatively, a structure with which the transducer 30 is not moved in a prescribed axial direction may be adopted.

Figure 13:
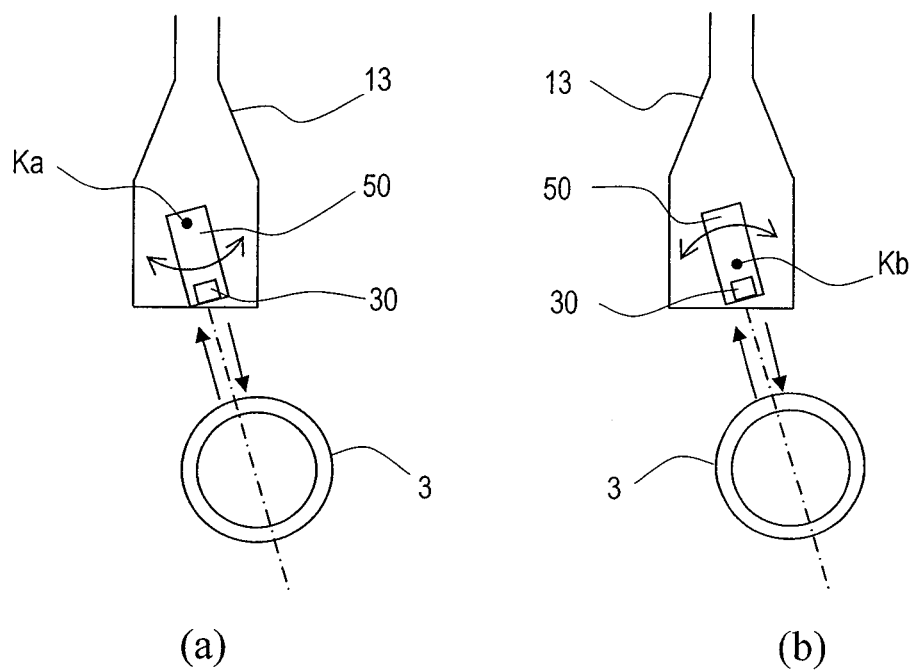
FIGS. 13 (a) and (b) respectively show examples of a structure of the ultrasonic probe 13 for moving a case 50 like a pendulum with points Ka and Kb used as a fulcrum.

For example, portion (a) of FIG. 13 shows an example of a structure of the ultrasonic probe 13 in which the case 50 is swung like a pendulum with a relatively upper point Ka in the case 50 used as a fulcrum shaft. Portion (b) of FIG. 13 shows an example of a structure of the ultrasonic probe 13 in which the case 50 is swung like a pendulum with a relatively lower point Kb in the case 50 used as a fulcrum shaft. In either example, the fulcrum shaft is parallel to the body surface, and the rotation shaft of the motor matches the fulcrum Ka or Kb. It should be noted that the rotation shaft of the motor does not need to match the fulcrum Ka or Kb. For example, the rotation of the motor may be conveyed to the fulcrum Ka or Kb via a conveyance mechanism such as a gear, a belt or the like. Owing to such a structure, the transmission direction of the ultrasonic wave transmitted from the transducer 30 can be changed. In the example of portion (b) of FIG. 13, the movable range (movable angle) corresponding to the movable range D in FIG. 9 is from −180 degrees to +180 degrees. In the example of portion (a) of FIG. 13, the movable range (movable angle) is smaller than that in the example of portion (b) of FIG. 13.

In the case where the ultrasonic probe 13 having such a structure is used, the elasticity characteristic of the blood vessel 3 at the central position can be measured by specifying the rotation angle at which the ultrasonic wave transmitted from the transducer 30 passes the center of the cross-section of the blood vessel 3 based on the maximum reflection intensity. According to this structure, the blood vessel 3 does not need to be present right below the ultrasonic probe 13. Therefore, even a user who is not accustomed to the ultrasonic probe 13 and so cannot locate the ultrasonic probe 13 on the blood vessel 3 can measure the elasticity characteristic accurately.

A structure in which the transducer 30 is moved parallel to the body surface to change the position from which the ultrasonic wave is to be transmitted (FIG. 11, etc.), and a structure in which the transducer 30 is swung like a pendulum to change the angle at which the ultrasonic wave is to be transmitted (FIG. 13), may be combined together. By such a combination, the range to which the ultrasonic wave can be transmitted is widened to enlarge the measurable range. In other words, the tolerable range for the position of the body surface to which the ultrasonic probe 13 is applied is enlarged.

In the above embodiment, the central position at which the ultrasonic wave passes the center of the cross-section of the blood vessel 3 is specified using the maximum reflection intensity. The central position can be specified without using the maximum reflection intensity.

Figure 14:
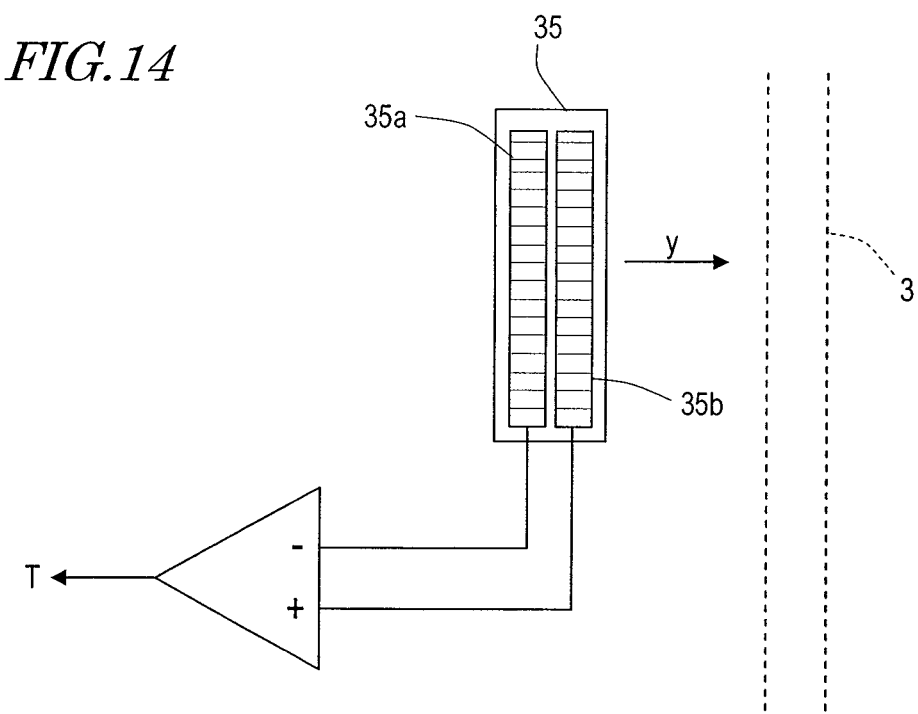
FIG. 14 A diagram showing a transducer 35 as a modification of the transducer 30.

FIG. 14 shows a transducer 35, which is a modification of the transducer 30. The transducer 35 is a so-called 1.5D array transducer and includes two ultrasonic transducer element groups 35a and 35b, each of which is provided in a line. The ultrasonic transducer element groups 35a and 35b are arranged along the moving direction thereof within the ultrasonic probe 13 (y-axis direction).

Using the transducer 35, the central position can be specified based on a difference T between a reflection intensity detected by the ultrasonic transducer element group 35a and a reflection intensity detected by the ultrasonic transducer element group 35b by the following principle.

Figure 15:
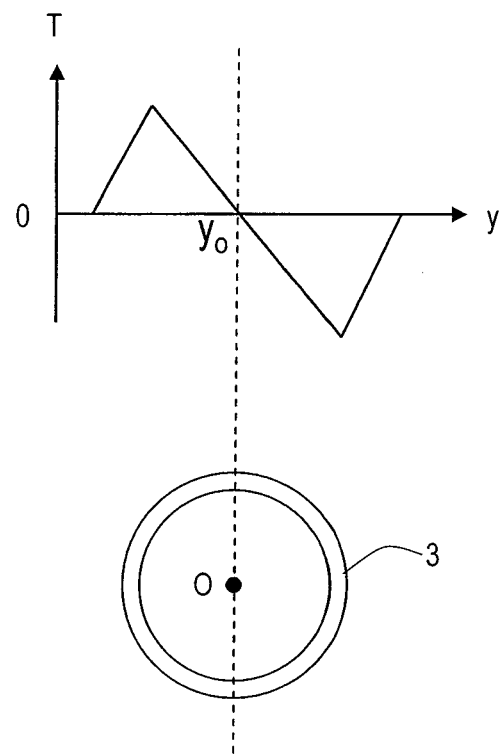
FIG. 15 A diagram showing the relationship between a moving distance y of the transducer 35 in a y-axis direction and a difference T between a reflection intensity detected by an ultrasonic transducer element group 35a and a reflection intensity detected by an ultrasonic transducer element group 35b.

FIG. 15 shows the relationship between a moving distance y of the transducer 35 in the y-axis direction and the difference T between the reflection intensity detected by the ultrasonic transducer element group 35a and the reflection intensity detected by the ultrasonic transducer element group 35b. When the transducer 35 moves in the y-axis direction shown in FIG. 14 to approach the blood vessel 3, the reflection intensity detected by the ultrasonic transducer element group 35b starts increasing. When the ultrasonic transducer element group 35a is not on the blood vessel 3, the reflection intensity from the blood vessel 3 detected by the ultrasonic transducer element group 35a is 0. Therefore, the difference T of the outputs gradually increases.

When the ultrasonic transducer element group 35a reaches the blood vessel 3, the reflection intensity detected by the ultrasonic transducer element group 35a starts increasing and so the output difference T gradually decreases. When the outputs from the ultrasonic transducer element groups 35a and 35b become equal to each other, the output difference T becomes 0. While the output difference T is 0, the ultrasonic transducer element groups 35a and 35b are located symmetrically with respect to the central axis of the blood vessel 3 as seen from the direction shown in FIG. 14. Therefore, the position of the ultrasonic transducer 35 in this state corresponds to the central position.

With the method of determining the central position based on the difference between the reflection intensities using the transducer 35, a peak of the reflection intensity does not need to be detected unlike with the method of determining the maximum intensity shown in FIG. 10. Therefore, the processing time period is shortened. Before the transducer 35 is moved, the sign of the signal may be checked and it may be defined that, for example, when the signal is positive, the transducer 35 is located left to the blood vessel 3 whereas when the signal is negative, the transducer 35 is located right to the blood vessel 3. With such a definition, it can be found whether the transducer 35 is located left or right to the blood vessel 3. In this embodiment, the difference between the reflection intensities of the ultrasonic transducer element groups 35a and 35b is calculated by the intensity information generation section 23.

As the ultrasonic probe 13 used for the method for determining the central position shown in FIG. 14 and FIG. 15, the ultrasonic probe 13 shown in FIG. 13 may be used.

Among the different types of processing of specifying the central position described above with reference to FIG. 10 and FIG. 15, the processing of obtaining the reflection intensity by moving the transducer 30 within the movable range D is applicable to measure other parameters, for example, the shape or the diameter of the blood vessel 3. This means that the central position of the blood vessel can be measured also based on the measured shape thereof. For using this type of processing to measure the shape of the blood vessel 3, data on the shapes of a plurality of cross-sections is accumulated along the longer axis of the blood vessel 3 to obtain shape data. The shape data may include a thickness change of the front wall of the blood vessel 3, which is caused by the heartbeat. The processing of measuring the diameter of the blood vessel 3 is executed by calculating a difference between the reflected wave from the wall of the blood vessel 3 which is closer to the ultrasonic probe 13 located at the central position described above, and the reflected wave from the wall of the blood vessel 3 which is farther from the ultrasonic probe 13 located at the central position. The above-described processing of obtaining the reflection intensities may be pre-executed when the ultrasonic probe 13 is applied to the body surface of the test subject. In this way, subsequent processing can be executed quickly.

Embodiment 2

Hereinafter, an ultrasonic diagnostic apparatus in Embodiment 2 according to the present invention will be described.

In Embodiment 1, the transducer 30 is moved within the ultrasonic probe 13 to specify the central position at which the ultrasonic wave passes the center of the cross-section of the blood vessel, with a premise that the direction in which the ultrasonic transducer elements are arranged (for example, the x-axis direction in FIG. 4) is substantially parallel to the longer axis of the blood vessel 3.

However, when the apparatus is operated by an unaccustomed user, the arranging direction of the ultrasonic transducer elements may be possibly deviated from the longer axis direction of the blood vessel 3 and it cannot be easily expected that the deviation is quickly corrected.

In this embodiment, an ultrasonic diagnostic apparatus capable of specifying the central position of the blood vessel and accurately measuring the elasticity characteristic even where the arranging direction of the ultrasonic transducer elements is not parallel to the longer axis of the blood vessel will be described.

Hereinafter, with reference to FIG. 16 through FIG. 19, a principle of processing of adjusting the positional relationship between the transducer and the blood vessel will be described. In this embodiment, like in Embodiment 1, the transducer moves within the ultrasonic probe. While the transducer is moving, the position of the ultrasonic probe is fixed on the epidermis of the test subject.

Figure 16:
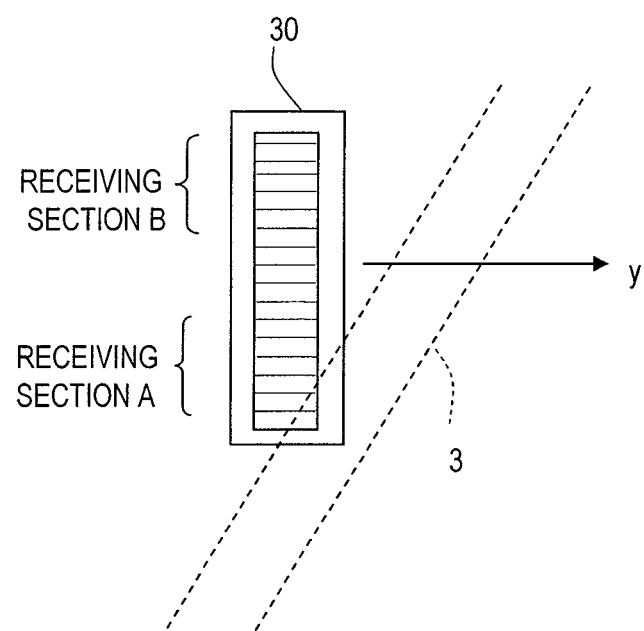
FIG. 16 A diagram showing an example in which the transducer 30 is not located parallel to the blood vessel 3.

FIG. 16 shows an example in which the transducer 30 and the blood vessel 3 are not located parallel to each other. It is assumed that when the transducer 30 and the blood vessel 3 are in the positional relationship shown here, the transducer 30 moves in the y-axis direction while generating an ultrasonic wave.

Ultrasonic transducer element groups located at both ends of the transducer 30, each including an appropriate number of (for example, 5) ultrasonic transducer elements, are labeled receiving sections A and B. Attention will now be paid to the intensities of the reflected wave detected by the receiving sections A and B.

Figure 17:
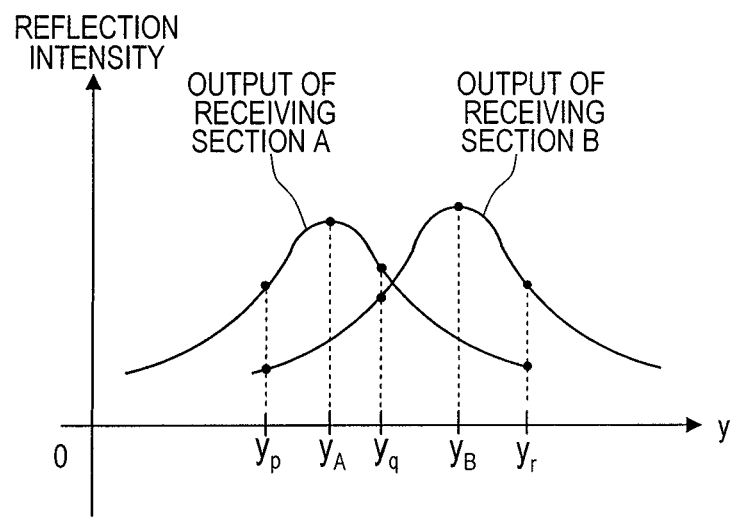
FIG. 17 A diagram showing waveforms of reflected waves detected by receiving sections A and B.

FIG. 17 shows waveforms of the distributions of the reflection intensities respectively detected by the receiving sections A and B. These waveforms are generated by the intensity information generation section 23. The reflection intensity detected by the receiving section A has a maximum value when the transducer 30 is at a position $y_A$. The reflection intensity detected by the receiving section B has a maximum value when the transducer 30 is at a position $y_B$. The receiving section A starts detecting the reflected wave from the blood vessel 3 and also starts receiving the reflected wave which has passed the center of the cross-section of the blood vessel 3, before the receiving section B. Therefore, $y_A < y_B$. The maximum value at the position $y_A$ is not necessarily the same as the maximum value at the position $y_B$. The reason for this is that the ultrasonic wave is transmitted to the biological body (blood vessel 3) and so the reflected wave includes variances.

Whether or not the arranging direction of the ultrasonic transducer elements and the longer axis of the blood vessel 3 are parallel to each other is known neither to the user nor to the ultrasonic diagnostic apparatus. However, when the waveforms shown in FIG. 17 are obtained as a result of measuring the reflection intensities detected by the receiving sections A and B located at both ends of the transducer, it is understood that the transducer 30 and the blood vessel 3 are in the positional relationship shown in FIG. 16.

In such a case, the transducer 30 can be rotated to adjust the direction of the transducer 30 to be parallel to the blood vessel 3.

For example, the transducer 30 is rotated by a predefined angle and then moved again in the y-axis direction, and the reflection intensity distributions are obtained by the receiving sections A and B. When the waveforms shown in FIG. 17 are obtained, which show that the reflection intensities detected by the receiving sections A and B are different from each other, the transducer is again rotated by the predefined angle. This is repeated until the reflection intensities detected by the receiving sections A and B both become maximum at the same position.

Figure 18:
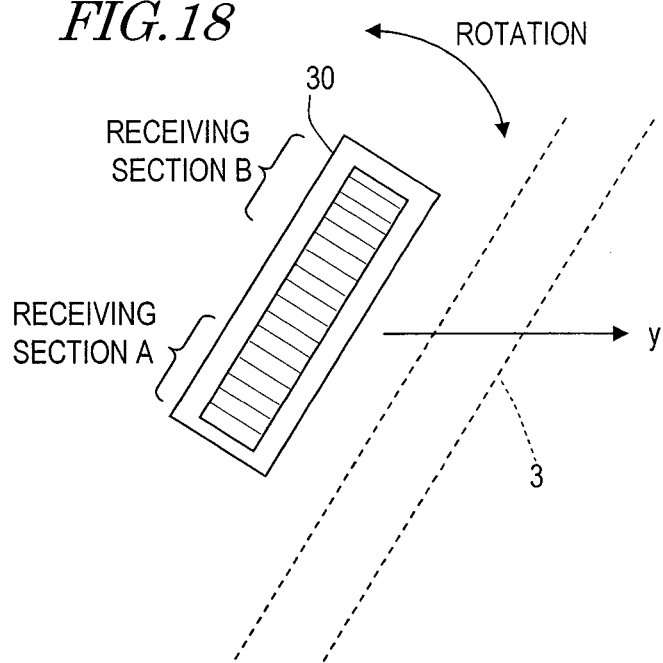
FIG. 18 A diagram showing an example in which the transducer 30 is located parallel to the blood vessel 3 as a result of rotating the transducer 30.

FIG. 18 shows an example in which the transducer 30 and the blood vessel 3 are located parallel to each other as a result of rotating the transducer 30. FIG. 19 shows waveforms when the reflection intensities detected by the receiving sections A and B are both maximum at the position yo. The reflection intensities detected by the receiving sections A and B are both maximum at the same time, and at this point, the transducer 30 and the blood vessel 3 are parallel to each other. After this, the processing described in Embodiment 1 is executed to specify the position of the transducer 30 at which the reflection intensity is maximum as the position (central position) at which the ultrasonic wave passes the center of the blood vessel. Owing to this, the elasticity characteristic of the blood vessel 3 can be accurately measured.

Portions (a) and (b) of FIG. 20 show a physical structure of the ultrasonic probe 13 in this embodiment. Portion (a) of FIG. 20 is an isometric view, and portion (b) of FIG. 20 is a plan view. Among the elements of the ultrasonic probe 13 in this embodiment, the elements identical with those of the ultrasonic probe shown in portions (a) and (b) of FIG. 11 bear identical reference numerals therewith, and descriptions thereof will be omitted.

As compared with the ultrasonic probe in Embodiment 1, the ultrasonic probe 13 in this embodiment further includes a rack 112 and a motor 113. The rack 112 is a flat plate-like rod including teeth, and is physically coupled with the case 50. A rotation shaft of the motor 113 is provided with a pinion, which is engaged with the teeth of the rack 112. For the convenience of description, in this embodiment, the motors 111 and 113 have the same performance and the rotation shafts thereof are provided with the same type of pinions. The number of the teeth of the rack 110 is the same as the number of the teeth of the rack 112.

In this embodiment, the case 50 is connected to the rack 110 and also to the rack 112. Especially, the case 50 is connected to be rotatable with respect to both of the racks 110 and 112. The connection point of the case 50 and the rack 112 is movable with a slight play in the x-axis direction. The reason for this is that when the case 50 rotates on an x-y plane, the distance between the fulcrums may be changed.

The rotation of the motor 111 and the rotation of the motor 113 are independently controlled by a control signal from the probe control section 25. It is assumed that the case 50 is located parallel to the x-axis shown in portion (b) of FIG. 20. When the motor 111 and the motor 113 are rotated in opposite directions from each other at the same rotation rate in this state, the case 50 moves in the y-axis direction while being kept parallel to the x-axis direction. This control on the movement is executed for moving the transducer 30 as shown in FIG. 16.

By contrast, when the motor 111 and the motor 113 are rotated at different rotation rates, the case 50 becomes unparallel to the x-axis direction and is inclined to the x-axis at an angle corresponding to the difference between the rotation rates. Namely, the case 50 is rotated on the x-y plane by a prescribed angle. At the time when a prescribed inclination is obtained, the motors 111 and 113 are stopped rotating and then rotated in opposite directions from each other at the same rotation rate. When this is done, the case 50 moves in the y-axis direction while keeping the inclination. This control on the movement is executed for moving the transducer 30 as shown in FIG. 18.

Figure 21:
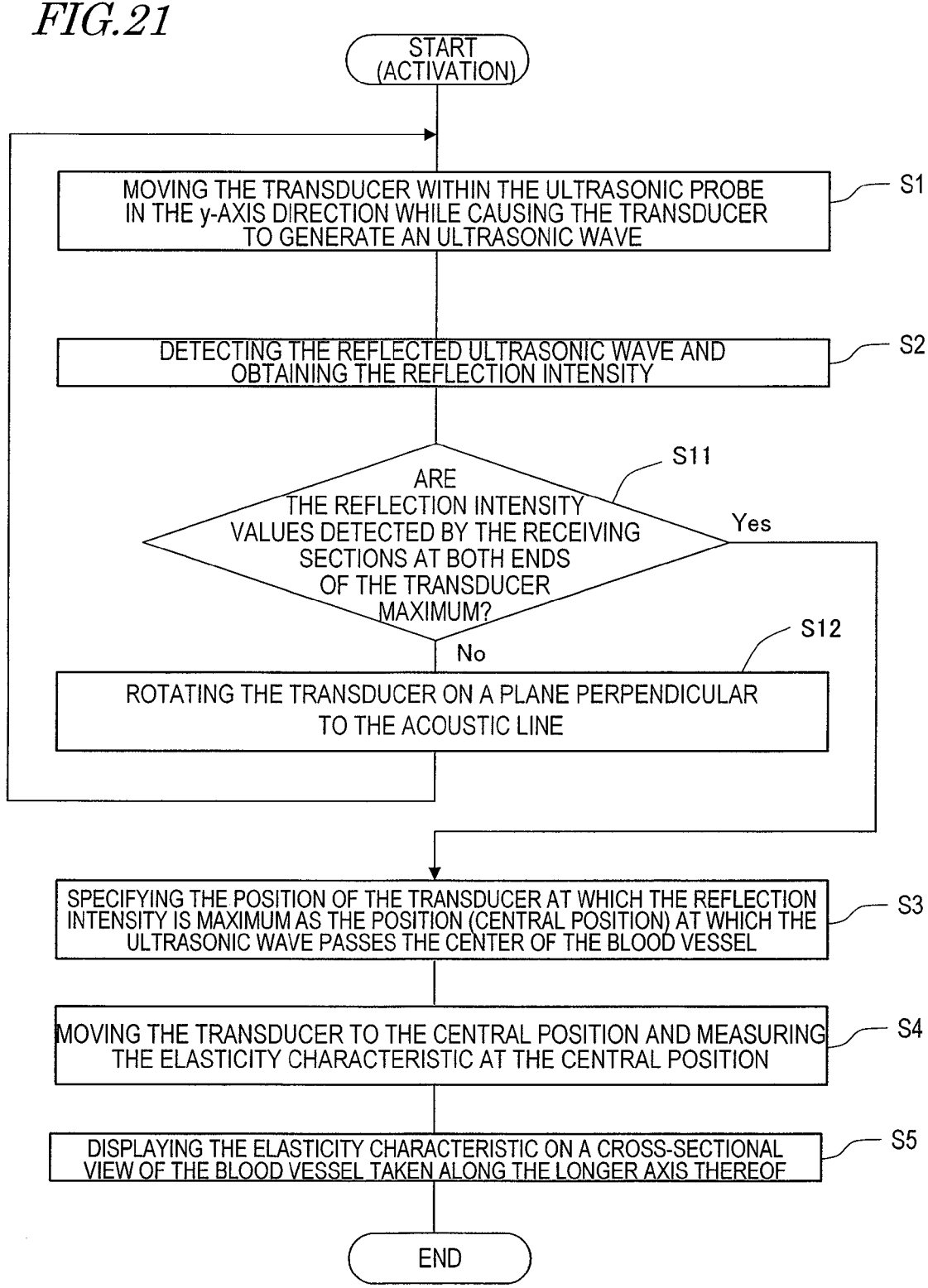
FIG. 21 A flowchart showing a processing procedure of measuring the elasticity characteristic of the blood vessel 3 executed by the ultrasonic diagnostic apparatus 11 in Embodiment 2.

FIG. 21 is a flowchart showing a processing procedure of measuring the elasticity characteristic of the blood vessel 3 by the ultrasonic diagnostic apparatus 11 in this embodiment. As compared with the flowchart shown in FIG. 12, this flowchart further includes steps S11 and S12. Hereinafter, steps S11 and S12 will be described.

Step S11 corresponds to processing of determining whether or not the transducer 30 and the blood vessel 30 are inclined with respect to each other. For example, the central position determination section 24 determines whether or not the reflection intensities detected by the receiving sections at both ends of the transducer (the receiving sections A and B) are maximum. When both of the reflection intensities are maximum, the processing advances to step S3; and otherwise, the processing advances to step S12. The reflection intensities are provided by the intensity information generation section 23 based on the outputs from the receiving sections at both ends of the transducer.

In step S12, the probe control section 25 rotates the case 50 accommodating the transducer 30 on the x-y plane by a prescribed angle (for example, 10 degrees). Then, the processing returns to step S1, and the same processing is repeated. The x-y plane is perpendicular to the acoustic line. While the ultrasonic probe 13 is applied to the body surface, the x-y plane matches the plane parallel to the body surface.

The loop of steps S1, S2, S11 and S12 is continued until the reflection intensities detected by the receiving sections at both ends of the transducer are both maximum at the same time in step S11. Namely, the angle of the transducer 30 is changed on the x-y plane until the transducer 30 becomes parallel to the blood vessel 3. Then, the processing of steps S3 through S5 is executed, and thus the elasticity characteristic of the blood vessel is accurately measured and displayed.

In FIG. 21, steps S1, S2, S11 and S12 are repeated as a loop. Alternatively, such a repetition may not be executed. For example, the transducer 30 may be caused to scan the blood vessel 3 once. In this case, an angle by which the transducer 30 should be rotated can be calculated using the positions $y_A$ and $y_B$ at which the reflection intensities are maximum. Specifically, the probe control section 25 calculates the angle to be found (the angle by which the transducer 30 should be rotated) $\theta$ by $\theta=\tan^{-1}((y_A-y_B)/T)$. T represents the distance between the receiving sections A and B.

Since the angle by which the transducer 30 should be rotated can be calculated by merely causing the transducer 30 to scan the blood vessel 3 once, the transducer 30 can be made parallel or generally parallel to the blood vessel 3 quickly and certainly. Therefore, the time period from when the ultrasonic probe 13 is applied to the body surface until the measurement is started can be shortened.

In this embodiment, the receiving sections A and B shown in FIG. 16 and FIG. 18 are used as an example of the receiving sections at both ends of the transducer 30. The shapes and locations of the receiving sections A and B may be varied.

Figure 22:
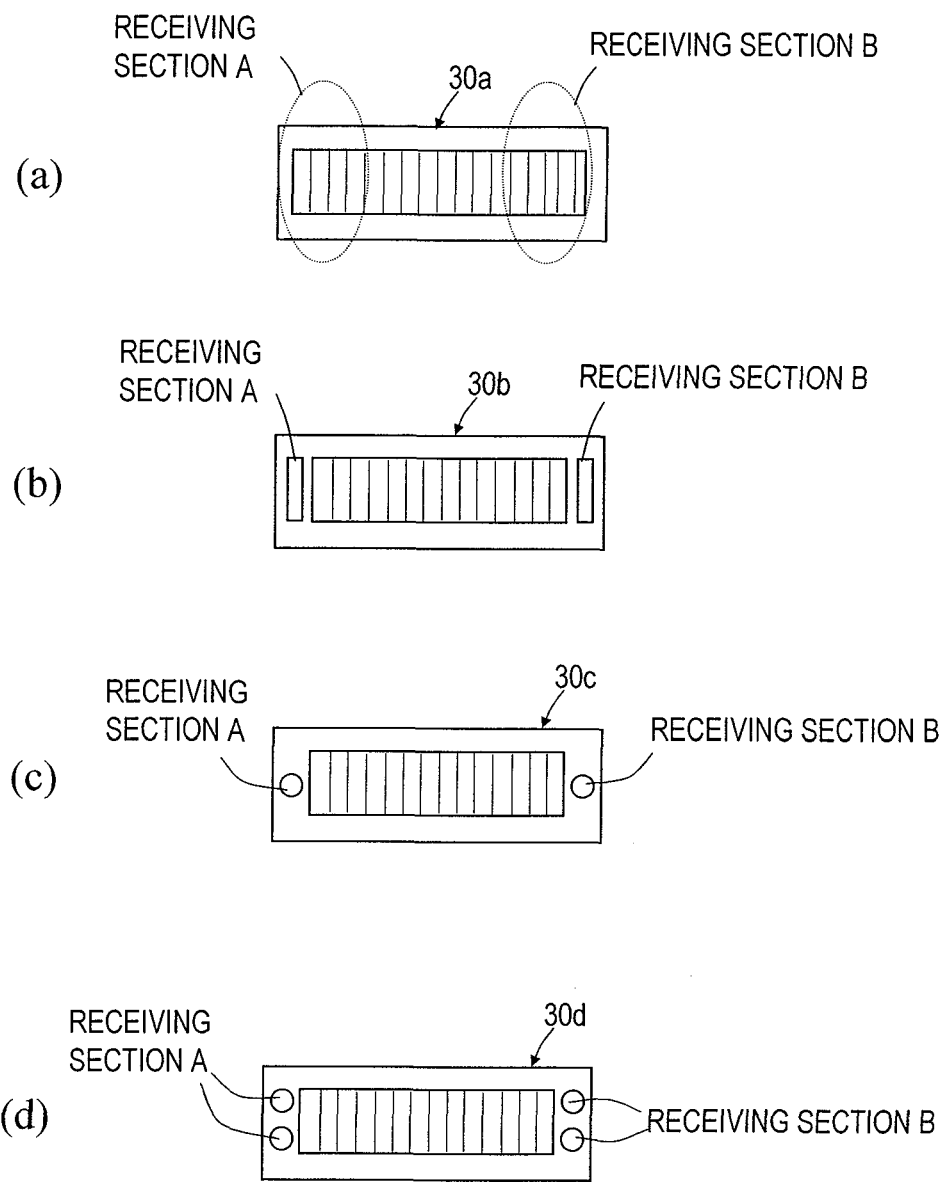
FIG. 22 (a) through (d) respectively show examples of transducers 30a through 30d having the receiving sections A and B with different shapes at different locations.

For example, portions (a) through (d) of FIG. 22 respectively show transducers 30a through 30d. The receiving sections A and B of the transducers 30a through 30d are different from one another in the shape and location. The transducer in portion (a) of FIG. 22 is the same as the transducer 30 shown in FIG. 16 and FIG. 18. It is determined whether or not the transducer 30 is parallel to the blood vessel 3 using the intensities of the reflected wave detected by the two receiving sections in the areas surrounded by the dotted lines. Portion (b) through (d) of FIG. 22 show examples of the location and shape of the receiving sections A and B which are physically independent. Whichever of the transducers 30a through 30d may be used, the reflection intensities necessary to determine whether or not the transducer 30 is parallel to the blood vessel 3 can be detected.

In all the above examples, the receiving sections A and B are provided at both ends of the transducer. However, the receiving sections A and B do not need to be at both ends of the transducer. For example, the receiving section A may be provided at the center of the transducer and the receiving section B may be provided at one end of the transducer. The receiving sections A and B do not need to be provided at both ends of the transducer as long as the receiving sections A and B are away from each other sufficiently for the waveforms of the reflection intensities shown in FIG. 17 to be obtained.

In Embodiments 1 and 2, the transducer 30 is moved within the ultrasonic probe 13 by a so-called rack and pinion system, but this is merely an example. Alternatively, the movement and the rotation of the case 50 and the transducer 30 may be controlled by coupling the motor 111 and/or the motor 113 with the case 50 by a belt and winding or advancing the belt by the rotation of the motor(s). The type of the motor, which is the driving device, is arbitrary, and for example, a linear motor or a voice coil motor may be usable. It would be easy for a person of ordinary skill in the art to change the structure of the ultrasonic probe 13 for moving the transducer 30 in accordance with the driving system of the motor used.

As described above in Embodiments 1 and 2, in the flowcharts in FIG. 12 and FIG. 21 showing the processing procedure of measuring the elasticity characteristic, when the probe reaches the central position after the start of the processing, the elasticity characteristic is measured and the measured elasticity characteristic is displayed, and the processing is finished. However, the processing does not need to be finished after one measurement and may be executed continuously or within a certain cycle. In this way, even if the position is deviated because the hand holding the probe is unstably shaken or the like, the probe can be moved to the central position to measure the elasticity characteristic each time this occurs. Thus, an accurate elasticity characteristic of the blood vessel can be obtained. In this case, the movable range of the transducer may be slightly narrowed than the original movable range. By such an arrangement, the processing time period can be shortened. Alternatively, after the processing procedure is finished once, the deviation of the position caused because the hand is unstably shaken can be detected based on the reflection intensity difference obtained in step S2 in FIG. 12 or in step S2 in FIG. 21, without moving the transducer as in step S1 in FIG. 12 or in step S2 in FIG. 21. In the case where the reflection intensity difference is larger than a certain value, the processing procedure of measuring the elasticity characteristic may be executed again.

In Embodiments 1 and 2, the transducer 3 moves in one direction or two directions. One direction means a direction parallel to the surface of the biological body or a rotation direction, and two directions means a direction parallel to the surface of the biological body and a rotation direction on a plane.

Figure 23:
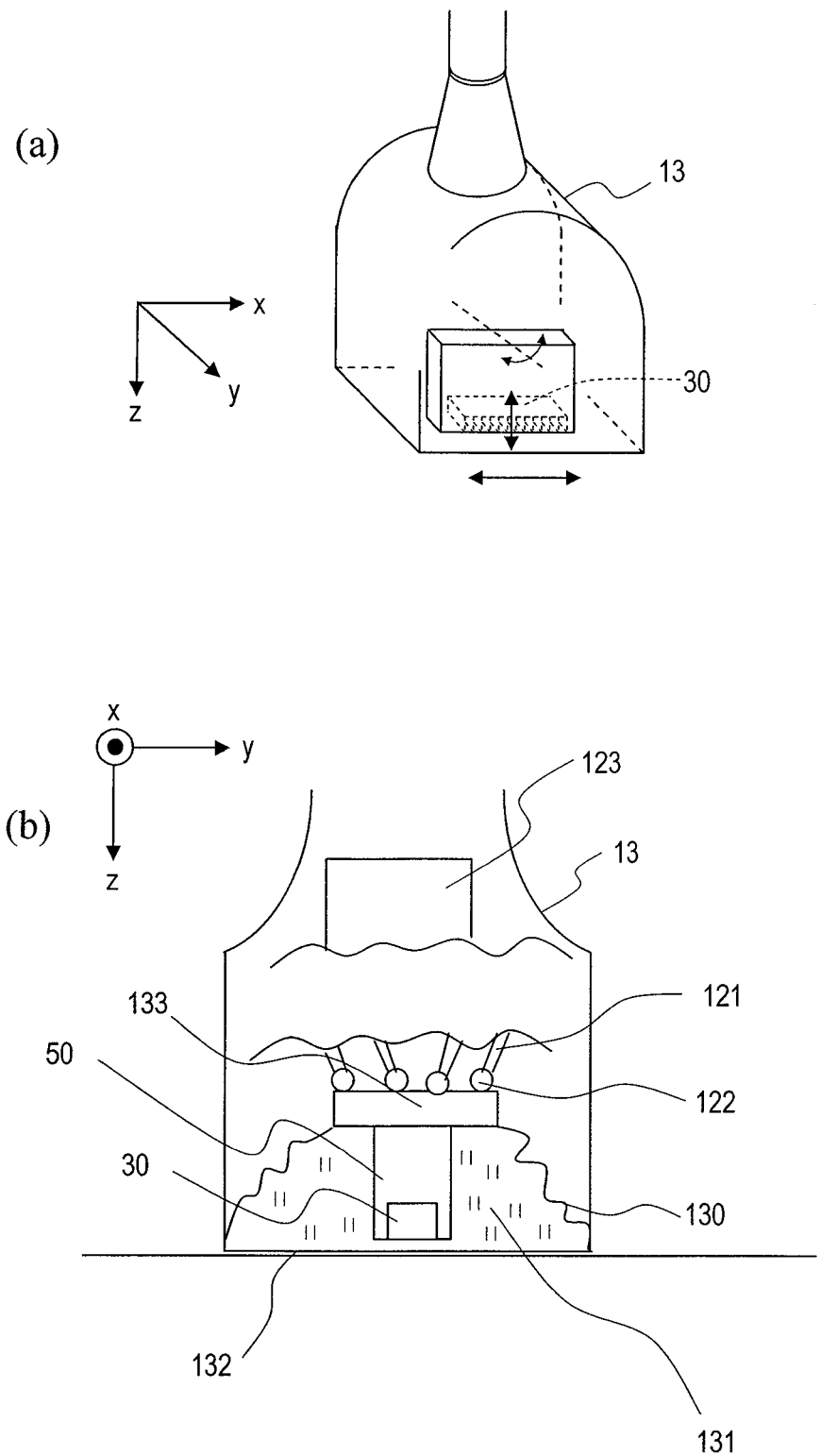
FIGS. 23 (a) and (b) show a multi-axis operation of the transducer 30 and a structure of the ultrasonic probe 13.

However, the transducer 30 may perform a multi-axis operation, i.e., may move in other directions in addition to moving in one direction or two directions. As an example of the transducer 30 moving in the other directions, portion (a) of FIG. 23 shows a transducer 30 which moves in the x-axis direction and the z-axis direction and also rotates around an axis parallel to the y-axis direction as the center of rotation. Hereinafter, the rotation around the y-axis direction as the center of rotation will be referred to as a "rotation in the y-axis direction".

The rotation in the y-axis direction is used when the blood vessel is inclined in a depth direction toward the inside of the biological body from the surface thereof. The movement in the z-axis direction is used in order to change the physical position of the focal point in the depth direction. The movement in the x-axis direction is used in order to change the measurement position in the axial direction of the blood vessel.

A driving device for realizing the multi-axis operation can be structured with a plurality of links, a plurality of joints and a plurality of actuators. For example, it is desirable to use one of such structures, namely, a parallel link mechanism. A parallel link mechanism includes a plurality of links, a plurality of joints and a plurality of actuators, and has at least two links arranged side by side.

Portion (b) of FIG. 23 is a cross-sectional view of an ultrasonic probe 13 having a parallel link mechanism, which is taken along a plane parallel to a y-z plane.

The ultrasonic probe 13 includes a bag portion 130. The bag portion 130 accommodates an acoustic coupling liquid 131 and the transducer 30 in a sealed state. A portion of the acoustic coupling liquid 131 which is located between a window section 132 on a front surface of the ultrasonic probe 13 (surface to be attached to the surface of the biological body) and the transducer 30 propagates an ultrasonic wave generated by the transducer 30. It is desirable that the bag portion 130 is formed of a flexible material which is not permeated by the acoustic coupling liquid, for example, a rubber material, a resin film material or the like.

In the parallel link mechanism, the transducer 30 and actuators 123 are located discretely and oppositely with respect to an operation point section 133, which acts as an operation point. Links 121 and joints 122 for conveying the power of the actuators 123 to the operation point section 133 are located on the actuators 123 side with respect to the operation point section 133. Therefore, the links 121, the joints 122 and the actuators 123 are not sealed by the bag portion 130 and so are not immersed in the acoustic coupling liquid 131. It is an advantage of the parallel link mechanism that the actuators 123 can be installed away from the transducer 30. This is a difference from a single link mechanism having an actuator at each joint, like in a robot arm.

Figure 24:
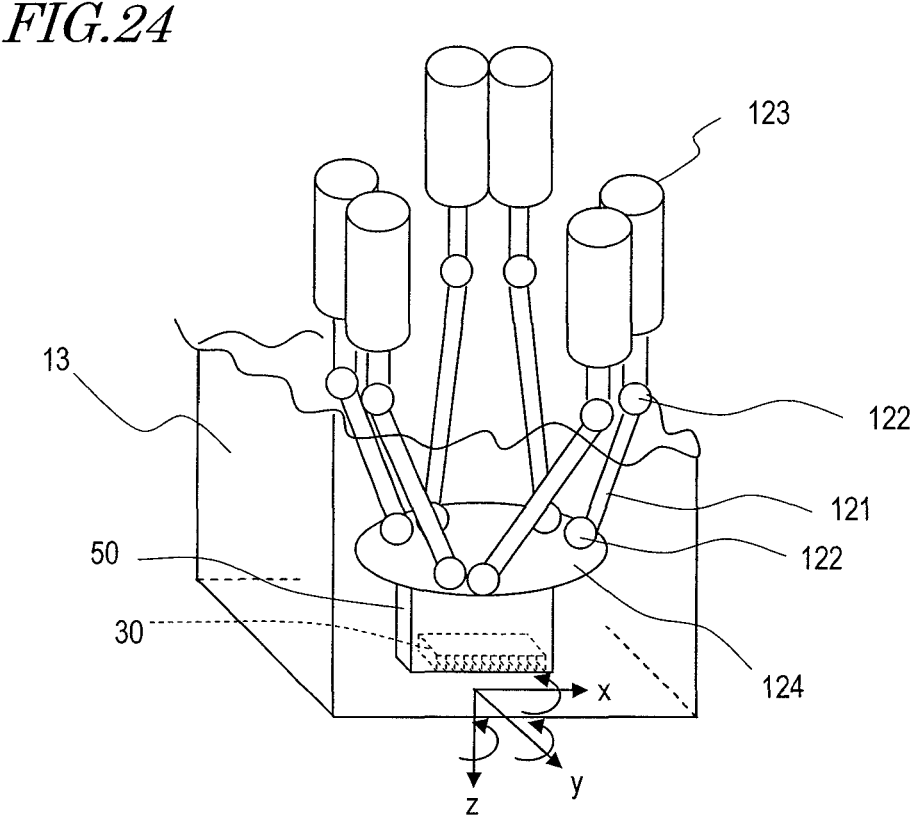
FIG. 24 A diagram showing a specific example of a structure of the ultrasonic probe 13.

FIG. 24 shows an ultrasonic probe 13 having a linear motion parallel link mechanism with 6 degrees of freedom. In the ultrasonic probe 13, the transducer 30 is attached to one of surfaces of a movable base 124. The joints 122 are attached to the other surface of the movable base 124. The joints 122 and the links 121 are respectively connected to each other, and convey the driving power of the respective actuators 123.

By driving six linear motion actuators, the position and angle of the movable base 24 are changed with a total of six degrees of freedom, which are the x direction, the y direction, the z direction and the rotation directions around each axis as the center of rotation. With such an arrangement, the transducer 30 can be moved and rotated in a total of six directions, not only in the direction parallel to the surface of the biological body.

Figure 25:
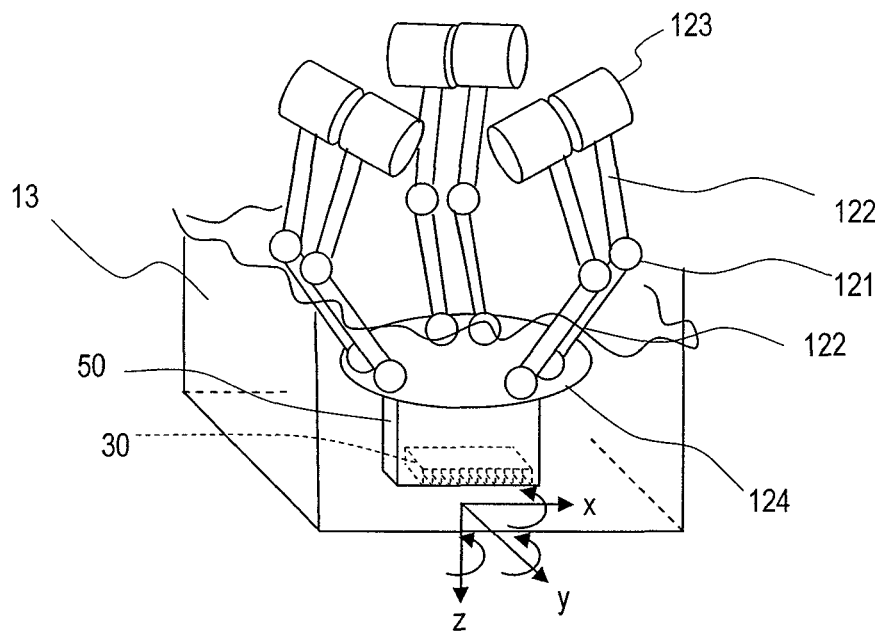
FIG. 25 A diagram showing a specific example of a structure of the ultrasonic probe 13.
Figure 26:
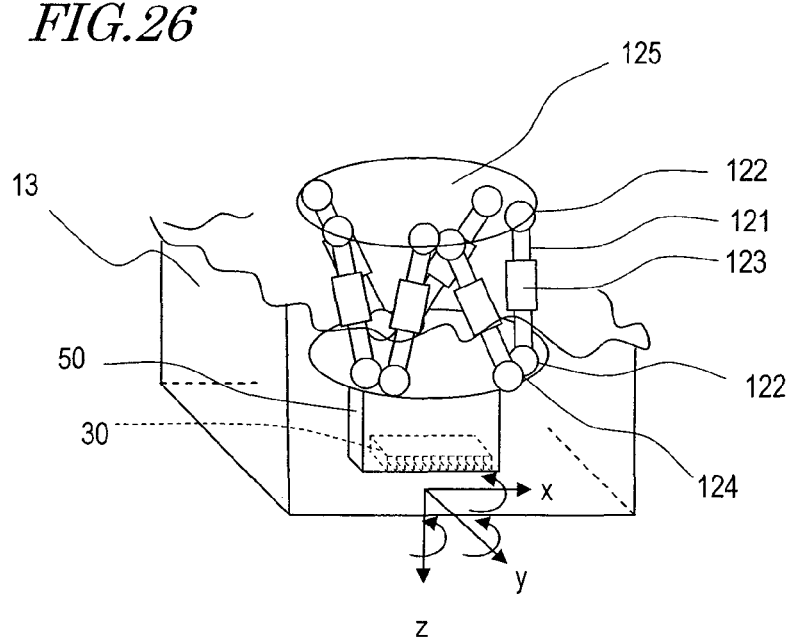
FIG. 26 A diagram showing a specific example of a structure of the ultrasonic probe 13.

The linear motion actuators (not shown) are fixed to a casing of the ultrasonic probe 13. The linear motion actuators may be of, for example, a mechanism in which the motor is linearly moved by a ball screw or the motor is a linear motor. As examples, the ultrasonic probes 13 shown in FIG. 25 and FIG. 26 will be described. FIG. 25 shows a rotatable parallel link mechanism, and FIG. 26 shows an extendable parallel link mechanism. As shown in FIG. 25 and FIG. 26, when the actuators 123 are driven, the driving power thereof is conveyed to the movable base 124 via the joints 122 and the links 121. The position and angle of the movable base 124 are changed with six degrees of freedom, which are the x direction, the y direction, the z direction and the rotation directions around each axis as the center of rotation, not only in the direction parallel to the surface of the biological body. The rotatable parallel link mechanism adopts rotatable actuators, and the extendable parallel link mechanism adopts extendable actuators.

The degrees of freedom of the parallel link mechanism does not need to be always six. Any number of degrees of freedom which is required for operating the probe is sufficient. For example, it is acceptable that the probe includes a movable shaft which gives two degrees of freedom among the six degrees of freedom mentioned above. The number of the joints and the number of links may be varied in accordance with the degree of freedom. The joints may be omitted depending on the positions at which the actuators are installed, the length of the links or the like.

The degree of freedom with which the position of the transducer can be changed is defined by the number of shafts capable of driving the transducer 30. An operation section may be an input device such as a joystick or the like. An operation of changing the position or orientation of the transducer may be performed during the processing of determining the central position of the blood vessel or during the measurement of the elasticity characteristic of the blood vessel. For example, the processing of determining the central position of the blood vessel may be first executed, and then the transducer may be moved in the axial direction of the blood vessel to measure the elasticity characteristic in a wider range.

An operation section (not shown) may be provided in a main body of the ultrasonic diagnostic apparatus. The operation section is operated by the user to output a control signal for changing the position or orientation of the transducer within the ultrasonic probe. The position of the transducer varies based on the control signal.

The operation section does not need to be provided in the main body of the ultrasonic diagnostic apparatus. For example, the operation section and the ultrasonic diagnostic apparatus may be connected to each other via a network. In this case, the ultrasonic probe is remote-controlled based on a control signal from the operation section.

A switch (not shown) may be provided in the probe or the main body of the ultrasonic diagnostic apparatus, so that the transducer can be switched either to, or not to, move and/or rotate within the ultrasonic probe. The reason why this is possible is that an operator skilled in using the probe, upon looking at a displayed image of the elasticity characteristic, could easily determine whether the measurement results of the elasticity characteristic are correct or not, namely, whether the probe is appropriately located and the elasticity characteristic of the blood vessel is measured at the center of the cross-section of the blood vessel or not. Since the ultrasonic diagnostic apparatus can be switched either to, or not to, execute the processing of making a determination on the central position, the ultrasonic diagnostic apparatus can be operated in accordance with the level of skill of the user, which improves the convenience of the ultrasonic diagnostic apparatus.

Embodiment 3

Hereinafter, an ultrasonic diagnostic apparatus in Embodiment 3 according to the present invention will be described.

The ultrasonic diagnostic apparatus in this embodiment has the same structure as the ultrasonic diagnostic apparatus 11 (FIG. 5) in Embodiment 1, and so will be described with reference to the ultrasonic diagnostic apparatus 11 shown in FIG. 5 and the elements thereof.

In Embodiment 1, the x axis of the transducer 30 (for example, FIG. 4) and the longer axis of the blood vessel 3 along the extending direction of the blood vessel 3 are located substantially parallel to each other.

In this embodiment, the x axis of the transducer 30 (for example, FIG. 4) and the longer axis of the blood vessel 3 along the extending direction of the blood vessel 3 are located substantially "perpendicular" to each other.

In such a situation, the intensity information generation section 23 of the ultrasonib diagnostic apparatus 11 (FIG. 5) in this embodiment sequentially changes, in the x-axis direction, the position at which the ultrasonic wave is generated using the transducer elements of the transducer 30, and measures the reflection intensity of the reflected wave of the transmitted ultrasonic wave to generate intensity information. The intensity information generation section 23 measures the intensity of the reflected wave (reflection intensity) based on the amplitude of the receiving signal delay-time-controlled by the delay time control section 16 and generates the intensity information which represents the reflection intensity distribution.

The transducer 30 moves within the ultrasonic probe 13 in a direction parallel to the body surface and perpendicular to the x-axis direction, namely, in the longer axis direction of the blood vessel, while generating an ultrasonic wave. The intensity information generation section 23 measures the reflection intensity obtained as the transducer 30 moves and generates the intensity information.

Hereinafter, with reference to FIG. 27 and FIG. 28, a principle of processing of adjusting the positional relationship between the transducer 30 and the blood vessel 3 will be described. This processing causes an ultrasonic wave (acoustic line) transmitted from the transducer 30 to pass the center of the cross-section of the blood vessel 3, and allows the elasticity characteristic of the blood vessel 3 to be accurately measured.

As described above, in this embodiment, the x axis of the transducer 30 (for example, FIG. 27) and the longer axis of the blood vessel 3 are located substantially perpendicular to each other. The z axis of the transducer 30 (for example, FIG. 27) and the longer axis of the blood vessel 3 do not need to be substantially perpendicular to each other.

Figure 27:
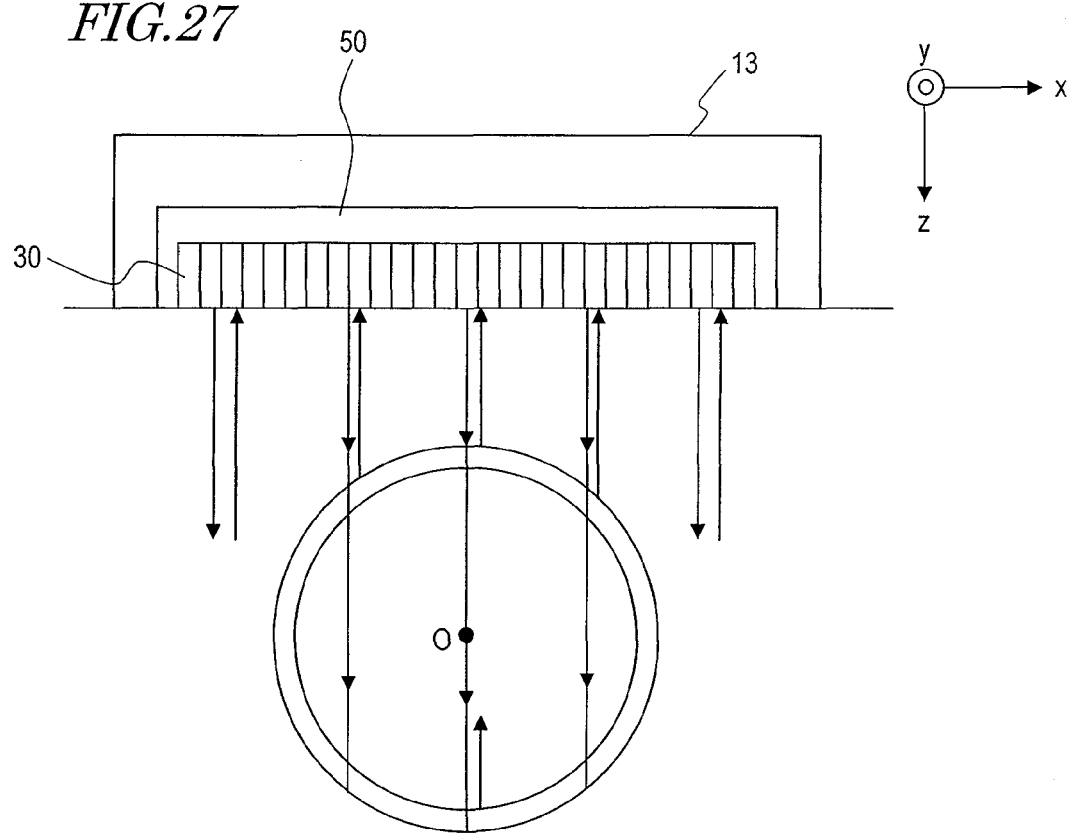
FIG. 27 A diagram showing the transducer 30 performing a scan in the x-axis direction while generating an ultrasonic wave.

FIG. 27 shows the transducer 30 moving in the x-axis direction for performing a scan while generating an ultrasonic wave. The transducer 30 is accommodated in the case 50.

Based on a control signal from the transmission section 14, the transducer 30 moves in the x-axis direction for performing a scan from one end to the other end as shown in, for example, portions (a1) and (b1) of FIG. 3, while generating an ultrasonic wave.

Figure 28:
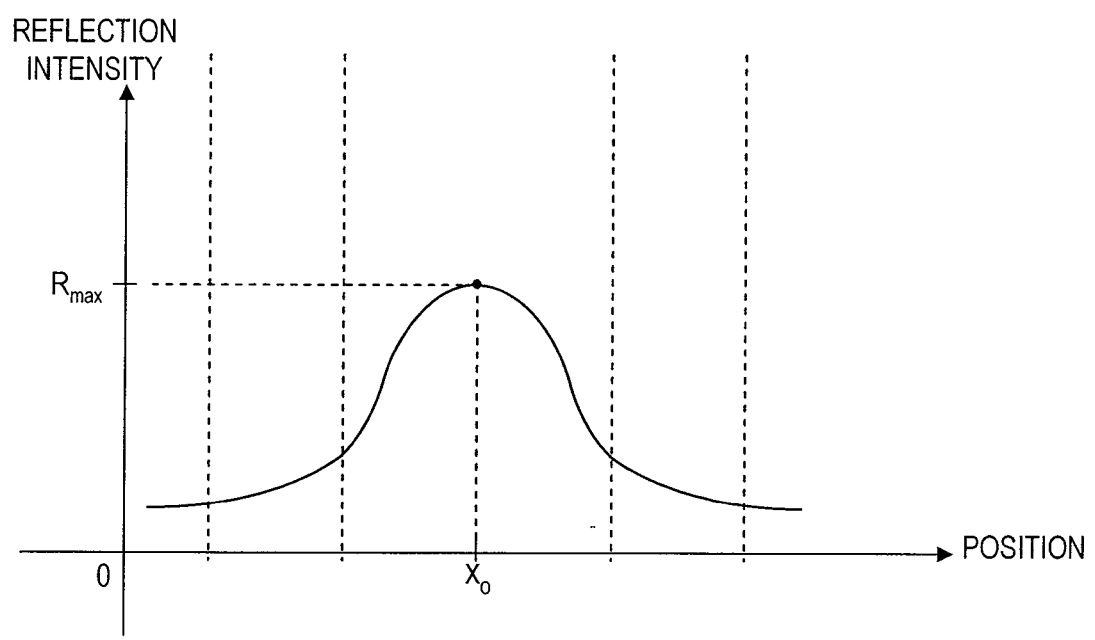
FIG. 28 A diagram showing a reflection intensity distribution of a reflected ultrasonic wave generated by an intensity information generation section 23 as a result of performing a scan in the x-axis direction with an ultrasonic wave.

FIG. 28 shows a distribution of the reflection intensity of the reflected ultrasonic wave generated by the intensity information generation section 23 as a result of a scan performed in the x-axis direction with an ultrasonic wave. The horizontal axis represents the length direction (x-axis direction) of the transducer 30, and the vertical axis represents the reflection intensity. When the reflection intensity is obtained, the central position determination section 24 specifies a position Xo of the transducer 30 at which the maximum reflection intensity Rmax is obtained.

The position Xo specified by the central position determination section 24 corresponds to the position at which the acoustic line of the ultrasonic wave passes the center of the cross-section of the blood vessel 3. The reason for this is as follows. As the position passed by the transmission wave is farther from the center of the cross-section, the angle at which the transmission wave is reflected by the outer wall and the inner wall of the blood vessel 3 is closer to 90 degrees with respect to the direction of incidence and therefore the detected intensity of the reflected wave from the blood vessel 3 is lower. By contrast, as the position passed by the transmission ultrasonic wave is closer to the center o of the cross-section, the angle at which the ultrasonic wave is reflected by the outer wall and the inner wall of the blood vessel 3 is closer to the direction of incidence and therefore the detected intensity of the reflected wave from the blood vessel 3 is higher. When the transmission ultrasonic wave passes the center o of the cross-section, the direction of incidence and the direction of reflection of the ultrasonic wave match each other at the outer wall and the inner wall of the blood vessel 3 and therefore the detected intensity of the reflected wave is maximum. For this reason, it is considered that the position of the transducer 30 which has transmitted the ultrasonic wave which is reflected with the maximum reflection intensity is the position at which the transmission ultrasonic wave passes the center o of the cross-section.

After the position Xo is specified, the transmission section 14 can transmit the ultrasonic wave from the position Xo to measure the elasticity characteristic of the blood vessel 3.

In the above example, the position of the transducer 30 is fixed. Alternatively, the transducer 30 may be moved in the longer axis direction of the blood vessel 3 and the above operation may be performed at the post-movement position. In this way, while the central position of the blood vessel 3 is specified along a certain length range of the blood vessel 3 in the longer axis direction thereof, the elasticity characteristic can be accurately measured at each of the positions.

In this embodiment, as shown in portions (a) and (b) of FIG. 11, a mechanism for driving the transducer 30 is provided in the ultrasonic probe 13 in order to allow the transducer 30 to move within the ultrasonic probe 13.

Figure 29:
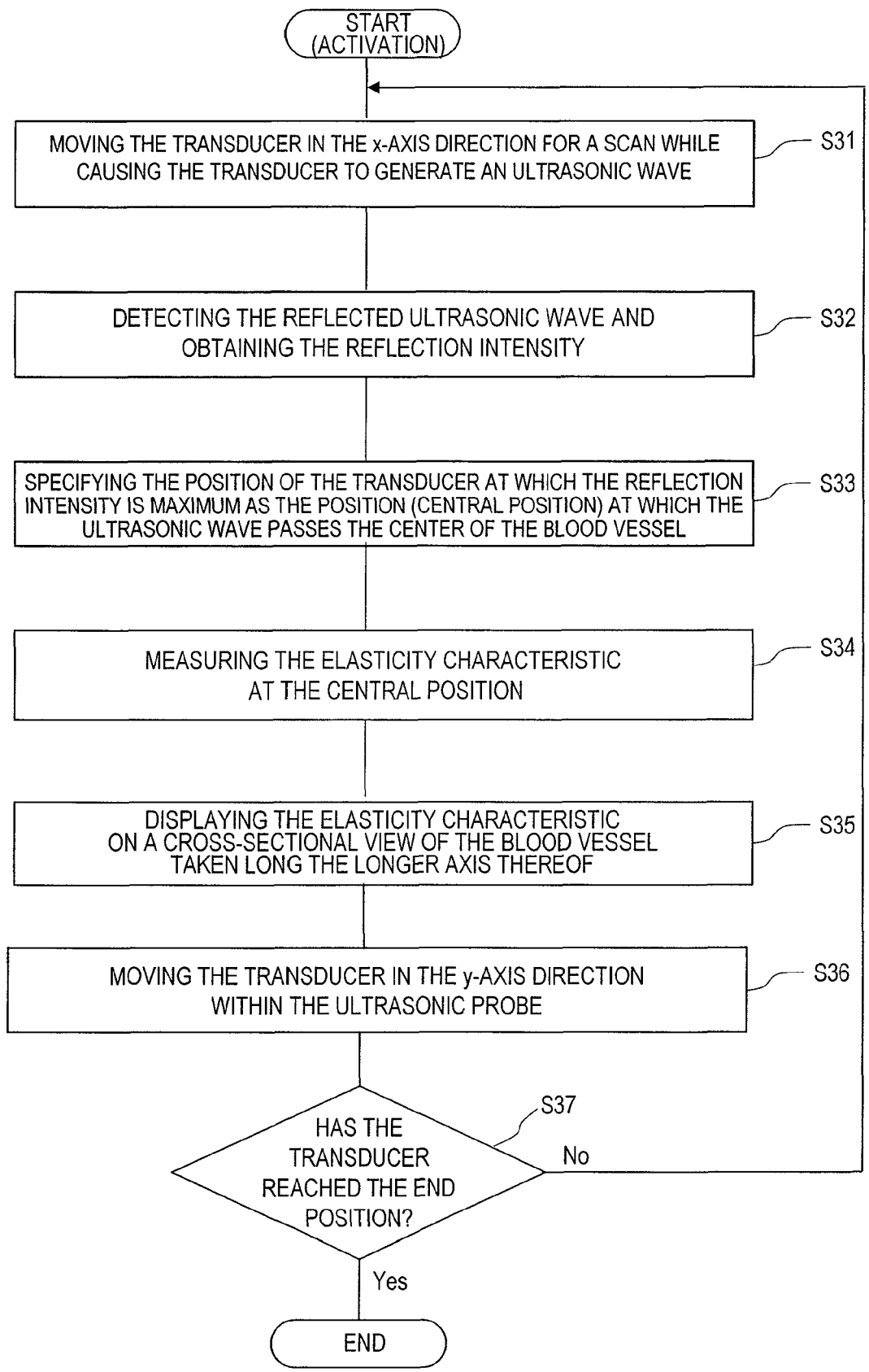
FIG. 29 A flowchart showing a processing procedure of measuring the elasticity characteristic of the blood vessel 3 executed by the ultrasonic diagnostic apparatus 11 in Embodiment 3.

FIG. 29 is a flowchart showing a processing procedure of measuring the elasticity characteristic of the blood vessel 3 executed by the ultrasonic diagnostic apparatus 11 in this embodiment. Here, the ultrasonic probe 13 shown in portions (a) and (b) of FIG. 11 is used.

In step S31, when the probe control section 25 sends a control signal to the ultrasonic probe 13, the transducer 30 moves in the x-axis direction for performing a scan while generating an ultrasonic wave. In step S32, the intensity information generation section 23 detects a reflected wave of the ultrasonic wave repeatedly transmitted by the transducer 30, and obtains a reflection intensity. An ultrasonic wave is sequentially transmitted from the transducer 30 from one end to the other end thereof and a reflected wave is received, and thus a reflection intensity distribution is obtained.

In step S33, the central position determination section 24 specifies the position of the transducer 30 at which the reflection intensity is maximum as the position (central position) at which the ultrasonic wave passes the center o of the blood vessel.

In step S34, the control section 26 instructs the elasticity characteristic of the blood vessel 3 to be measured at the central position. Based on this instruction, the phase detection section 17, the filtering section 18, the calculation section 19 and the calculation data storage section 20 operate to measure the elasticity characteristic of the blood vessel 3.

In step S35, the display section 21 displays the cross-section along the longer axis of the blood vessel and also displays the elasticity characteristic measured by the calculation section 19 as being superimposed on the cross-sectional view thereof.

In step S36, the probe control section 25 moves the transducer 30 within the ultrasonic probe 13 in the y-axis direction by a certain distance. For example, for measuring the elasticity characteristic of the blood vessel 3 at five different sites, the probe control section 25 moves the transducer 30 within the ultrasonic probe 13 in the y-axis direction by ⅕ of the distance of the movable range in the ultrasonic probe 13.

In step S37, it is determined whether or not the transducer 30 has reached the end position of the movable range in the ultrasonic probe 13. When the transducer 30 has not reached the end position, the processing returns to step S31. When the transducer 30 has reached the end position, the processing is finished.

By the processing of steps S31 through S33, the position of the transducer 30 at which the reflection intensity is maximum is specified as the central position, and the elasticity characteristic of the blood vessel 3 is measured at the central position. Therefore, the distortion of the blood vessel can be accurately measured, and the elasticity characteristic can be accurately measured.

Embodiment 4

Hereinafter, an ultrasonic diagnostic apparatus in Embodiment 4 according to the present invention will be described.

In Embodiment 3, the center of the cross-section of the blood vessel 3 is specified and the transducer 30 is moved in a prescribed axial direction within the ultrasonic probe 13. This is effective when the blood vessel 3 extends parallel to the epidermis.

In this embodiment, an ultrasonic probe capable of specifying the center of the cross-section perpendicular to the blood vessel 3 even where the blood vessel 3 is not parallel to the epidermis will be described.

Portions (a) and (b) of FIG. 30 each show an example of a structure of an ultrasonic probe 13 for swinging the case 50 like a pendulum with a relatively upper point Ka in the case 50 used as a fulcrum shaft. Portion (c) of FIG. 30 shows a structure of the ultrasonic probe 13 in this embodiment. Elements having identical functions with those of the ultrasonic probe 13 shown in FIG. 20 bear the identical reference numerals therewith, and descriptions thereof will be omitted. The fulcrum shaft (x axis) of the ultrasonic probe 13 is parallel to the body surface. The ultrasonic probe 13 shown in portion (c) of FIG. 30 is structured such that the rotation of the motor is conveyed to the fulcrum shaft via a conveyance mechanism such as a gear, a belt or the like. It should be noted that the rotation shaft of the motor may match the fulcrum shaft. By such a structure, the transmission direction of the ultrasonic wave transmitted from the transducer 30 can be changed. The rotation direction and the rotation angle of the transducer 30 are controlled by the probe control section 25. In the example of portions (a) and (b) of FIG. 30, the movable angle is from −90 degrees to +90 degrees. The point K as the fulcrum shaft is provided away from the body surface, but may be closer to the body surface.

Portion (a) of FIG. 30 shows the transducer 30 which has been rotated by angle $\theta_0$ ($\theta_0 > 0$). Portion (b) of FIG. 30 shows the transducer 30 at a rotation angle of 0. Portions (a) and (b) of FIG. 30 also show the position of the blood vessel 3. In this embodiment, the blood vessel 3 is not parallel to the epidermis and extends in the depth direction from the epidermis.

Using the ultrasonic probe 13 having such a structure, the elasticity characteristic of the blood vessel 3 can be measured at the central position in the cross-section vertical to the blood vessel 3 by specifying the rotation angle of the transducer 3 at which the ultrasonic wave transmitted from the transducer 3 passes the center of the cross-section of the blood vessel 3, based on the maximum reflection intensity.

Figure 31:
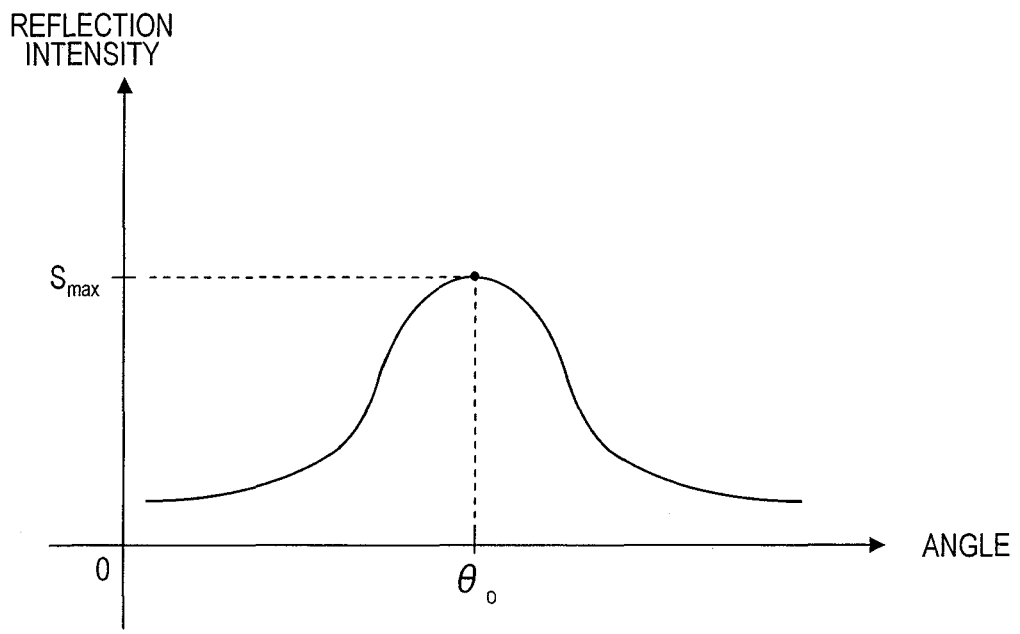
FIG. 31 A diagram showing a reflection intensity distribution of a reflected ultrasonic wave generated by the intensity information generation section 23 when an ultrasonic wave is transmitted while the angle of the ultrasonic probe 13 is changed so as to gradually increase from 0 degrees.

FIG. 31 shows a reflection intensity distribution generated by the intensity information generation section 23 when the ultrasonic wave is transmitted while the angle of the transducer 30 is changed to be gradually increased from 0 degrees. It is sufficient that the ultrasonic wave is transmitted once at each angular position.

When the angle of the transducer 30 is 0 degrees, as shown in portion (b) of FIG. 30, the angle of incidence of the ultrasonic wave on the blood vessel 3 is not the right angle. Most of the ultrasonic wave incident thereon is reflected by the outer wall and the inner wall of the blood vessel 3 in a direction different from the direction of incidence. Only a part of the ultrasonic wave returns in the direction of incidence, and the reflection intensity thereof is measured.

The reflection intensity gradually increases in the range of the angle of the transducer 30 from 0 degrees to $\theta_0$. This means that as the reflection intensity is higher, the angle of incidence of the ultrasonic wave on the blood vessel 3 is closer to the right angle. Therefore, when a higher reflection intensity is obtained, the central position determination section 24 determines that the angle of incidence is closer to the right angle.

By gradually increasing the angle of the transducer 30, the angle reaches $\theta_0$ ($\theta_0 > 0$) at which the reflection intensity is maximum. When the reflection intensity is maximum (Smax), the progressing direction of the ultrasonic wave is perpendicular to the longer axis of the blood vessel 3. The reason for this is as described above in Embodiment 3 with reference to FIG. 27.

In order to determine that the reflection intensity is maximum at angle $\theta_0$, the reflection intensity needs to be measured in the state where the transducer 30 is inclined at an angle larger than $\theta_0$. When the reflection intensity obtained at such an angle is smaller than the reflection intensity at angle $\theta_0$, it can be determined that the reflection intensity is maximum at angle $\theta_0$.

When the transducer 30 is swung to the negative angle side, which is opposite to angle $\theta_0$ ($\theta_0 > 0$), from the state where the angle is 0 degrees as shown in portion (b) of FIG. 30, the reflection intensity gradually decreases. The reason for this is that the transmission direction of the ultrasonic wave is closer to a direction parallel to the blood vessel 3. Thus, the probe control section 25 sets the swinging direction of the transducer 30 to the opposite direction.

With the above-described structure, it is not necessary to consider the relationship between the angle of the ultrasonic probe 13 and the extending direction of the blood vessel 3. Therefore, the elasticity characteristic can be accurately measured even by a user unaccustomed to the ultrasonic probe 13.

In the above embodiment, the maximum reflection intensity is used to specify the position at which the ultrasonic wave passes the center of the cross-section of the blood vessel 3 when the ultrasonic wave is incident perpendicularly on the blood vessel 3. Alternatively, the central position can be specified by using the so-called 1.5D array shown in FIG. 14 without using the maximum reflection intensity. In this way, angle $\theta_0$ can be specified at a high precision and at a high speed. In this embodiment, attention should be paid to that the position of the blood vessel 3 shown in FIG. 14 is on a plane generally parallel to the y axis.

Using the transducer 35 shown in FIG. 14, the central position can be specified based on the difference T between the reflection intensity detected by the ultrasonic transducer element group 35*a* and the reflection intensity detected by the ultrasonic transducer element group 35*b*. The principle of this is as follows.

Figure 32:
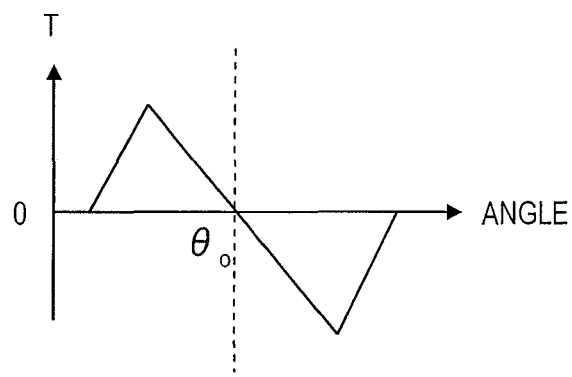
FIG. 32 A diagram showing the relationship between an angle of the transducer 35 and a difference T between the reflection intensity detected by the ultrasonic transducer element group 35a and the reflection intensity detected by the ultrasonic transducer element group 35b.

FIG. 32 shows the relationship between the angle of the transducer 35 and the difference T between the reflection intensity detected by the ultrasonic transducer element group 35a and the reflection intensity detected by the ultrasonic transducer element group 35b. When the transducer 35 is swung by angle $\theta_0$ as shown in portion (a) of FIG. 30 from the state where the angle is 0 degrees as shown in portion (b) of FIG. 30, the reflection intensity detected by the ultrasonic transducer element group 35b first starts increasing gradually from the initial value of 0. The ultrasonic transducer element group 35a is away from the blood vessel 35a. Therefore, the reflection intensity from the blood vessel 3 detected by the ultrasonic transducer element group 35a is lower than the reflection intensity detected by the ultrasonic transducer element group 35b. As a result, the output difference T initially increases in the positive direction.

Then, when the angle of the transducer 30 starts increasing, the reflection intensity detected by the ultrasonic transducer element group 35a starts increasing and so the output difference T gradually decreases. When the outputs from the ultrasonic transducer element groups 35a and 35b become equal to each other, the output difference T becomes 0. While the output difference T is 0, the ultrasonic transducer element groups 35a and 35b are located symmetrically with respect to the central axis of the blood vessel 3 as seen from the direction shown in FIG. 31. Therefore, the position of the ultrasonic transducer 35 in this state corresponds to the position perpendicular to the blood vessel.

With the method of determining the central position based on the difference between the reflection intensities using the transducer 35, a peak of the reflection intensity does not need to be detected unlike with the method of determining the maximum intensity shown in FIG. 28. Therefore, the processing time period is shortened. For adjusting the angle of the transducer 35, the sign of the output signal T may be checked to determine whether the rotation is to be made in the positive direction or in the negative direction. For example, if the sign is positive, the transducer 30 can be controlled to be rotated in the same direction as so far. If the sign is negative, the transducer 35 can be controlled to be rotated in the opposite direction. In this embodiment, the difference between the reflection intensities of the ultrasonic transducer element groups 35a and 35b is calculated by the intensity information generation section 23.

The waveform in FIG. 32 is merely an example for helping easy understanding, and the waveform is not necessarily straight and may be curved.

In Embodiment 3, the structure in which the transducer 30 is moved parallel to the body surface to change the position from which the ultrasonic wave is to be transmitted (FIG. 11, etc.) is described. In this embodiment, the structure in which the transducer 30 is swung like a pendulum to change the angle at which the ultrasonic wave is to be transmitted (FIG. 30) is described. These structures can be combined together. By such a combination, the range to which the ultrasonic wave can be transmitted is widened to enlarge the measurable range. In other words, the tolerable range for the position of the body surface to which the ultrasonic probe 13 is applied is enlarged.

In this embodiment also, the ultrasonic probe 13 shown in portion (c) of FIG. 30 which is movable in the y-axis direction and rotatable around the x-axis as the center of rotation is usable.

As shown in portion (c) of FIG. 30, the ultrasonic probe 13 in this embodiment allows the case 50 accommodating the transducer 30 to be rotated by the motor 111 like a pendulum around a fulcrum shaft parallel to the x axis as the center of rotation, unlike the ultrasonic probe in Embodiment 3.

In this embodiment, the case 50 is connected to the rack 112. The case 50 is connected so as to be rotatable with respect to the fulcrum shaft to which the power of the motor 111 is conveyed. For rotating the case 50, the case 50, the rack 112 and the motor 113 are integrally driven. The rotation of the motor 111 and the rotation of the motor 113 are independently controlled based on a control signal from the probe control section 25.

Figure 33:
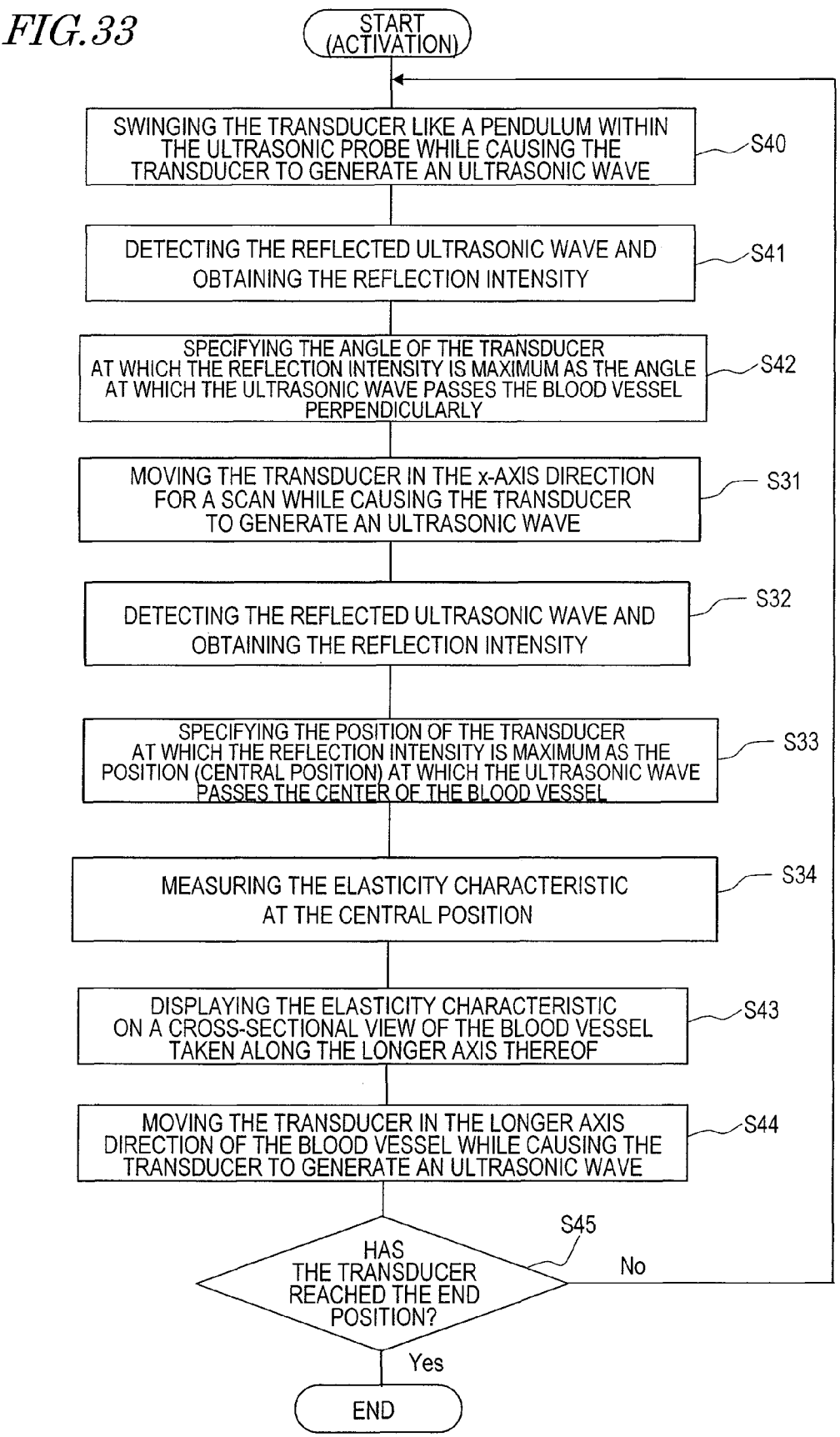
FIG. 33 A flowchart showing a processing procedure of measuring the elasticity characteristic of the blood vessel 3 executed by the ultrasonic diagnostic apparatus 11 in Embodiment 4.

FIG. 33 is a flowchart showing a processing procedure of measuring the elasticity characteristic of the blood vessel 3 executed by the ultrasonic diagnostic apparatus 11 in this embodiment.

First in step S40, when the probe control section 25 sends a control signal to the ultrasonic probe 13 in the state where the transducer 30 is located at a certain position in the y-axis direction, the motor 111 causes the transducer 30 to swing like a pendulum within the ultrasonic probe 13 while causing the transducer 30 to generate an ultrasonic wave.

In step S41, the intensity information generation section 23 detects a reflected wave of the ultrasonic wave transmitted during the pendulum-like swing from one rotation end (+90 degrees) to the other rotation end (−90 degrees), and obtains a reflection intensity distribution.

In step S42, the central position determination section 24 specifies the angle of the transducer 30 at which the reflection intensity is maximum as the angle at which the ultrasonic wave passes the blood vessel perpendicularly. Then, when the control section 26 instructs the same processing as that of steps S31 through S34 in FIG. 29 to be executed, the phase detection section 17, the filtering section 18, the calculation section 19 and the calculation data storage section 20 operate to select the central position of the cross-section perpendicular to the blood vessel and measure the elasticity characteristic of the blood vessel 3 at the central position.

In step S43, the display section 21 displays the cross-section along the longer axis of the blood vessel and also displays the elasticity characteristic measured by the calculation section 19 as being superimposed on the cross-sectional view thereof.

In step S44, the probe control section 25 moves the transducer in the longer axis direction of the blood vessel (y-axis direction) by a certain distance while causing the transducer to generate an ultrasonic wave.

In step S45, the probe control section 25 determines whether or not the transducer 30 has reached the end position. When the transducer 30 has not reached the end position, the processing returns to step S40. When the transducer 30 has reached the end position, the processing is finished.

By the processing of steps S40 through S42, the adjustment is made such that the ultrasonic wave is incident on the blood vessel perpendicularly. Also by the processing of steps S31 through S33 described above, the position of the transducer 30 at which the reflection intensity is maximum is specified as the central position, and the elasticity characteristic of the blood vessel 3 is measured at the central position. Therefore, the distortion of the blood vessel can be accurately measured, and the elasticity characteristic can be accurately measured.

In the above-described processing procedure, the transducer 30 is first swung like a pendulum to adjust the ultrasonic wave to be incident on the blood vessel perpendicularly, and then the transducer 30 is moved in the longer axis direction of the blood vessel. This order is merely an example. For example, while being moved in the longer axis direction of the blood vessel, the transducer 30 may be swung like a pendulum at each position to adjust the ultrasonic wave to be incident on the blood vessel perpendicularly.

In Embodiments 3 and 4, the position (central position) of the transducer 30 at which the reflection intensity is maximum is specified, and the elasticity characteristic of the blood vessel 3 is measured at the central position with the reason that the acoustic line from this position passes the center of the cross-section of the blood vessel 3 along the shorter axis.

Alternatively, methods which do not directly use the reflection intensity are conceivable. For example, while being generating an ultrasonic wave, the transducer is moved in the x-axis direction for performing a scan and receives the reflected wave. Based on each reflective wave, the thickness distortion amount of the tissue of the blood vessel is measured using the property value calculation section 32. Upon receiving the measurement results of the distortion amount, the central position determination section 24 specifies the position in the length direction of the transducer 30 at which the distortion amount is maximum. It is considered that when the distortion amount is maximum, the acoustic line passes the center of the cross-section of the blood vessel 3 along the shorter axis. The reason for this is as follows. The thickness distortion gradually decreases from the center to the end of the cross-section, and accordingly, the reflection intensity at the top and bottom surfaces of the thickness also decreases. At the end of the blood vessel, the ultrasonic wave is not reflected at the top surface or the bottom surface of the thickness. It is considered that in a range, including the center, in which the reflection intensity at the top and bottom surfaces of the thickness is sufficient, the thickness distortion caused by the acoustic line passing the center is maximum. For this reason, the position specified by the above-described processing is the central position. The property value calculation section 32 can measure the elasticity characteristic of the blood vessel 3 at the central position.

The processing procedure of the above-described method for measuring the thickness distortion of the tissue of the blood vessel is the same as the processing procedure in Embodiment 3 except for, for example, steps S33 and 34 in FIG. 29. Specifically, instead of step S33 in FIG. 29, the property value calculation section 32 measures the distortion of the tissue of the blood vessel. Instead of step S34, the central position determination section 24 specifies the position at which the distortion of the tissue of the blood vessel is maximum as the central position, and the property value calculation section 32 measures the elasticity characteristic of the blood vessel 3 based on the reflected ultrasonic wave received at the central position.

As a result, in step S35, the elasticity characteristic at the central position is displayed. After the central position is specified, the ultrasonic wave may be transmitted and received again, or the elasticity characteristic may be measured based on the wave already received. This processing is explained regarding Embodiment 3, but is also applicable to Embodiment 4.

In Embodiments 3 and 4, the transducer 30 is moved within the ultrasonic probe 13 by a so-called rack and pinion system, but this is merely an example. Alternatively, the movement and the rotation of the case 50 and the transducer 30 may be controlled by coupling the motor 111 and/or the motor 113 with the case 50 by a belt and winding or advancing the belt by the rotation of the motor(s). The type of the motor, which is the driving device, is arbitrary, and for example, a linear motor or a voice coil motor may be usable. It would be easy for a person of ordinary skill in the art to change the structure of the ultrasonic probe 13 for moving the transducer 30 in accordance with the driving system of the motor used.

A switch (not shown) may be provided in the probe or the main body of the ultrasonic diagnostic apparatus, so that the transducer is switched either to, or not to, move and/or rotate the transducer within the ultrasonic probe. The reason why this is possible is that an operator skilled in using the probe, upon looking at a displayed image of the elasticity characteristic, could easily determine whether the measurement results of the elasticity characteristic are correct or not, namely, whether the probe is appropriately located and the elasticity characteristic of the blood vessel is measured at the center of the cross-section of the blood vessel or not. Since the ultrasonic diagnostic apparatus can be switched either to, or not to, execute the processing of making a determination on the central position, the ultrasonic diagnostic apparatus can be operated in accordance with the level of skill of the user, which improves the convenience of the ultrasonic diagnostic apparatus.

Among the different types of processing of specifying the central position described above with reference to FIG. 28 and FIG. 32, the processing of obtaining the reflection intensity by moving the transducer 30 is applicable to measure other parameters, for example, the shape or the diameter of the blood vessel 3. This means that the central position of the blood vessel can be measured also based on the measured shape thereof. For using this type of processing to measure the shape of the blood vessel 3, data on the shapes of a plurality of cross-sections is accumulated along the longer axis of the blood vessel 3 to obtain shape data. The shape data may include a thickness change of the front wall of the blood vessel 3, which is caused by the heartbeat. The processing of measuring the diameter of the blood vessel 3 is executed by calculating a difference between the reflected wave from the wall of the blood vessel 3 which is closer to the ultrasonic probe 13 located at the central position described above, and the reflected wave from the wall of the blood vessel 3 which is farther from the ultrasonic probe 13 located at the central position. The above-described processing of obtaining the reflection intensities may be pre-executed when the ultrasonic probe 13 is applied to the body surface of the test subject. In this way, subsequent processing can be executed quickly.

Embodiment 5

Figure 34:
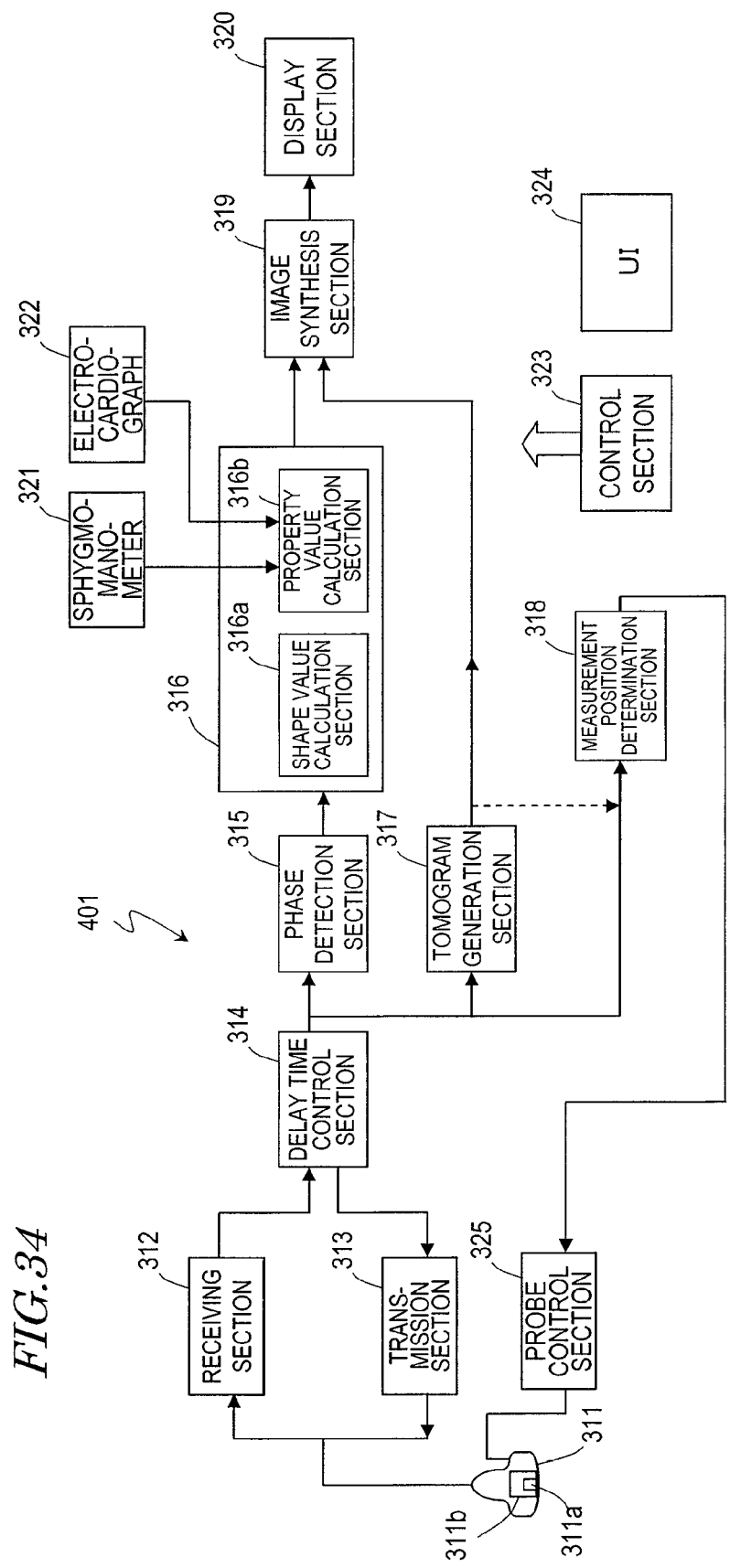
FIG. 34 A block diagram showing an ultrasonic diagnostic apparatus 401 in Embodiment 5.

Hereinafter, an ultrasonic diagnostic apparatus in Embodiment 5 according to the present invention will be described. FIG. 34 is a block diagram showing a structure of an ultrasonic diagnostic apparatus 401 according to the present invention.

The ultrasonic diagnostic apparatus 401 includes a receiving section 312, a transmission section 313, a delay time control section 314, a phase detection section 315, a calculation section 316, a tomogram generation section 317, a measurement position determination section 318, an image synthesis section 319, and a probe control section 325. The ultrasonic diagnostic apparatus 401 also includes a user interface 324 for allowing the user to issue an instruction to the ultrasonic diagnostic apparatus 401 and a control section 323 formed of a microcomputer or the like for controlling these elements based on the instruction from the user interface 324.

The elements shown in FIG. 34 do not need to be formed of independent hardware. For example, the phase detection section 315, the calculation section 316, the measurement position determination section 318 and the like may be formed of a microcomputer and software for realizing a function of thereof.

The ultrasonic diagnostic apparatus 401 is connected to an ultrasonic probe 311 for transmitting and receiving an ultrasonic wave and a display section 320 for displaying the measurement results. The ultrasonic probe 311 and the display section 320 may be included in the ultrasonic diagnostic apparatus 401 or may be a general-purpose ultrasonic probe and a general-purpose display section. Needless to say, the ultrasonic probe 311 may be an ultrasonic probe included in the ultrasonic diagnostic apparatus in any of Embodiments 1 through 4. For the display section 320, a monitor used for a personal computer or the like is preferably usable, for example.

As described above, the ultrasonic probe 311 includes a plurality of transducer elements arranged one-dimensionally. Each of the transducer elements is formed of, for example, a piezoelectric element. An ultrasonic wave is transmitted by driving the piezoelectric element, and the piezoelectric element which has received an ultrasonic wave converts the ultrasonic wave into an electric signal. In the ultrasonic probe 311, the transducer for transmitting and receiving the ultrasonic wave is movable in a direction perpendicular to the direction in which the transducer elements are arranged. Such a probe (ultrasonic probe) 311 is known as a "mechanical 3D probe".

Figure 35:
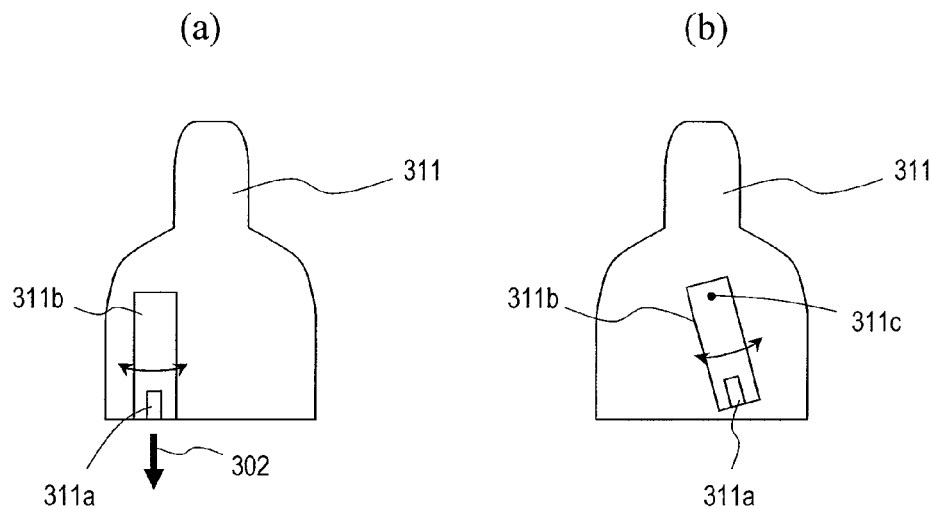
FIGS. 35 (a) and (b) schematically show a structure of an ultrasonic probe used in Embodiment 5.

Portion (a) and (b) of FIG. 35 each show an example of the mechanical 3D probe. These mechanical 3D probes have a similar structure to that of the ultrasonic probe described in the above embodiments. In these figures, transducer elements in a transducer 311a are arranged one-dimensionally in a depth direction of the sheet of the figures. The transducer 311a is supported by a support section 311b. As represented in portion (a) of FIG. 35 with the arrow, the transducer 311a is moved in a direction perpendicular to the arranging direction of the transducer elements by the support section 311b driven by a driving mechanism such as a motor or the like. Alternatively, as shown in portion (b) of FIG. 35, the support section 311b may be rotatably supported by a shaft 311c parallel to the arranging direction of the transducer elements of the transducer 311a, and may be driven by the driving mechanism to rotate around the shaft 311c as represented with the arrows.

As the ultrasonic probe 311, a 2D array probe may be used. In this case, among a plurality of transducer elements arranged two-dimensionally, the transducer elements arranged in a line in one direction are used to scan the measurement area. By changing the line used for performing the scan, the plurality of transducer elements for transmitting and receiving the ultrasonic wave can be moved in a direction perpendicular to the line used for performing the scan. This function of the 2D array probe is realized by the transducer elements selected to be driven. Therefore, the function of the probe control section 325 described later in detail is included in the transmission section 313 and the delay time control section 314.

As described later, the probe control section 325 controls the position of the transducer 311a in the direction perpendicular to the arranging direction of the transducer 311a based on an instruction from the measurement position determination section 318.

Upon receiving an instruction from the control section 323, the transmission section 313 generates a high pressure transmission signal for driving the ultrasonic probe 311 at a specified timing. The ultrasonic probe 311 converts the transmission signal generated by the transmission section 313 into an ultrasonic wave and irradiates the test subject with the ultrasonic wave. As described later in detail, the transmission section 313 drives the ultrasonic probe 311 such that a first transmission wave and a second transmission wave are transmitted from the ultrasonic probe 311. The first transmission wave is used to determine the moving direction of the blood vessel wall included in the test subject, and the second transmission wave is used to calculate the shape value of the blood vessel wall and also calculate the property value thereof. Preferably, the transmission section 313 further generates a transmission wave for generating a tomogram (B mode image) of the measurement area. The transmission wave for generating the tomogram may also be used as the first transmission wave.

First and second reflected waves obtained by the first and second transmission waves being reflected by the inside of the test subject are each converted into an electric signal using the ultrasonic probe 311 and amplified by the receiving section 312. In this way, first and second receiving signals are generated.

The delay time control section 314 controls the transmission section 313 and the receiving section 312 to select a piezoelectric element in the ultrasonic probe 311 and adjust the timing to give a voltage to the piezoelectric element. Thus, the delay time control section 314 controls a deflection angle and the focal point of the acoustic line of each of the first and second transmission waves. The delay time control section 314 also controls a deflection angle and the focal point of each of ultrasonic waves to be received as the first and second reflected waves.

Owing to such operations of the transmission section 313, the receiving section 312 and the delay time control section 314, the first and second ultrasonic waves radiated from the ultrasonic probe 311 scan the measurement area of the test subject. Thus, the first and second receiving signals of one frame are obtained. This scan is repeated a plurality of times during one cardiac cycle of the test subject to obtain the first and second receiving signals of a plurality of frames. For example, the receiving signals of several tens of frames are obtained.

The phase detection section 315 performs quadrature detection of the second receiving signal. The calculation section 316 includes a shape value calculation section 316a and a property value calculation section 316b. The shape value calculation section 316a calculates the shape value of the test subject based on the second receiving signal processed with quadrature detection. Specifically, the shape value calculation section 316a calculates, from the second receiving signal, the motion velocities of the measurement target positions which are set two-dimensionally in a region of interest (ROI) set in the measurement area of the test subject, and finds position change amounts from the motion velocities. The property value calculation section 316b finds a distortion amount between measurement target positions or between any two measurement target positions from the position change amounts. The property value calculation section 316b also receives information on the blood pressure of the artery from a sphygmomanometer 321, and finds the elasticity characteristic from the distortion amount. A property value representing the distortion amount, the elasticity characteristic or the like is found for each target tissue interposed between the measurement target positions. Therefore, a two-dimensional distribution of the property values in the region of interest is found. The property value calculation section 316b further generates a distribution signal suitable to image display. The calculation by the calculation section 316 is performed at each cardiac cycle using an electrocardiographic waveform received from an electrocardiograph 322 as the trigger.

The tomogram generation section 317 includes, for example, a filter, a logarithm amplifier, a detector and the like, and generates, from the first receiving signal, a signal for B mode image having luminance information corresponding to the intensity (magnitude of the amplitude) of the first receiving signal.

The measurement position determination section 318 controls the probe control section 325 and thus measures the intensity of the first receiving signal while changing the position of the transducer at each cardiac cycle. The measurement position determination section 318 also estimates the position change of the axis of the blood vessel during one cardiac cycle based on the measured intensity of the receiving signal. Then, the measurement position determination section 318 controls the probe control section 325 such that the position of the transducer 311a is changed so as to match the estimated position change.

The measurement position determination section 318 may receive the first receiving signal output from the delay time control section 314 and find the signal intensity of the first receiving signal. Alternatively, the tomogram generation section 317, upon receiving the first receiving signal, may obtain amplitude information on the first receiving signal and output the amplitude information to the measurement position determination section 318. In the case where the first transmission wave is a transmission wave for a tomogram, the measurement position determination section 318 receives the amplitude information on the receiving signal obtained by the tomogram generation section 317.

The image synthesis section 319 generates an image signal in which the tomogram of the measurement area provided by the signal for B mode image generated by the tomogram generation section 317 and the two-dimensional property value distribution image provided by the distribution signal generated by the property value calculation section 316b of the calculation section 316 are superimposed, and outputs the image signal to the display section 320. Based on the image signal, the display section 320 displays the image.

Figure 36:
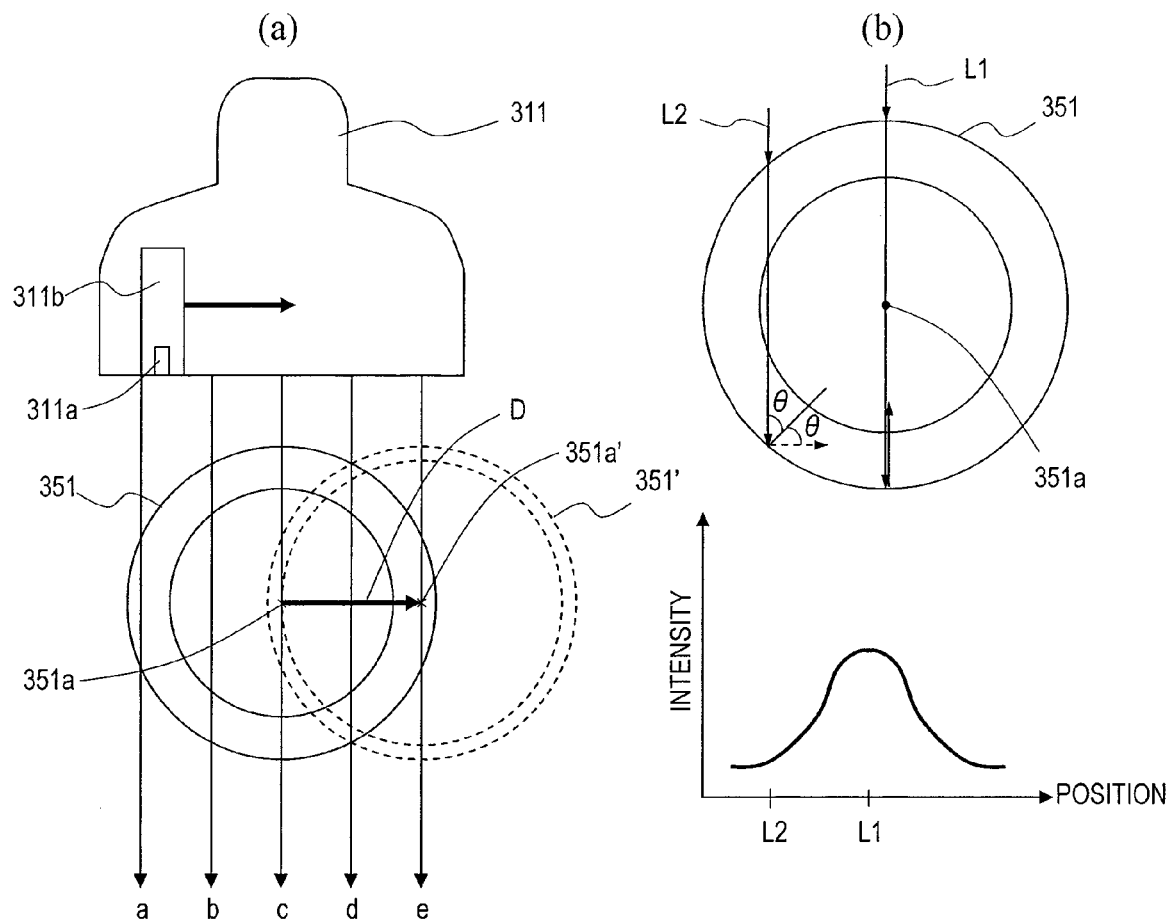
FIG. 36 (a) is a schematic view illustrating a movement of the blood vessel and a movement of a transducer 311a, and (b) is a schematic view showing a reflection intensity distribution of an ultrasonic wave in a cross-section perpendicular to an axis of the blood vessel.

Now, an operation of the ultrasonic diagnostic apparatus 401 will be described in detail. First, a method for estimating the position change of the axis of the blood vessel will be described. Portion (a) of FIG. 36 schematically shows the locations of the ultrasonic probe 311 and a blood vessel 351 for analyzing the motion of the blood vessel 351 using the ultrasonic diagnostic apparatus in this embodiment. As shown in portion (a) of FIG. 36, the transducer elements of the transducer 311a are arranged perpendicular to the sheet of the figure. The ultrasonic probe 311 is contacted to the test subject such that the axis of the blood vessel 351 is located perpendicular to the arranging direction of the transducer elements of the transducer 311a. In portion (a) of FIG. 36, arrows a through e each represent the position of an acoustic line of an ultrasonic beam which can be transmitted by the transducer 311a while the support section 311b is moved. In the case where, as represented with arrow D in portion (a) of FIG. 36, the blood vessel 351 is deviated sideways to a position represented by the dashed line 351' at the maximum during one cardiac cycle, the position of the acoustic line of the ultrasonic beam transmitted from the transducer 311a is moved from c to e in accordance with the movement of the blood vessel 351. Owing to this, the ultrasonic beam can be transmitted from the ultrasonic probe 311 such that the ultrasonic beam always passes the axis 351a of the blood vessel 351, and the reflected wave can be received by the ultrasonic probe 311.

In the case where the test subject is still, it is considered that the sideway deviation of the blood vessel 351 matches one cardiac cycle as described above. Therefore, the position change of the axis 351a of the blood vessel 351 during one cardiac cycle is estimated and the position of the acoustic line of the ultrasonic beam to be transmitted from the transducer 311a is changed so as to match the estimated position change. In this way, the influence of the sideway deviation of the blood vessel can be suppressed, the motion of the blood vessel wall can be accurately analyzed, and the elasticity characteristic distribution of the blood vessel wall can be accurately found.

The position of the axis 315a of the blood vessel 351 can be estimated by measuring the receiving intensity of the reflected wave. Portion (b) of FIG. 36 is a graph showing the relationship between the intensity of the reflected wave and the position of the acoustic line of the ultrasonic beam, the relationship being obtained when the ultrasonic beam is transmitted along a cross-section perpendicular to the axis of the blood vessel 351. Above the graph, the cross-section of the blood vessel 351 is schematically shown.

The blood vessel 351 has a tubular shape surrounding the axis 351a as the center. Therefore, the angle of reflection of ultrasonic wave by the border between an extravascular tissue and the adventitia of the blood vessel wall or by the border between the intima of the blood vessel wall and the blood flow is equal to the angle of incidence of the ultrasonic wave with respect to the radial direction (the direction of the line perpendicular to the tangential line). Accordingly, as the direction of the acoustic line is closer to the radial direction, the detected intensity of the reflected wave is higher. As the angle made by the direction of the acoustic line and the radial direction is closer to 90 degrees, the detected intensity of the reflected wave is lower. For example, as shown in portion (b) of FIG. 36, when the ultrasonic beam having an acoustic line L1 passing the axis of the blood vessel 351 is transmitted, the intensity of the reflected wave of the ultrasonic wave having the acoustic line L1 is highest. By contrast, angle θ made by an acoustic line L2 and the radial direction is not small, and so the intensity of the reflected wave is low. In this manner, as shown in portion (b) of FIG. 36, the intensity of the reflected wave is highest when the ultrasonic beam passes the axis of the blood vessel 351 and decreases as the ultrasonic beam becomes farther from the position of the axis.

Using this relationship, the following can be estimated. In the case where the blood vessel 351 is not deviated sideways, when an ultrasonic wave is transmitted while the position of the transducer 311a is changed within the ultrasonic probe 311 as shown in portion (a) of FIG. 36 and the intensity of the reflected wave is measured, the axis of the blood vessel is located on the acoustic line providing the strongest reflected wave or in the vicinity thereof.

In the case where the blood vessel 351 is deviated sideways, while the position of the transducer 311a is changed, the axis of the blood vessel may be moved. However, since the sideway deviation of the blood vessel has a cycle matching the cardiac cycle, the position change of the axis of the blood vessel during one cardiac cycle is the same in all the cardiac cycles. Namely, the position of the axis after a prescribed time period from the start of the cardiac cycle is the same in all the cardiac cycles. Using this, the reflection intensity at all the positions of a through e can be obtained at an arbitrary time during one cardiac cycle by transmitting and receiving an ultrasonic wave and measuring the intensity of the reflected wave while the position of the transducer 311a is changed at each cardiac cycle as represented with, for example, a through e in portion (b) of FIG. 36. Therefore, by determining the position at which the reflection intensity is strongest at each time during one cardiac cycle, the position of the axis of the blood vessel at each time can be estimated, and thus the position change of the axis of the blood vessel during one cardiac cycle can be estimated. According to the present invention, the position change of the axis of the blood vessel during one cardiac cycle is estimated using this method, and the elasticity characteristic is measured using the information on the estimates position.

Now, with reference to FIG. 34, portion (a) of FIG. 36, FIGS. 37, 38 and 39, a procedure of measuring the elasticity characteristic using the ultrasonic diagnostic apparatus 401 will be described in detail.

Figure 37:
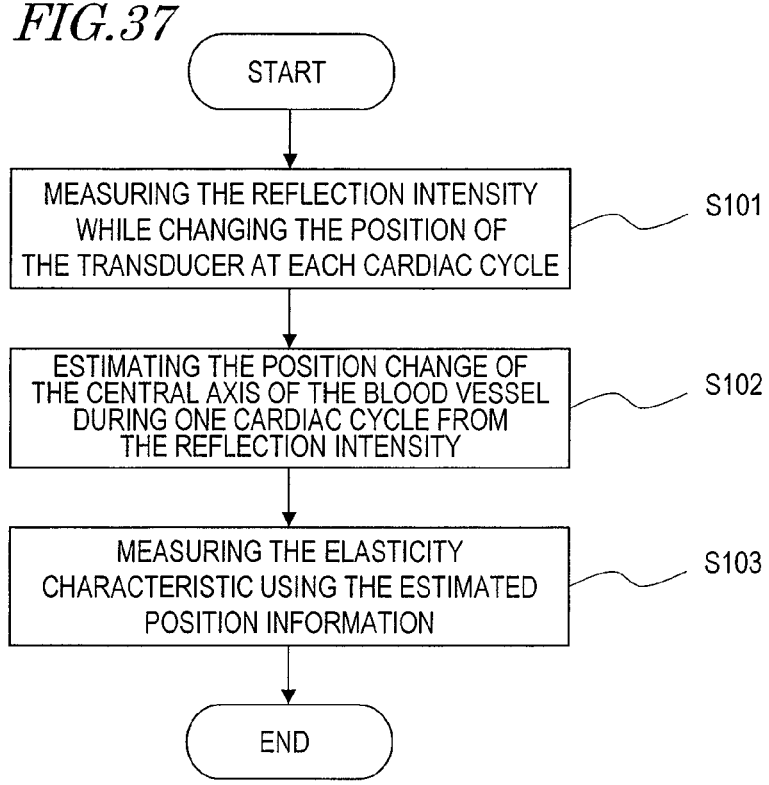
FIG. 37 A flowchart showing an operation of the ultrasonic diagnostic apparatus 401 in Embodiment 5.

As shown in FIG. 37, first, while the position of the transducer is changed at each cardiac cycle, the intensity of the reflected wave is measured (step S101). As shown in portion (a) of FIG. 36, the distance by which the transducer 311a is to be moved is determined in accordance with the moving distance of the blood vessel 351. Usually, the moving distance of the sideways deviation of the blood vessel is about several millimeters, and the moving distance of the transducer 311a is determined in accordance with a desired resolving power. In the example of portion (a) of FIG. 36, the transducer 311a is moved to the five positions of a through e.

Figure 38:
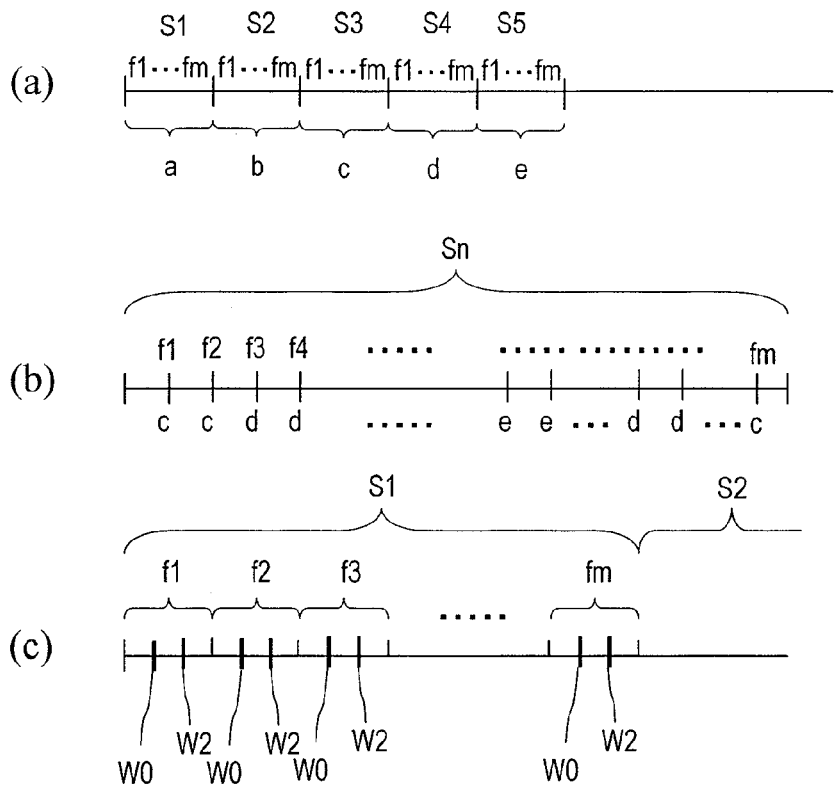
FIG. 38 (a) shows positions of the transducer for a measurement performed to estimate a position change of the blood vessel, (b) shows positions to which the transducer is moved so as to match the estimated position change of the blood vessel, and (c) shows timings to transmit an ultrasonic wave for finding a shape value and a property value of the blood vessel.

Portion (a) of FIG. 38 shows a position of the transducer 311a at each cardiac cycle. In the first cardiac cycle S1, the position of the transducer 311a is fixed to the position a, and the first transmission wave is transmitted. Each time the cardiac cycle is changed to S2, S3, S4 and S5, the position of the transducer 311a is moved to the positions b, c, d and e, and the first transmission wave is transmitted. The movement of the transducer 311a of the ultrasonic probe 311 to a prescribed position is performed by the probe control section 325 based on a control signal output from the measurement position determination section 318.

As described later, the elasticity characteristic is found by obtaining a measurement value m times during one cardiac cycle. Therefore, the position of the axis of the blood vessel can be estimated with the resolving power of 1/m. In one cardiac cycle, the period by which the measurement value is obtained each of the m times is referred to as the "frame". For measuring the elasticity characteristic, the measurement area is scanned by the second ultrasonic wave to obtain the reflected wave frame by frame. The reflection intensity of the reflected wave of the first transmission wave for estimating the position change of the axis of the blood vessel is found frame by frame in each cardiac cycle.

The first transmission wave may be any type of ultrasonic wave as long as the reflection intensity is obtained. The tomogram generation section 317 generates a signal obtained by converting the amplitude of the receiving signal into a luminance. Therefore, a transmission wave for a tomogram may be used as the first transmission wave, and the measurement position determination section 318 may receive the intensity information on the signal obtained from the tomogram generation section 317. Alternatively, the measurement position determination section 318 may receive the receiving signal output from the delay time control section 314 and convert the receiving signal into the intensity information on the receiving signal.

As shown in portion (a) of FIG. 36, at the start of each cardiac cycle, the axis 351a of the blood vessel 351 matches the position c. When the axis 351a is deviated sideways by the maximum distance as represented with arrow D, the axis 351a is moved to the position 351' represented with the dashed line. At this point, the axis 351' of the blood vessel matches the position e.

Figure 39:
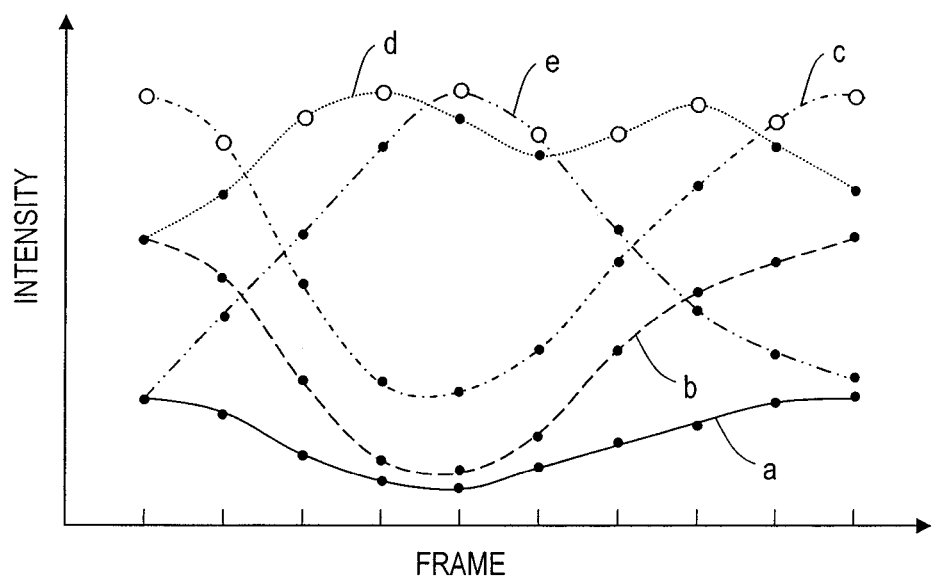
FIG. 39 A diagram showing results of measuring an intensity of a reflected wave while the position of the transducer is changed at each cardiac cycle.

FIG. 39 is a graph in which the intensity of the receiving signal of the reflected wave obtained in this manner is plotted with respect to the frame. Since the intensity of the receiving signal is measured while the position of the transducer 311a is moved to a, b, c, d and e at each cardiac cycle, the intensity of the receiving signal of the reflected wave at the positions a, b, c, d and e is obtained in each frame. Data obtained at each of the positions a, b, c, d and e of the transducer 311a is represented as a curve. At each frame, the maximum data is represented with a white circle.

The measurement position determination section 318 estimates the position change of the axis of the blood vessel during one cardiac cycle from the reflection intensities obtained in this manner (step S102). As described above, the position of the transducer at which the reflection intensity is highest is the position of the axis 351a of the blood vessel. As shown in portion (a). of FIG. 36, in the first frame of each cardiac cycle, i.e., in frame f1, the axis 315a of the blood vessel 351 is at the position c. Therefore, the intensity of the reflected wave obtained at the position c is high as shown in FIG. 39. As the time passes, namely, as the frame number increases, the axis 351a moves to the position d and then to the position e. Therefore, the position at which the intensity of the reflected wave is highest also moves to the position d and then to the position e. Then, the blood vessel 351 returns from the position of the maximum sideway deviation to the original position. Therefore, the position at which the reflection intensity is highest also moves to the position d and then to the position c.

In this manner, from FIG. 39, the position of the axis 351a of the blood vessel 351 can be estimated to change as c, d, e, d and c during one cardiac cycle. Accordingly, by moving the transducer 311a so as to match this position change of the axis 351a, the ultrasonic wave can be transmitted so as to always pass the axis 351a of the blood vessel 351 even when the blood vessel is deviated sideways.

Next, the transducer is moved so as to match the estimated position change of the blood vessel, and the second ultrasonic wave is received (step S103). Portion (b) of FIG. 38 shows positions to which the transducer 311a is to be moved for transmitting the second ultrasonic wave. The transducer is moved so as to match the position change of the axis 351a of the blood vessel 351 determined based on FIG. 39. This position change is repeated at each cardiac cycle.

For analyzing the motion of the blood vessel wall and measuring the elasticity characteristic, the second transmission wave is transmitted frame by frame to obtain the second receiving signal. Therefore, as shown in portion (c) of FIG. 38, the second transmission wave W2 is transmitted frame by frame. Preferably, a transmission wave W0 for a tomogram is also transmitted frame by frame in order to obtain a tomogram frame by frame.

In this manner, while the transducer 311a is moved in a direction perpendicular to the arranging direction of the plurality of transducer elements thereof, the plurality of transducer elements are driven in the arranging direction to scan the measurement area with the second transmission wave. Thus, even where the blood vessel is deviated sideways, tissues of the blood vessel wall can be traced by the transmission waves transmitted from the same transducer.

Figure 40:
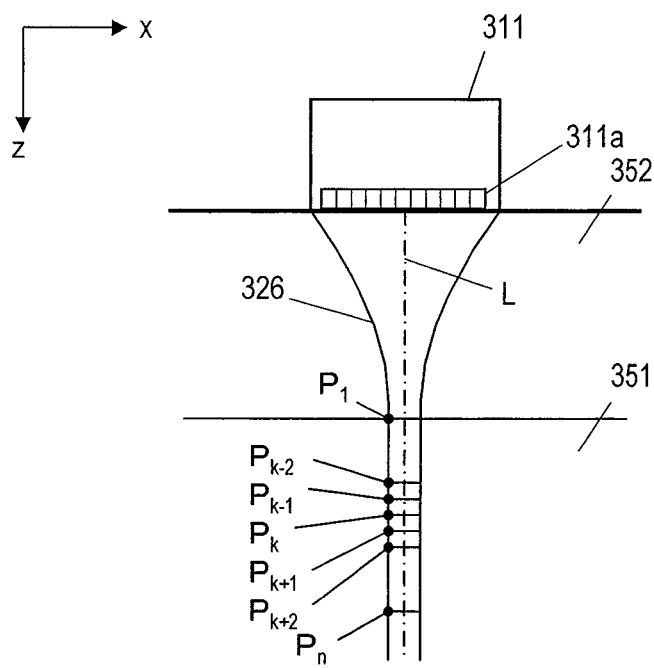
FIG. 40 A diagram illustrating measurement target positions set on an acoustic line of a second transmission wave.

Now, a method for finding the shape value and the property value from the second receiving signal obtained by receiving the second transmission wave will be described. FIG. 40 schematically shows an ultrasonic beam propagating in the tissue of the biological body. FIG. 40 is similar to FIG. 4, but is provided here to show the relationship between the ultrasonic probe 311, the transducer 311a and the like with the transmission ultrasonic wave in this embodiment.

As shown in FIG. 40, a plurality of measurement target positions $P_n$ ($P_1$, $P_2$, $P_3$, $P_k$, ... $P_n$; n is a natural number of 3 or greater) on the blood vessel wall 351 (front wall) located on an acoustic line L are arranged at a certain interval and sequentially numbered as $P_1, P_2, P_3, P_k, \ldots P_n$ from the one closest to the ultrasonic probe 311. It is assumed that a coordinate axis in which a top portion of FIG. 40 has positive values and a bottom portion of FIG. 40 has negative values is provided in a depth direction, and the measurement target positions $P_1, P_2, P_3, P_k, \ldots P_n$ respectively have coordinates $Z_1, Z_2, Z_3, Z_k \ldots Z_n$. With this assumption, an ultrasonic wave reflected at the measurement target position $P_k$ is located at $t_k=2Z_k/c$ on the time axis. Herein, c represents the sonic velocity of the ultrasonic wave in the tissue of the biological body. The reflected wave signal r(t) is phase-detected by the phase detection section 315. The detected signal is separated into a real part signal and an imaginary part signal, and input to the calculation section 316. The measurement target positions $P_n$ are set in the tissue of the blood vessel wall at a time usable as the reference of one cardiac cycle, for example, at the time when the blood vessel wall is most contracted. These positions $P_n$ move on the acoustic line L as the blood vessel wall expands and contracts, and return to the original positions at the reference time in the next cardiac cycle.

As described above, the acoustic line L moves perpendicular to the arranging direction of the transducer 311a (x direction) so as to match to the position change of the axis caused by the sideway deviation of the blood vessel. Therefore, the measurement target positions $P_n$ set at the reference time are always on the acoustic line L.

The calculation section 316 finds the position change amount by the shape value calculation section 316a from the phase-detected signal, and sequentially finds the thickness change amount and the maximum and minimum values of the thickness change amount by the property value calculation section 316b. Specifically, the shape value calculation section 316a finds a phase difference between the reflected wave signal r(t) and a reflected wave signal r(t+Δt) obtained a tiny time period Δt later, such that the alignment error of the waveforms between these reflected wave signals r(t) and r(t+Δt) is minimum, by the least squares method with a constraint that the amplitude is not changed and only the phase and the reflection position are changed between these reflected wave signals (constrained least squares method). From the phase difference, the shape value calculation section 316a finds the motion velocity $V_n(t)$ of the measurement target position $P_n$, and further integrates the motion velocity $V_n(t)$ to find the position change amount $d_n(t)$.

Figure 41:
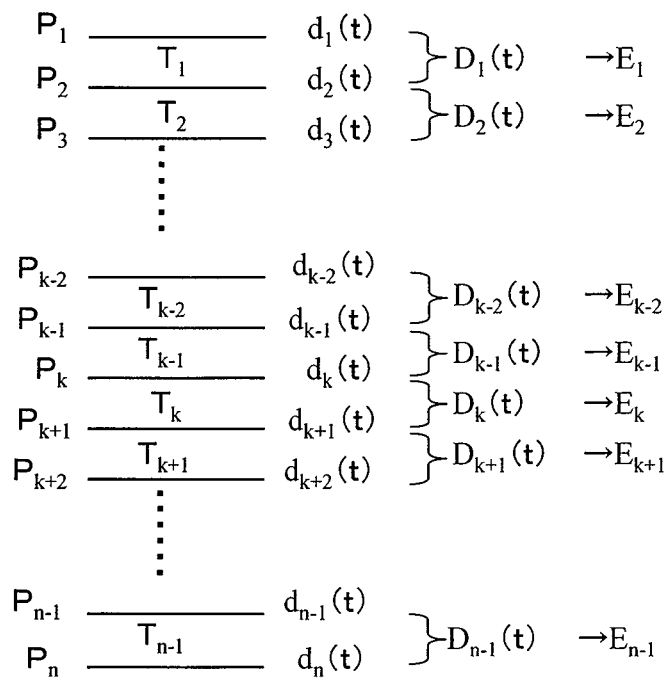
FIG. 41 A diagram showing the relationship among the measurement target position, the target tissue and the elasticity characteristic.

FIG. 41 schematically shows the relationship between the measurement target position $P_n$ and the target tissue $T_n$, the elasticity characteristic of which is to be found. The target tissue $T_n$ with a thickness h is located between the measurement target positions $P_k$ and $P_{k+1}$ adjacent to each other. In this embodiment, (n−1) pieces of target tissues $T_1 \ldots T_{n-1}$ are defined by n pieces of measurement target positions $P_1 \ldots P_n$.

The property value calculation section 316b finds the thickness change amount $D_k(t)$ from the position change amounts $d_k(t)$ and $d_{k+1}(t)$ of the measurement target positions $P_k$ and $P_{k+1}$ using the relationship of $D_k=d_k(t)-d_{k+1}(t)$.

The property value calculation section 316b also finds the maximum and minimum values of the thickness change amount. The thickness change of the tissue $T_k$ of the blood vessel front wall is caused by the blood flowing in the blood vessel formed of the blood vessel front wall being changed by the heartbeat. Therefore, the elasticity characteristic which represents the stiffness of the blood vessel of the target tissue $T_k$ can be represented by the following expression, using the maximum value $H_k$ of the thickness of the target tissue $T_k$ (the value at the minimum blood pressure), a difference $\Delta h_k$ between the maximum value and the minimum value of the thickness change amount $D_k(t)$ of the target tissue, and a pulse pressure $\Delta p$ as a difference between the minimum blood pressure and the maximum blood pressure. The minimum blood pressure and the maximum blood pressure are received from the sphygmomanometer 321.

$$E_k=\Delta p/(\Delta h_k/H_k)$$

In the above description, the elasticity characteristic of the target tissue $T_n$ between the measurement target positions adjacent to each other is found. For finding the elasticity characteristic, any two positions among the plurality of measurement target positions may be selected. In this case, the elasticity characteristic can be calculated in a similar manner using the maximum value of the thickness between the selected two positions and the difference between the maximum value and the minimum value of the change amount of the thickness between the selected two positions.

In this manner, a plurality of target tissues $T_n$ are set on the acoustic line of the second transmission wave, and the elasticity characteristic thereof is calculated. A plurality of second transmission waves are transmitted in the axial direction of the blood vessel wall 351 so as to scan the measurement area. Therefore, the elasticity characteristic is found two-dimensionally in the measurement area.

Figure 42:
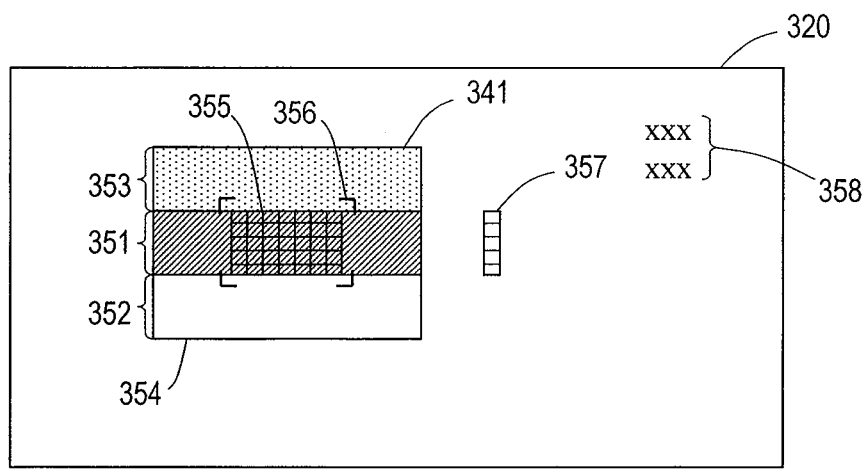
FIG. 42 A diagram showing an example of an image displayed on a display section of the ultrasonic diagnostic apparatus 401 in Embodiment 5.

FIG. 42 shows an example of an image displayed on the display section 320. On the screen of the display section 320, a tomogram 354 including the blood vessel 351 generated by the tomogram generation section 317 is shown. The tomogram 354 also includes an extravascular tissue 352 and a blood vessel lumen 353.

The tomogram 354 includes a region of interest 356 specifying an area, the elasticity characteristic of which is to be found. Any area can be specified as the region of interest 356 by the user using the user interface 324.

A two-dimensional distribution image 355 of the found elasticity characteristic is displayed on the screen as being superimposed on the tomogram 354. The two-dimensional distribution image 355 is displayed with color tones or gradation levels suitable to the values of the elasticity characteristic. A bar 357 representing the correspondence between the value of the elasticity characteristic and color tones or the gradation levels is also displayed on the screen. A numerical value 358 such as an average value, a standard deviation or the like of the elasticity characteristic may be displayed.

As described above, with the ultrasonic diagnostic apparatus in this embodiment, the measurement position determination section controls the probe control section and thus measures the intensity of the first receiving signal while changing the position of the transducer at each cardiac cycle. Based on the measured intensity, the measurement position determination section estimates the position change of the axis of the blood vessel during one cardiac cycle and controls the probe control section such that the position of the transducer changes so as to match the estimated position change. Therefore, according to the ultrasonic diagnostic apparatus in this embodiment, even where the blood vessel is translated in parallel to the axis thereof, generation of a measurement error caused by the movement of the blood vessel can be suppressed with a relatively simple circuit configuration with no need to analyze the movement of the blood vessel three-dimensionally and an accurate elasticity characteristic can be found.

Embodiment 6

Hereinafter, an ultrasonic diagnostic apparatus in Embodiment 6 according to the present invention will be described.

Figure 43:
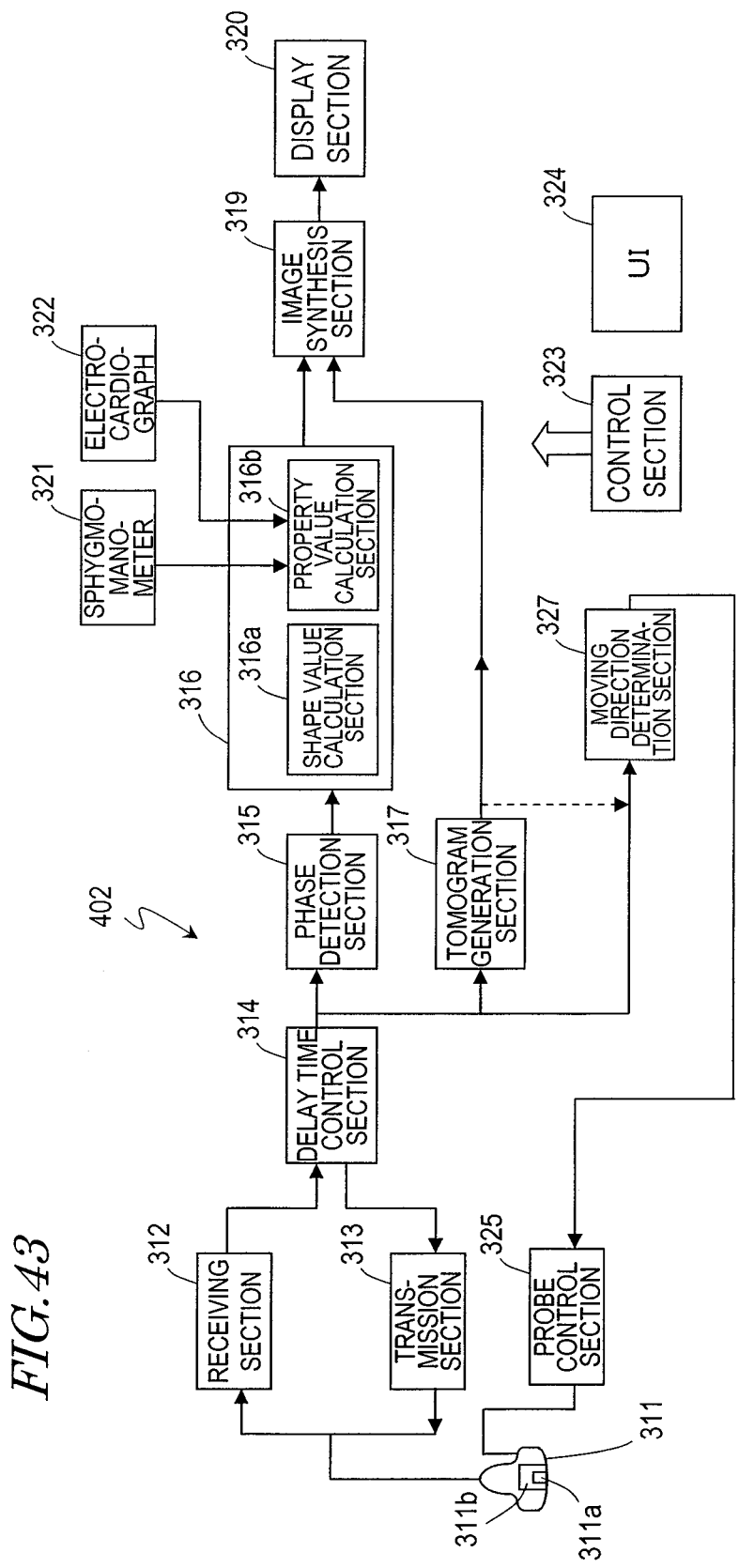
FIG. 43 A block diagram showing an ultrasonic diagnostic apparatus 402 in Embodiment 6.

FIG. 43 is a block diagram showing a structure of an ultrasonic diagnostic apparatus 402 according to the present invention.

Unlike in Embodiment 5, the ultrasonic diagnostic apparatus 402 includes a moving direction determination section 327 instead of the measurement position determination section 318 in Embodiment 5.

In Embodiment 5, the position change of the axis of the blood vessel is first estimated by measuring the intensity of the reflected wave while moving the transducer of the ultrasonic probe, and the measurement is performed after the transducer is moved so as to match the estimated position change. By contrast, in this embodiment, the measurement is performed while the moving direction of the axis of the blood vessel is searched for in real time.

Figure 44:
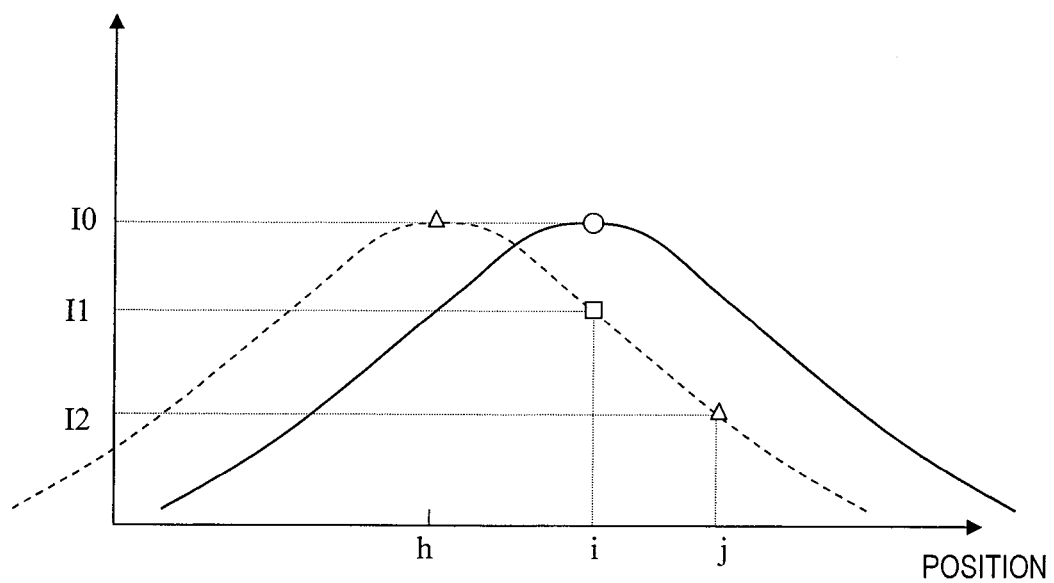
FIG. 44 A diagram illustrating a method for tracing the movement of the blood vessel in Embodiment 6.

FIG. 44 shows a reflection intensity distribution of the ultrasonic wave transmitted toward the blood vessel. As described above with reference to portion (b) of FIG. 36, when an ultrasonic wave is transmitted along a cross-section perpendicular to the axis of the blood vessel and the intensity of the reflected wave is measured, the intensity of the reflected wave of the ultrasonic beam having an acoustic line passing the axis is highest, and the intensity of the reflected wave decreases as the acoustic line becomes farther from the axis. In FIG. 44, the highest intensity I0 is obtained at a position i, and the axis of the blood vessel is located at the position i.

In the case where the blood vessel is deviated sideways and the axis moves, there are only two moving directions along the cross-section perpendicular to the axis of the blood vessel. For example, it is assumed that the axis moves in a negative direction in FIG. 44 and the axis of the blood vessel moves to a position h. When an ultrasonic wave is transmitted to the post-movement blood vessel and the intensity of the reflected wave is measured, the reflection intensity shows the distribution represented with the dashed line. When an ultrasonic wave is transmitted at the position i and the intensity of the reflected wave is measured after the blood vessel is moved, the intensity decreases to I1. The reason for this is that the axis of the blood vessel has been moved and is not on the position i anymore.

At this point, the position of the acoustic line of the ultrasonic beam is changed, and an ultrasonic wave is transmitted again and the intensity of the reflected wave is measured. In the case where the moving direction of the blood vessel matches the direction in which the position of the acoustic line is changed for the second transmission of the ultrasonic wave, the intensity of the reflected wave obtained from the second transmission is higher than the reflected strength I1 obtained at the first measurement after the movement of the blood vessel. The reason for this is that by moving the position of the acoustic line for the second transmission, the position is made closer to the position of the axis of the post-movement blood vessel. For example, when an ultrasonic wave is transmitted for the second time at the position h, the intensity of the reflected wave is I0, which is higher than I1.

By contrast, in the case where the moving direction of the blood vessel is opposite to the direction in which the position of the acoustic line is changed for the second transmission of the ultrasonic wave, the intensity of the reflected wave obtained from the second transmission is lower than the reflected strength I1 obtained at the first measurement after the movement of the blood vessel. The reason for this is that by moving the position of the acoustic line for the second transmission, the position is made farther from the position of the axis of the post-movement blood vessel. For example, when an ultrasonic wave is transmitted for the second time at a position j, the intensity of the reflected wave is I2, which is lower than I1.

Accordingly, the intensity of the reflected wave is monitored; and when the intensity is decreased to a value equal to or lower than a prescribed value, it is regarded that the blood vessel has been moved and the position of the transducer is moved in either direction. In the case where the moving direction of the transducer matches the moving direction of the blood vessel, the match can be confirmed because the reflection intensity increases. When the reflection intensity further decreases, it is understood that the moving direction of the transducer is opposite to the moving direction of the blood vessel.

Figure 51:
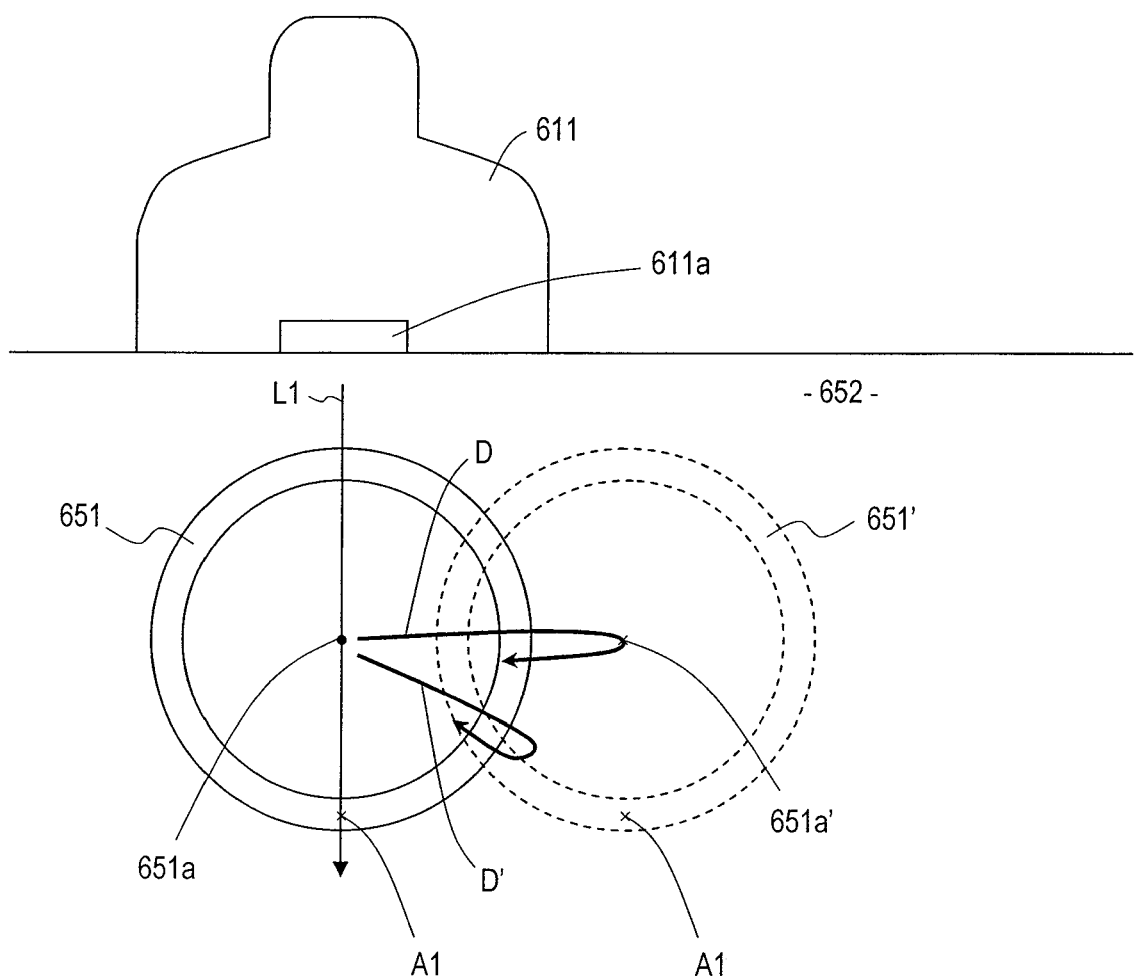
FIG. 51 A diagram illustrating a translational movement to a position parallel to the axis of the blood vessel.

The movement of the blood vessel matches one cardiac cycle. Therefore, when the moving direction of the transducer is opposite to the moving direction of the blood vessel, the measurement in that cardiac cycle is finished. At the next cardiac cycle, the transducer is moved in the opposite direction from the direction in the immediately previous cycle. As shown in FIG. 51, the blood vessel moves in one direction from the start of the cardiac cycle. The moving direction is inverted at the position farthest from the initial position, and the blood vessel returns to the original position.

In order to realize such an operation, the moving direction determination section 327 compares the intensity of the first receiving signal in one frame with that of the immediately previous frame on a frame-by-frame basis. When the intensity is decreased to a value equal to or lower than a prescribed value, the moving direction determination section 327 controls the probe control section 325 to move the transducer 311a in a direction perpendicular to the arranging direction of the transducer elements thereof.

When the moving direction determination section 327 controls the probe control section 325 to move the transducer 311a, the transmission section 313 drives the ultrasonic probe 311 to transmit the first transmission wave for the second time. The moving direction determination section 327 compares the intensity of the first receiving signal obtained from the first transmission wave transmitted for the second time, with the intensity of the first receiving signal obtained from the first transmission wave transmitted for the first time. In the case where the intensity does not increase, the moving direction of the transducer is opposite to the moving direction of the blood vessel. Therefore, the moving direction determination section 327 outputs a signal to the control section 323 to finish the measurement in that cardiac cycle. The moving direction determination section 327 also stores the moving direction of the transducer. When the measurement in the immediately previous cardiac cycle is finished in the middle, the moving direction determination section 327 determines the moving direction of the transducer such that the transducer moves in the opposite direction to the moving direction in the immediately previous cardiac cycle.

Figure 45:
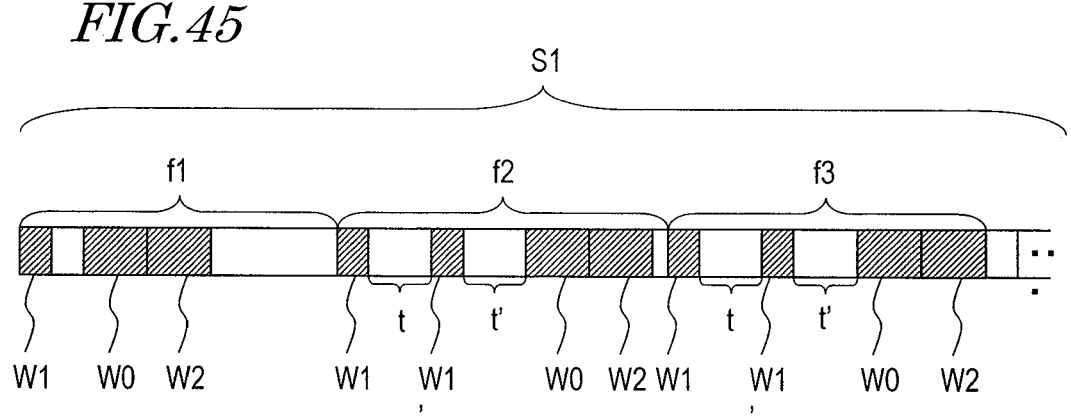
FIG. 45 A diagram showing timings to transmit an ultrasonic wave in Embodiment 6.
Figure 46:
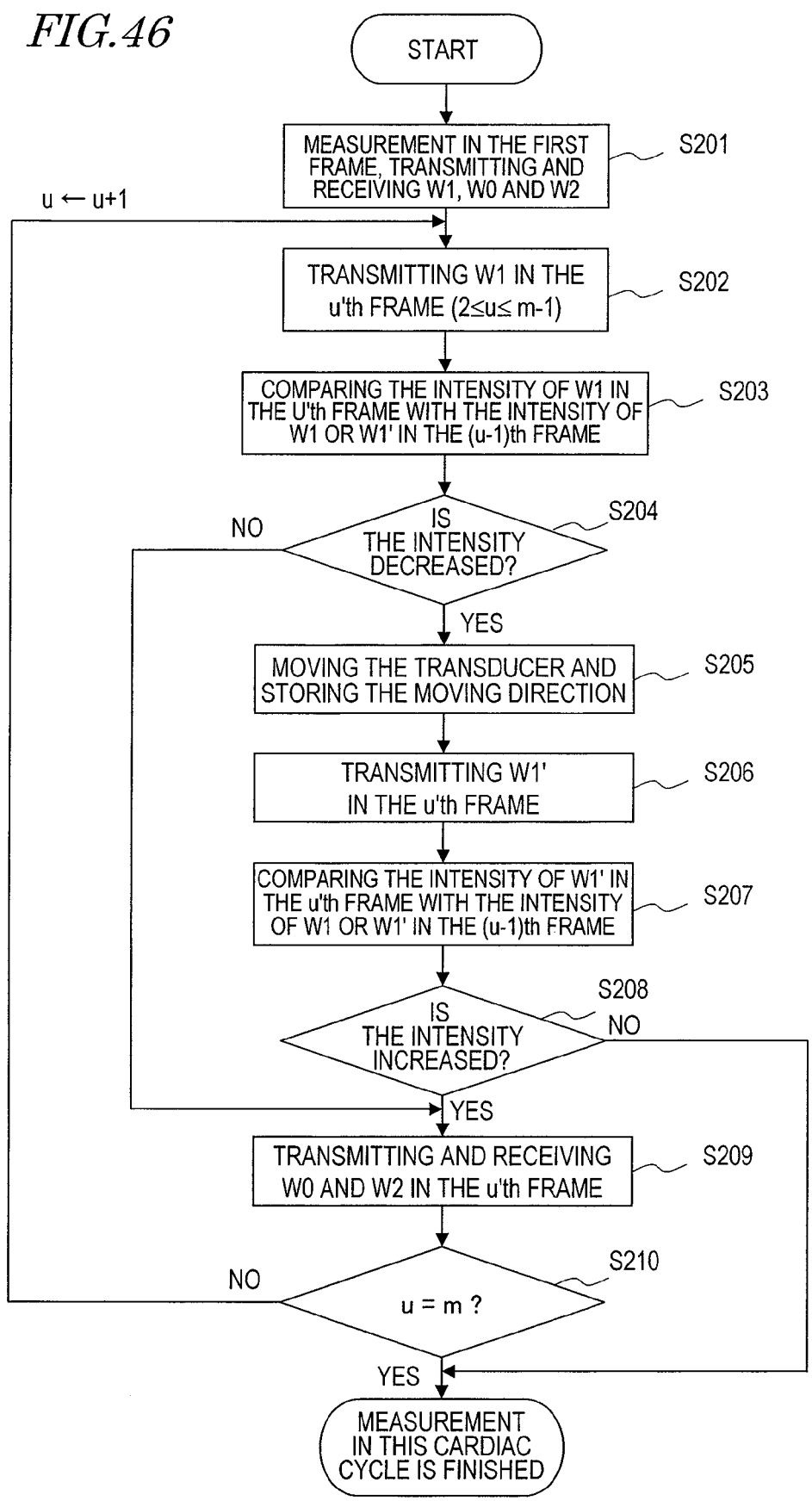
FIG. 46 A flowchart showing an operation of the ultrasonic diagnostic apparatus 402 in Embodiment 6.
Figure 48:
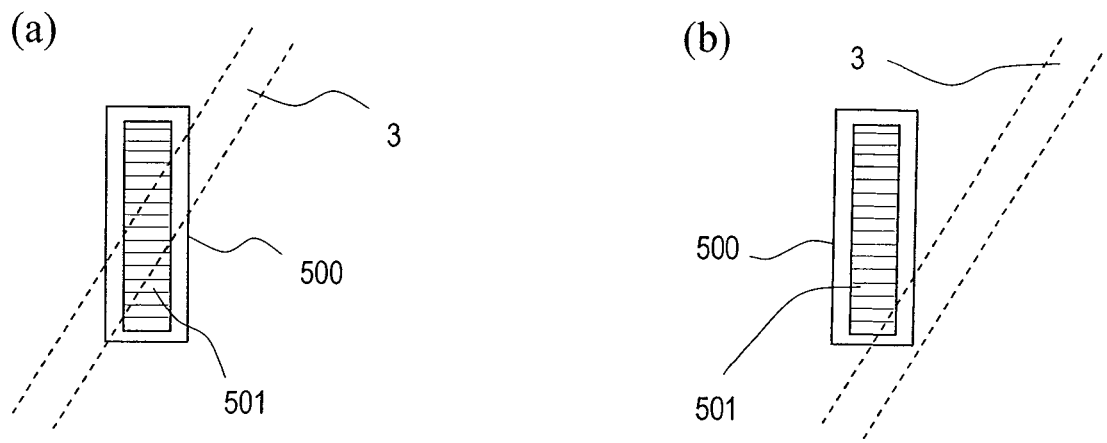
FIGS. 48 (a) and (b) are each a plan view of the probe 500 located not parallel to the blood vessel 3.
Figure 49:
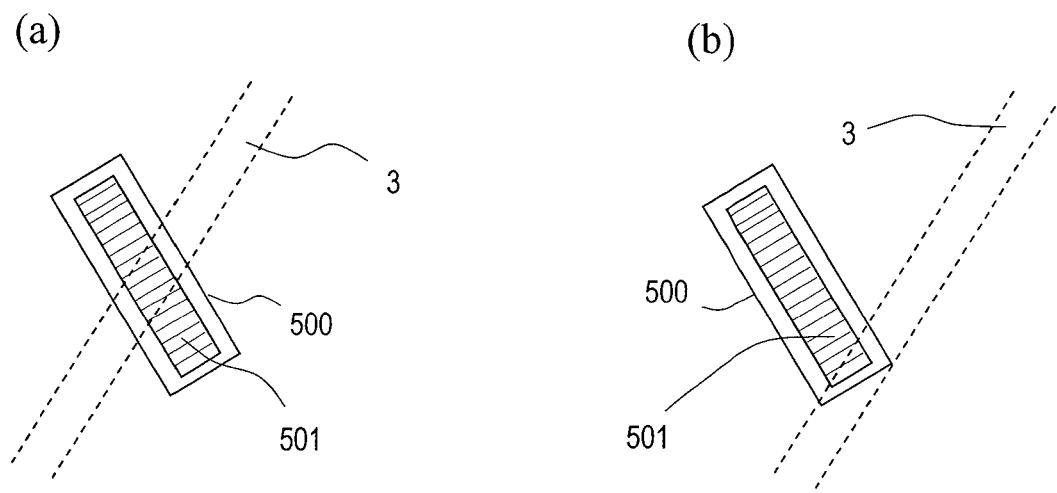
FIGS. 49 (a) and (b) are each a plan view of the probe 500 located not parallel to the blood vessel 3.

Now, with reference to FIG. 45 and FIG. 46, an operation of the ultrasonic diagnostic apparatus 402 will be described in more detail. FIG. 45 shows timing of the transmission wave transmitted from the transmission section 313. FIG. 46 is a flowchart showing the operation of the ultrasonic diagnostic apparatus 402.

As shown in FIG. 45, in the first frame of one cardiac cycle, a first transmission wave W1 for monitoring the position of the blood vessel is output, and then a image generation transmission wave W0 for generating a tomogram and a second transmission wave W2 for analyzing the motion of each of tissues in the measurement area and finding the elasticity characteristic are output. In the second and later frames, the first transmission wave W1 is output, and time t later, the first transmission wave W1' is output again. Time t' after the output of the transmission wave W1', the image generation transmission wave W0 and the second transmission wave W2 are output. The first transmission wave W1' output for the second time is used in the second and later frames in the case where the intensity of the reflected wave is lower than that in the immediately previous frame. Therefore, the first transmission wave W1' may be output for the second time only when the intensity of the reflected wave is decreased. However, even when the first transmission wave W1' is not output, it is preferable that the timing to output the image generation transmission wave W0 and the timing to output the second transmission wave W2 are the same in all the frames.

First, as an initial state, the position of the transducer 311a is preset such that the acoustic line of the ultrasonic wave transmitted from the transducer 311a is located on the axis of the blood vessel 351 or in the vicinity thereof. For example, as in Embodiment 5, the ultrasonic wave may be transmitted at the start of each cardiac cycle while the position of the transducer is changed at each cardiac cycle, and the reflection intensity may be measured. In this way, the position of the axis of the blood vessel at the start of the cardiac cycle can be determined.

As shown in FIG. 46, at the start of the measurement, the ultrasonic diagnostic apparatus 402 first performs a measurement in the first frame (step S201). Specifically, the first transmission wave W1, the image generation transmission wave W0 and the second transmission wave W2 are transmitted from the ultrasonic probe 311, and the respective receiving signals are obtained.

Next, the first transmission wave W1 of the second frame (u=2) is transmitted from the ultrasonic probe 311, and a receiving signal is obtained (step S202). The intensity of the receiving signal of the reflected wave obtained from the first transmission wave W1 in the first frame is compared with that in the second frame (step S203). When the intensity is decreased to a value equal to or lower than a prescribed value (YES in step S204), this means that the axis of the blood vessel has been moved and the acoustic line of the ultrasonic wave is deviated from the axis. Therefore, the transducer 311a is moved and the moving direction and the frame in which the movement is performed are stored (step S205). In the case where the measurement in the immediately previous cardiac cycle is finished in the middle, the moving direction of the transducer in the immediately previous cardiac cycle has been stored. Therefore, the moving direction determination section 327 instructs the probe control section 325 to move the transducer in the opposite direction to the moving direction in the frame which is at substantially the same time as the current frame.

Next, the first transmission wave W1' is transmitted for the second time from the ultrasonic probe 311, and a receiving signal is obtained (step S206). The intensity of the receiving signal of the reflected wave obtained from the first transmission wave W1 transmitted for the first time is compared with the intensity of the receiving signal of the reflected wave obtained from the first transmission wave W1' transmitted for the second time (step S207). When the intensity is increased to a value equal to or higher than a prescribed value (NO in step S208), it is estimated that the moving direction of the transducer 311a is opposite to the moving direction of the blood vessel and so the movement of the blood vessel could not be traced accurately. Therefore, the measurement in this cardiac cycle is finished.

When the intensity of the receiving signal of the reflected wave obtained from the first transmission wave W1 is not decreased to a value equal to or lower than the prescribed value in the first frame or in the second frame (NO in step S204), it is estimated that the blood vessel has not been moved. Therefore, in the second frame, the image generation transmission wave W0 and the second transmission wave W2 are transmitted from the ultrasonic probe 311 and the respective receiving signals are obtained (step S209).

Next, the frame number of the current frame is determined (step S210). When the current frame number u is equal to or larger than the final frame number m of one cardiac cycle, the measurement in this cardiac cycle is finished. When u is smaller than m, the processing returns to step S202 with u+1 being set as the new u. Then, the measurement is repeated in the same procedure. In this manner, the movement of the blood vessel can be traced in real time such that the acoustic line of the ultrasonic wave to be transmitted is located on the axis of the moving blood vessel or in the vicinity thereof. Thus, the shape value and the property value of the blood vessel wall can be accurately found.

In Embodiments 5 and 6, as represented in FIG. 51 with arrow D, the axis of the blood vessel moves in a direction perpendicular to the acoustic line L1. Alternatively, as represented with arrow D', the axis of the blood vessel may move in the depth direction. In the case where the axis of the blood vessel moves in the direction of arrow D', the motion of the axis of the blood vessel is separated into a component perpendicular to the acoustic line L1 and a component parallel to the acoustic line L1. The component perpendicular to the acoustic line L1 can be counteracted by changing the position of the transducer as described above in Embodiments 5 and 6. When the component in the perpendicular direction is counteracted, the axis of the blood vessel moves on the acoustic line L1, and so the target tissue is always on the acoustic line L1. Therefore, the shape value and the property value of the tissue of the blood vessel wall can be accurately found by the measurement performed in the above-described procedure.

The control processing described above using, for example, the flowcharts in the attached figures may be realized by a program executable by a computer. Such a computer program is distributed on the market as a product as being stored on a recording medium such as a CD-ROM or the like, or transferred via an electric communication line such as the Internet or the like. A part or all of the elements included in the ultrasonic diagnostic apparatus are realized as a general-purpose processor (semiconductor circuit) for executing the computer program, or as a dedicated processor having such a computer program and a processor in an integrated form.

INDUSTRIAL APPLICABILITY

An ultrasonic diagnostic apparatus according to the present invention is preferably usable for measuring a property and a shape characteristic of a tissue of a biological body, and is also suitable to accurately measure an elasticity characteristic. The ultrasonic diagnostic apparatus according to the present invention is also preferably usable to measure the elasticity characteristic of a blood vessel wall in order to discover an arteriosclerosis lesion or to prevent arteriosclerosis.

The invention claimed is:
1. An ultrasonic diagnostic apparatus, comprising:
an ultrasonic probe including a transducer for transmitting an ultrasonic wave and receiving the ultrasonic wave reflected by a tissue of a biological body, and a driving device, comprising one of a motor and an actuator, for changing a position of the transducer;

a probe controller configured to control the driving device to change at least one of a direction and a position at which the transducer is to transmit the ultrasonic wave;

a transmission processor configured to cause the transducer to transmit the ultrasonic wave a plurality of times in accordance with the position of the transducer;

a receiving processor configured to receive the ultrasonic wave reflected by a blood vessel repeatedly using the transducer to generate a plurality of receiving signals;

an intensity information generation processor configured to generate intensity information on a distribution of an intensity of the reflected ultrasonic wave based on the plurality of receiving signals;

and a determination processor configured to specify a position of the transducer at which the intensity of the reflected ultrasonic wave is maximum, based on the intensity information;

wherein the ultrasonic diagnostic apparatus transmits the ultrasonic wave at the specified position and calculates one of a property value and a shape measurement value of the blood vessel.

2. The ultrasonic diagnostic apparatus of claim 1, wherein:
the intensity information generation processor is configured to generate intensity information which represents a distribution of an intensity of the reflected ultrasonic wave received by each of receiving processors A and B discrete from each other on the transducer;
the determination processor is configured to determine whether or not the intensity information provided by the receiving processor A and the intensity information provided by the receiving processor B represent a maximum value at the same time; and
when the intensity information provided by the receiving processor A and the intensity information provided by the receiving processor B do not represent the maximum value at the same time, the probe controller rotates the transducer at a prescribed angle on a plane parallel to the surface of the biological body.

3. The ultrasonic diagnostic apparatus of claim 2, wherein:
when the intensity information provided by the receiving processor A and the intensity information provided by the receiving processor B do not represent the maximum value at the same time,
the probe controller rotates the transducer such that the transducer is parallel to the blood vessel based on the position of the transducer at which the intensity information provided by the receiving processor A represents the maximum value, the position of the transducer at which the intensity information provided by the receiving processor B represents the maximum value, and a distance between the receiving processors A and B.

4. The ultrasonic diagnostic apparatus of claim 2, wherein until the determination processor determines that the intensity information provided by the receiving processor A and the intensity information provided by the receiving processor B represent the maximum value at the same time, the probe controller rotates the transducer by the prescribed angle repeatedly.

5. The ultrasonic diagnostic apparatus of claim 4, wherein after the determination processor determines that the intensity information provided by the receiving processor A and the intensity information provided by the receiving processor B represent the maximum value at the same time, the determination processor specifies the position of the transducer at which the intensity of the reflected ultrasonic wave is maximum.

6. The ultrasonic diagnostic apparatus of claim 1, further comprising:
a controller configured to instruct the transmission processor and the receiving processor to respectively transmit and receive the ultrasonic wave; and
a calculation processor configured to calculate one of the property value and the shape measurement value of the blood vessel based on the ultrasonic wave received by the receiving processor;
wherein when the transducer is located at the position specified by the determination processor, the controller control instructs the transmission processor and the receiving processor to respectively transmit and receive the ultrasonic wave.

7. The ultrasonic diagnostic apparatus of claim 1, further comprising an operation processor configured to output a control signal for changing the position of the transducer, wherein the probe controller changes the position of the transducer based on the control signal.

8. The ultrasonic diagnostic apparatus of claim 1, wherein the probe controller receives the control signal from the operation processor via a network.

9. An ultrasonic diagnostic apparatus, comprising:
an ultrasonic probe including a transducer for transmitting an ultrasonic wave and receiving the ultrasonic wave reflected by a tissue of a biological body, and a driving device, comprising one of a motor and an actuator, for changing a position of the transducer;
a probe controller configured to control the driving device to change at least one of a direction and a position at which the transducer is to transmit the ultrasonic wave;
a transmission processor configured to cause the transducer to transmit the ultrasonic wave a plurality of times in accordance with the position of the transducer;
a receiving processor configured to receive the ultrasonic wave reflected by a blood vessel repeatedly using the transducer to generate a plurality of receiving signals;
an intensity information generation processor configured to generate intensity information on a distribution of an intensity of the reflected ultrasonic wave based on the plurality of receiving signals; and
a determination processor configured to specify a position of the transducer at which the intensity of the reflected ultrasonic wave is maximum, based on the intensity information;
wherein the ultrasonic diagnostic apparatus transmits the ultrasonic wave at the specified position and measures a thickness of the blood vessel including an intima-media thickness.

10. The ultrasonic diagnostic apparatus of claim 9, wherein:
the intensity information generation processor is configured to generate intensity information which represents a distribution of an intensity of the reflected ultrasonic wave received by each of receiving processors A and B discrete from each other on the transducer;
the determination processor is configured to determine whether or not the intensity information provided by the receiving processor A and the intensity information provided by the receiving processor B represent a maximum value at the same time; and
when the intensity information provided by the receiving processor A and the intensity information provided by the receiving processor B do not represent the maximum value at the same time, the probe controller rotates the transducer at a prescribed angle on a plane parallel to the surface of the biological body.

11. The ultrasonic diagnostic apparatus of claim 10, wherein:
when the intensity information provided by the receiving processor A and the intensity information provided by the receiving processor B do not represent the maximum value at the same time,
the probe controller rotates the transducer such that the transducer is parallel to the blood vessel based on the position of the transducer at which the intensity information provided by the receiving processor A represents the maximum value, the position of the transducer at which the intensity information provided by the receiving processor B represents the maximum value, and a distance between the receiving processors A and B.

12. The ultrasonic diagnostic apparatus of claim 10, wherein until the determination processor determines that the intensity information provided by the receiving processor A and the intensity information provided by the receiving processor B represent the maximum value at the same time, the probe controller rotates the transducer by the prescribed angle repeatedly.

13. The ultrasonic diagnostic apparatus of claim 10, wherein after the determination processor determines that the intensity information provided by the receiving processor A and the intensity information provided by the receiving processor B represent the maximum value at the same time, the determination processor specifies the position of the transducer at which the intensity of the reflected ultrasonic wave is maximum.

* * * * *